US008506968B2

(12) United States Patent
Akeefe et al.

(10) Patent No.: US 8,506,968 B2
(45) Date of Patent: *Aug. 13, 2013

(54) SARS VACCINE COMPOSITIONS AND METHODS OF MAKING AND USING THEM

(75) Inventors: Hassibullah Akeefe, San Ramon, CA (US); Moiz Kitabwalla, Livermore, CA (US)

(73) Assignee: Eli Lilly and Company, Indianapolis, IN (US)

( * ) Notice: Subject to any disclaimer, the term of this patent is extended or adjusted under 35 U.S.C. 154(b) by 529 days.

This patent is subject to a terminal disclaimer.

(21) Appl. No.: 12/655,299

(22) Filed: Dec. 28, 2009

(65) Prior Publication Data

US 2011/0150929 A1 Jun. 23, 2011

Related U.S. Application Data

(63) Continuation of application No. 12/106,021, filed on Apr. 18, 2008, now abandoned, which is a continuation-in-part of application No. 11/401,434, filed on Apr. 10, 2006, now Pat. No. 7,439,052, which is a continuation-in-part of application No. 10/873,015, filed on Jun. 21, 2004, now Pat. No. 7,407,662, which is a continuation-in-part of application No. 10/601,656, filed on Jun. 20, 2003, now Pat. No. 7,407,663, which is a continuation-in-part of application No. 10/311,679, filed as application No. PCT/IB01/01099 on Jun. 21, 2001, now abandoned.

(60) Provisional application No. 60/925,628, filed on Apr. 20, 2007, provisional application No. 60/670,574, filed on Apr. 11, 2005, provisional application No. 60/669,738, filed on Apr. 8, 2005, provisional application No. 60/542,947, filed on Feb. 9, 2004, provisional application No. 60/390,066, filed on Jun. 20, 2002, provisional application No. 60/491,928, filed on Aug. 1, 2003, provisional application No. 60/533,542, filed on Dec. 31, 2003.

(30) Foreign Application Priority Data

Jun. 29, 2000 (AU) .................................. PQ8469
Dec. 28, 2000 (WO) ...................... PCT/AU00/01603

(51) Int. Cl.
*A61K 39/215* (2006.01)
*C12N 7/04* (2006.01)
*C12N 7/06* (2006.01)

(52) U.S. Cl.
USPC ........................ 424/221.1; 435/236; 435/238

(58) Field of Classification Search
None
See application file for complete search history.

(56) References Cited

U.S. PATENT DOCUMENTS

| | | |
|---|---|---|
| 3,647,624 A | 3/1972 | Evenson |
| 3,958,939 A | 5/1976 | Jones |
| 3,983,008 A | 9/1976 | Shinozaki et al. |
| 3,989,466 A | 11/1976 | Pan |
| 4,025,423 A | 5/1977 | Stonner et al. |
| 4,103,685 A | 8/1978 | Lupien et al. |
| 4,124,509 A | 11/1978 | Iijima et al. |
| 4,234,317 A | 11/1980 | Lucas et al. |
| 4,235,602 A | 11/1980 | Meyer et al. |
| 4,258,010 A | 3/1981 | Rozsa et al. |
| 4,350,156 A | 9/1982 | Malchesky et al. |
| 4,391,711 A | 7/1983 | Jackson et al. |
| 4,399,217 A | 8/1983 | Holmquist et al. |
| 4,402,940 A | 9/1983 | Nose et al. |
| 4,424,131 A | 1/1984 | Baird |
| 4,431,633 A | 2/1984 | Machlowitz et al. |
| 4,435,289 A | 3/1984 | Breslau |
| 4,463,988 A | 8/1984 | Bouck et al. |
| 4,481,189 A | 11/1984 | Prince |
| 4,522,809 A | 6/1985 | Adamowicz et al. |
| 4,540,401 A | 9/1985 | Marten |

(Continued)

FOREIGN PATENT DOCUMENTS

| | | |
|---|---|---|
| CA | 1271708 | 7/1990 |
| CN | 1189378 | 8/1998 |

(Continued)

OTHER PUBLICATIONS

Burns, et al., "Use of In Vivo Models to Study the Role of Cholesterol in the Etiology of Alzheimer's Disease", Neurochem Res. Jul. 2003, 28, 979-86 (Abstract only).

Cham, Bill E. et al., "A solvent system for delipidation of plasma or serum without protein precipitation", Journal of Lipid Research 1976, vol. 17, pp. 176-181.

(Continued)

*Primary Examiner* — Stacy B. Chen
(74) *Attorney, Agent, or Firm* — Kulpatrick Townsend & Stockton LLP

(57) ABSTRACT

Described is a composition and method for reducing the occurrence and severity of infectious diseases, especially infectious diseases such as SARS, in which lipid-containing infectious viral organisms are found in biological fluids, such as blood. The present invention employs solvents useful for extracting lipids from the lipid-containing infectious viral organism thereby creating immunogenic modified, partially delipidated viral particles with reduced infectivity. The present invention provides delipidated viral vaccine compositions, such as therapeutic vaccine compositions, comprising these modified, partially delipidated viral particles with reduced infectivity, optionally combined with a pharmaceutically acceptable carrier or an immunostimulant. The vaccine composition is administered to a patient to provide protection against the lipid-containing infectious viral organism or, in case of a therapeutic vaccine, to treat or alleviate infection against the lipid-containing infections viral organism. The vaccine compositions of the present invention include combination vaccines of modified viral particles obtained from one or more strains of a virus and/or one or more types of virus.

15 Claims, 10 Drawing Sheets

(56) References Cited

U.S. PATENT DOCUMENTS

| | | |
|---|---|---|
| 4,540,573 A | 9/1985 | Neurath et al. |
| 4,581,231 A | 4/1986 | Purcell et al. |
| 4,591,505 A | 5/1986 | Prince |
| 4,605,648 A | 8/1986 | Price |
| 4,613,501 A | 9/1986 | Horowitz |
| 4,615,886 A | 10/1986 | Purcell et al. |
| 4,643,718 A | 2/1987 | Marten |
| 4,645,512 A | 2/1987 | Johns |
| 4,647,280 A | 3/1987 | Maaskant et al. |
| 4,648,974 A | 3/1987 | Rosskopf et al. |
| 4,668,398 A | 5/1987 | Silvis |
| 4,671,909 A | 6/1987 | Torobin |
| 4,676,905 A | 6/1987 | Nagao et al. |
| 4,677,057 A | 6/1987 | Curtiss et al. |
| 4,680,320 A | 7/1987 | Uku et al. |
| 4,696,670 A | 9/1987 | Ohnishi et al. |
| 4,775,483 A | 10/1988 | Mookerjea et al. |
| 4,832,034 A | 5/1989 | Pizziconi et al. |
| 4,836,928 A | 6/1989 | Aoyagi et al. |
| 4,841,023 A | 6/1989 | Horowitz |
| 4,879,037 A | 11/1989 | Utzinger |
| 4,895,558 A | 1/1990 | Cham |
| 4,908,354 A | 3/1990 | Seidel et al. |
| 4,909,940 A | 3/1990 | Horowitz et al. |
| 4,909,942 A | 3/1990 | Sato et al. |
| 4,923,439 A | 5/1990 | Seidel et al. |
| 4,935,204 A | 6/1990 | Seidel et al. |
| 4,966,709 A | 10/1990 | Nose et al. |
| 4,970,144 A | 11/1990 | Fareed et al. |
| 5,026,479 A | 6/1991 | Bikson et al. |
| 5,080,796 A | 1/1992 | Nose et al. |
| 5,089,602 A | 2/1992 | Isliker et al. |
| 5,112,956 A | 5/1992 | Tang et al. |
| 5,116,307 A | 5/1992 | Collins |
| 5,126,240 A | 6/1992 | Curtiss |
| 5,128,318 A | 7/1992 | Levine et al. |
| 5,151,023 A | 9/1992 | Kuzuhara et al. |
| 5,152,743 A | 10/1992 | Gorsuch et al. |
| 5,187,010 A | 2/1993 | Parham et al. |
| 5,203,778 A | 4/1993 | Boehringer |
| 5,211,850 A | 5/1993 | Shettigar et al. |
| 5,236,644 A | 8/1993 | Parham et al. |
| 5,256,767 A | 10/1993 | Salk et al. |
| 5,258,149 A | 11/1993 | Parham et al. |
| 5,279,540 A | 1/1994 | Davidson |
| 5,301,694 A | 4/1994 | Raymond et al. |
| 5,354,262 A | 10/1994 | Boehringer et al. |
| 5,391,143 A | 2/1995 | Kensey |
| 5,393,429 A | 2/1995 | Nakayama et al. |
| 5,401,415 A | 3/1995 | Rauh et al. |
| 5,401,466 A | 3/1995 | Foltz et al. |
| 5,418,061 A | 5/1995 | Parham et al. |
| 5,418,130 A | 5/1995 | Platz et al. |
| 5,419,759 A | 5/1995 | Naficy |
| 5,424,068 A | 6/1995 | Filip |
| 5,476,715 A | 12/1995 | Otto |
| 5,484,396 A | 1/1996 | Naficy |
| 5,496,637 A | 3/1996 | Parham et al. |
| 5,523,096 A | 6/1996 | Okarma et al. |
| 5,565,203 A | 10/1996 | Gluck et al. |
| 5,634,893 A | 6/1997 | Rishton |
| 5,637,224 A | 6/1997 | Sirkar et al. |
| 5,652,339 A | 7/1997 | Lerch et al. |
| 5,679,260 A | 10/1997 | Boos et al. |
| 5,698,432 A | 12/1997 | Oxford |
| 5,707,673 A | 1/1998 | Prevost et al. |
| 5,719,194 A | 2/1998 | Mann et al. |
| 5,744,038 A | 4/1998 | Cham |
| 5,753,227 A | 5/1998 | Strahilevitz |
| 5,834,015 A | 11/1998 | Oleske et al. |
| 5,853,725 A | 12/1998 | Salk et al. |
| 5,855,782 A | 1/1999 | Falkenhagen et al. |
| 5,858,238 A | 1/1999 | McRea et al. |
| 5,877,005 A | 3/1999 | Castor |
| 5,879,685 A | 3/1999 | Gluck et al. |
| 5,885,578 A | 3/1999 | Salk et al. |
| 5,891,432 A | 4/1999 | Hoo |
| 5,895,650 A | 4/1999 | Salk et al. |
| 5,911,698 A | 6/1999 | Cham |
| 5,916,806 A | 6/1999 | Salk et al. |
| 5,919,369 A | 7/1999 | Ash |
| 5,928,930 A | 7/1999 | Salk et al. |
| 5,932,468 A | 8/1999 | Ristol Debart |
| 5,948,441 A | 9/1999 | Lenk et al. |
| 5,962,322 A | 10/1999 | Kozarsky et al. |
| 5,980,478 A | 11/1999 | Gorsuch et al. |
| 6,004,925 A | 12/1999 | Dasseux et al. |
| 6,017,543 A | 1/2000 | Salk et al. |
| 6,022,333 A | 2/2000 | Kensey |
| 6,037,323 A | 3/2000 | Dasseux et al. |
| 6,037,458 A | 3/2000 | Hirai et al. |
| 6,039,946 A | 3/2000 | Strahilevitz |
| 6,046,166 A | 4/2000 | Dasseux et al. |
| 6,080,778 A | 6/2000 | Yankner et al. |
| 6,127,370 A | 10/2000 | Smith et al. |
| 6,136,321 A | 10/2000 | Barrett et al. |
| 6,139,746 A | 10/2000 | Kopf |
| 6,156,727 A | 12/2000 | Garber et al. |
| 6,165,502 A | 12/2000 | Oleske et al. |
| 6,171,373 B1 | 1/2001 | Park et al. |
| 6,193,891 B1 | 2/2001 | Kent et al. |
| 6,264,623 B1 | 7/2001 | Strahilevitz |
| 6,291,228 B1 | 9/2001 | Howard et al. |
| 6,309,550 B1 | 10/2001 | Iversen et al. |
| 6,337,368 B1 | 1/2002 | Kobayashi et al. |
| 6,369,048 B1 | 4/2002 | Budowsky et al. |
| 6,395,469 B1 | 5/2002 | Sanhueza et al. |
| 6,440,387 B1 | 8/2002 | Yankner et al. |
| 6,472,421 B1 | 10/2002 | Wolozin |
| 6,605,588 B1 | 8/2003 | Lees et al. |
| 6,706,008 B2 | 3/2004 | Vishnoi et al. |
| 6,737,066 B1 | 5/2004 | Moss |
| 6,991,727 B2 | 1/2006 | Bomberger et al. |
| 7,033,500 B2 | 4/2006 | Bomberger et al. |
| 7,166,223 B2 | 1/2007 | Bomberger et al. |
| 7,195,710 B2 | 3/2007 | Bomberger et al. |
| 7,297,261 B2 | 11/2007 | Bomberger et al. |
| 7,297,262 B2 | 11/2007 | Bomberger et al. |
| 7,361,360 B2 | 4/2008 | Kitabwalla et al. |
| 7,364,658 B2 | 4/2008 | Bomberger et al. |
| 7,402,246 B2 | 7/2008 | Bomberger et al. |
| 7,407,662 B2 | 8/2008 | Cham et al. |
| 7,407,663 B2 | 8/2008 | Cham et al. |
| 7,439,052 B2 | 10/2008 | Cham |
| 7,740,872 B2 | 6/2010 | Kitabwalla et al. |
| 2001/0028895 A1 | 10/2001 | Bisgaier et al. |
| 2002/0055529 A1 | 5/2002 | Bisgaier et al. |
| 2002/0081263 A1 | 6/2002 | Yankner et al. |
| 2002/0107173 A1 | 8/2002 | Friedhoff et al. |
| 2002/0128227 A1 | 9/2002 | Hildreth |
| 2002/0183379 A1 | 12/2002 | Yankner et al. |
| 2002/0188012 A1 | 12/2002 | Bisgaier et al. |
| 2003/0018013 A1 | 1/2003 | Dasseux et al. |
| 2003/0044428 A1 | 3/2003 | Moss |
| 2003/0104350 A1 | 6/2003 | Bomberger et al. |
| 2003/0119782 A1 | 6/2003 | Cham |
| 2003/0127386 A1 | 7/2003 | Bomberger et al. |
| 2003/0133929 A1 | 7/2003 | Cham |
| 2004/0106556 A1 | 6/2004 | Zhu et al. |
| 2004/0170649 A1 | 9/2004 | Cham et al. |
| 2004/0256307 A1 | 12/2004 | Bomberger et al. |
| 2005/0016912 A1 | 1/2005 | Bomberger et al. |
| 2005/0032222 A1 | 2/2005 | Cham et al. |
| 2007/0212376 A1 | 9/2007 | Cham |
| 2008/0083671 A1 | 4/2008 | Bomberger et al. |
| 2008/0149572 A1 | 6/2008 | Bomberger et al. |
| 2008/0203022 A1 | 8/2008 | Bomberger et al. |
| 2008/0220016 A1 | 9/2008 | Cham et al. |
| 2008/0220017 A1 | 9/2008 | Cham et al. |
| 2008/0267997 A1 | 10/2008 | Cham et al. |
| 2009/0017069 A1 | 1/2009 | Akeefe et al. |
| 2009/0028902 A1 | 1/2009 | Cham et al. |
| 2009/0032468 A1 | 2/2009 | Bomberger et al. |

FOREIGN PATENT DOCUMENTS

| | | |
|---|---|---|
| DE | 2944138 | 6/1981 |
| DE | 3118072 | 11/1982 |
| DE | 3213390 | 10/1983 |
| DE | 3310263 | 9/1984 |
| EP | 0036283 | 9/1981 |
| EP | 0267471 | 5/1988 |
| FR | 2571971 | 4/1986 |
| GB | 1183506 | 3/1970 |
| JP | 55127104 | 1/1980 |
| JP | 277303 | 10/1993 |
| RU | 1116396 | 9/1984 |
| RU | 1204224 | 1/1986 |
| RU | 1752187 | 7/1992 |
| WO | WO-8809345 | 12/1988 |
| WO | WO-9503840 | 2/1995 |
| WO | WO 99/17802 A1 * | 4/1999 |
| WO | WO-9938498 | 8/1999 |
| WO | WO-0145718 | 6/2001 |
| WO | WO-0156579 | 8/2001 |
| WO | WO-0200266 | 1/2002 |
| WO | WO-0210768 | 2/2002 |
| WO | WO-0230863 | 4/2002 |
| WO | WO-02062824 | 8/2002 |
| WO | WO-03000373 | 1/2003 |

OTHER PUBLICATIONS

Cham, et al., "Changes in Electrophoretic Mobilities of alpha- and beta-Lipoproteins as a Result of Plasma Delipidation", Clinical Chemistry 1976, v. 22, 305-309.

Cham, et al., "Heterogeneity of Lipoprotein Beta", Biochemical and Biophysical Research Communications 1981, v. 103, 196-206.

Cham, et al., "Importance of Apolipoproteins in Lipid Metabolism", Chem. Biol. Interactions 1978, v. 20, 263-277.

Cham, et al., "In Vitro Partial Relipidation of Apolipoproteins in Plasma", J. Biol. Chem 1976, v. 251, 6367-6371 (Abstract only).

Cham, et al., "Lipid Apheresis in an Animal Model Causes Acute Reduction in Plasma Lipid Concentrations and Mobilisation of Lipid from Liver and Aorta", Pharmacol (Life Sci. Adv.) 1994, v. 13, 25-32.

Cham, et al., "Lipid Apheresis in an Animal Model Causes In Vivo Changes in Lipoprotein Electrophoretic Patterns", J. Clin. Apheresis 1996, v. 11, 61-70.

Cham, Bill E. et al., "Lipid Apheresis: An In Vivo Application of Plasma Delipidation with Organic Solvents Resulting in Acute Transient Reduction of Circulating Plasma Lipids in Animals", Journal of Clinical Apheresis 1995, pp. 61-69.

Cham, "Nature of the Interaction Between Low-Density Lipoproteins and Polyanions and Metal Ions, as Exemplified by Heparin and Ca2", Clinical Chemistry 1976, v. 22, pp. 1812-1816.

Cham, et al., "Phospholipids in EDTA—Treated Plasma and Serum", Clinical Chemistry 1993, 39, 2347-2348.

Cham, et al., "Rapid Regression of Atherosclerosis by Cholesterol Alpheresis—A Newly Developed Technique", 59th Congress European Atherosclerosis Society, Nice, France May 1992, 17-21 (Abstract only).

Cham, et al., "Rapid, Sensitive Method for the Separation of Free Cholesterol from Ester Cholesterol", Clinica Chimica Acta 1973, v. 49, 109-113.

Collet, et al., "Differential Effects of Lecithin and Cholesterol on the Immunoreactivity and Confirmation of Apolipoprotein A-I in High Density Lipoproteins", Journal of Biological Chemistry May 15, 1991, v. 266(14), 9145-9152.

Cooper, "Dietary Lipids in the Aetiology of Alzheimer's Disease: Implications for Therapy", Drugs Aging 2003, v. 20(6), 399-418 (Abstract only).

Highleyman, Liz "The Search for an HCV Vaccine", HCV Advocate Oct. 2003, monthly newsletter, vol. 6, Issue 10, pp. 1-9, http://www.hdvadvocate.org.

Hildreth, J.E.K. et al., "Solvent-Treated Retroviruses as Novel Vaccines—A Study in Characterizing Delipidated Retroviruses", Poster Presentation at Keystone Symposia on HIV Vaccine Development, Banff, Alberta, Canada. Apr. 9-15, 2005.

Horowitz, B. et al., "Viral safety of solvent/detergent-treated blood products", Blood Coagulation and Fibrinolysis 1994, vol. 5, Suppl. 3, pp. S21-S28.

Innerarity, et al., "Enhanced Binding by Cultured Human Fibroblasts of Apo-E Containing Lipoproteins as Compared with Low Density Lipoproteins", Biochemistry 1978, 17, 1449-1447.

Ito, J. et al., "Cholesterol-Sphingomyelin Interaction in Membrane and Apolproprotein-Medicated Cellular Cholesterol Efflux", J. of Lipid Research Jun. 2000, vol. 41, pp. 894-904.

Jackson, et al., "Isolation and Characterization of the Major Apolipoprotein from Chicken High Density Lipoproteins", Biochimica et Biophysica Acta 1976, v. 420, 342-349.

Kitabwalla, Moiz et al., "Delipidated Retroviruses as Potential Autologous Therapeutic Vaccines—A Pilot Experiment", Poster Presentation at Keystone Symposia on HIV Vaccine Development, Banff, Alberta, Canada. Apr. 9-15, 2005.

Kitabwalla, "Delipidated Retroviruses as Potential Therapeutic Vaccines—A Pilot Experiment", Experimental Biology and Medicine vol. 233 2008,, pp. 732-740.

Kitabwalla, Moiz et al., "Delipidated Retroviruses as Potential Autologus Therapeutic Vaccines—A Pilot Experiment", Oral presentation at Keystone Symposia on HIV Vaccine Development, Banff, Alberta, Canada. Apr. 9-15, 2005.

Kitabwalla, M. et al., "Enhancement of cell mediated immune responses using lipid depleted lentivirus as immunogen: a novel approach for inducing recognition of new viral epitopes", Vaccine May 31,2005, vol. 23, 4666-4677.

Klimov, A. N. et al., "Extraction of Lipids from Blood Plasma and Subsequent Introduction of Autologous Delipidized Plasma into the Body as a Possible Means to Treat Atherosclerosis", Russian Journal Kardiologia 1978, vol. 18, No. 6, pp. 23-29.

Koizumi, et al., "Behaviour of Human Apolipoprotein A-1: Phospho-Lipid and apoHDL: Phospholipid Complexes in Vitro and After Injection Into Rabbits", J. Lipid Research 1988, v. 29, 1405-1415.

Kostner, et al., "Increase of APO A1 Concentration in Hypercholesteraemic Chickens after Treatment with a Newly Developed Extracorpreal Lipid Elimination", XI Internet Symp. on Drugs Affecting Lipid Metabolism, Italy May 13, 1992.

Kostner, et al., "Lecithin-cholesterol acyltransferase activity in Normocholesterolaemic and Hypercholesterolaemic Roosters: Modulation by Lipid Apheresis", European Journal of Clinical Investigation May 7, 1997, v. 27, 212-218.

Koudinov, et al., "Alzheimer's Amyloid Beta Interaction with Normal Human Plasma High Density Lipoprotein: Association with Apolipoprotein and Lipids", Clin Chim Acta Feb. 23, 1999, v. 270(2), 75-84 (Abstract only).

Koudinov, et al., "Alzheimer's Soluble Amytoid Beta Protein is Secreted by HepG2 Cells as an Apolipoprotein", Cell Biol Int. May 1997, v. 21(5), 265-71, (Abstract only).

Koudinov, et al., "Biochemical Characterization of Alzheimer's Soluable Amytoid Beta Protein in Human Cerebrospinal Fluid: Association with High Density Lipoproteins", Biochem Biophys Res Commun Jun. 24, 1999, v. 223(3), 592-7, (Abstract only).

Koudinov, et al., "Cholesterol's Role in Synapse Formation", Science Nov. 9, 2001, v. 294, 2213.

Koudinova, et al., "Amytoid Beta, Neural Lipids, Cholesterol and Alzheimer's Disease", Neuroscience Abstract Viewer and Itinerary Planner 2002, Abstract 21.10.

Ksiazek, et al., "A Novel Coronavirus Associated with Severe Acute Respiratory Syndrome", N. Engl. J. Med May 15, 2003, 348:1953-1988.

Lipid Sciences, "Lipid Technology", http://www.lipidsciences.com/technology.html Aug. 25, 2001, 1-4.

Lupien, et al., "A New Approach to the Management of Familial Hypercholesterolaemia: Removal of Plasma-Cholesterol Based on the Principle of Affinity Chromatography", Lancet (LOS) 1976, 1, 1261-1265.

Mauch, et al., "CNS Synaptogenesis Promoted by Glia-Derived Cholesterol", Science Nov. 9, 2001, v. 294, 1354-1357.

Moya, et al., "A Cell Culture System for Screening Human Serum for Ability to Promote Cellular Cholesterold Efflux", Arteriosclerosis and Thrombosis Jul. 1994, 14(7), 1056-1065.

Neurath, A. R. et al., "Properties of Delipidated Hepatitis B Surface Antigen (HbsAAg) and Preparation of the Proteolytic Cleavage Fragments Carrying HbsAg-Specific Antigenic Determinants", Intervirology 1978, vol. 10 No. 5, pp. 265-275.

Ngu, V. A. "Chronic Infections from the Perspective of Evolution: a Hypothesis", Medical Hypothesis 1994, vol. 42, pp. 81-88.

Ngu, V. A. "Human Cancers and Viruses: A Hypothesis for Immune Destruction of Tumours Caused by Certain Enveloped Viruses Using Modified Viral Antigens", Medical Hypotheses 1992, vol. 39, pp. 17-21.

Sturman, Lawrence S. "Isolation of Coronavirus Envelope Glycoproteins and Interaction with the Viral Nucleocapsid", Journal of Virology Jan. 1980, vol. 33, No. 1, p. 449-462.

Wormser, Henry "Lipids", PSC3110—Fall Semester 2002.

Unpublished U.S. Appl. No. 12/203,551, filed Sep. 3, 2008.

Agnese, S. T. et al., "Evaluation of Four Reagents for Dilipidation of Serum", Clin Biochem 1983, vol. 18, No. 2, 98-100.

Albouz, et al., "Extraction of Plasma Lipids Preserving Antigenic Properties of Proteins and Allowing Quantiation of Gangliosides by Neuraminic Acid Determination", Biol. Clin. 1979, 37, 287-290 (Abstract only).

Andre, et al., "Characterization of Low- and Very-Low-Density Hepatitis C Virus RNA-Containing Particles", Journal of Virology Jul. 2002, 76(14), 6919-6928.

Aszlalos, et al., "Distribution of Apo A-I-Containing HDL Subpopulations in Patients with Coronary Heart Disease", Arterlosclr. Thromb. Vasc. Biol. Dec. 1, 2000, 2670-2676.

Aszlalos, et al., "Presence and Formation of 'Free Apoliprotein A-I-Like' Particles in Human Plasma", Arterloscler. Thromb. Vasc. Biol. 1995, 15, 1419-1423.

Aszlalos, et al., "Role of Free Apolipoprotein A-I in Cholesterol Efflux", Arterloscler. Thromb. Vasc Biol. 1997, 17, 1630/1636.

Badimon, et al., "High Density Lipoprotein Plasma Fractions Inhibit Aortic Fatty Streaks in Cholesterol-Fed Rabbits", Laboratory Investigation 1989, 60, 455-461.

Badimon, et al., "Regression of Atherosclerotic Lesions by High Density Lipoprotein Plasma Fraction in the Cholesterol-Fed Rabbit", J. Clinical Investigation 1990, 85, 1234-1241.

Barbara, J. "The Rationale for Pathogen-Inactivation Treatment of Blood Components", International Journal of Hematology 2004, 80, pp. 311-316.

Barouch, D. H. et al., "Eventual AIDS vaccine failure in a rhesus monkey by viral escape from cytotoxic T lymphocytes", Nature 2002, 415, pp. 335-339.

Barrans, et al., "Pre-Beta HDL: Structure and Metabolism", Biochimica et Biophysica Acta 1996, v. 1300, pp. 73-85.

Barres, et al., "Cholesterol—Making or Breaking he Synapse", Science Nov. 9, 2001, v. 294, 1296/1297.

Bloom, et al., "Quantitation of lipid profiles from isolated serum lipoproteinsn using small volumes of human serum", Clin. Biochem. Jun. 1981, v. 14, 119-125 (Abstract only).

Buckwold, V. E. et al., "Bovine viral diarrhea virus as a surrogate model of Hepatitis C virus for the evaluation of antiviral agents", Antiviral Research 2003, 60:1-15.

Cruzado, et al., "Characterization and Quantitation of the Apoproteins of High-Density Lipoprotein by Capillary Electrophoresis", Analytical Biochemistry 1996, 17(7), 100-109.

Czerkinsky, Cecil C. "A Solid-Phase Enzyme-Linked Immunospot (ELISPOT) Assay for Enumeration of Specific Antibody-Secreting Cells", Journal of Immunological Methods 1983, 65:109-121.

Davenport, F. M. et al., "Comparisons of Serologic and Febrile Responses in Humans to Vaccination with Influenza A Viruses and Their Hemagglutinins", J. Lab. Clin. Med. 1964, 63:5-13.

Desombere, I et al., "Partial delipidation improves the T-cell antigenicity of Hepatis B virus surface antigen", Journal of Virology 80 2006, 3506-3514.

Desrosiers, R. C. "Prospects for an AIDS vaccine", Nature Medicine Mar. 2004, 10(3), 221-223.

Deva, A. K. et al., "Establishment of an in-use testing method for evaluating disinfection of surgical instruments using the duck hepatitis B model", J. Hosp. Infect. 1996, vol. 22, No. 2, pp. 119-130 (Abstract only).

Dwivedy, "Increase of Reverse Cholesterol Transport by Cholesterol Apheresis Regression of Atherosclerosis", 18th Australian Atherosclerosis Society Conference, Surfers Paradise 1992, 21.

Eisenhauer, et al., "Selective Removal of Low Density Lipoproteins (LDL) by Precipitation at Low pH: First Clinical Application of the HELP System", Klin Wochenschr (KWH) 1987, 65, 161-168.

Fang, et al., "In Vivo Rapid Mobilization of Adipose Tissue by Lipid Apheresis—A Newly Developed Technique", 18th Australian Atherosclerosis Society Conference, Gold Coast, Australia 1992.

Feinberg, et al., "AIDS vaccine models: Challenging challenge viruses", Nature Medicine Mar. 2002, 8(3):207-210.

Feinstone, Stephen M. et al., "Inactivation of Hepatitis B Virus and Non-A, Non-B Hepatitis by Chloroform", Infection and Immunity Aug. 1983, vol. 41, No. 2, pp. 816-821.

Golde, et al., "Cholesterol Modulation as an Emerging Strategy for the Treatment of Alzheimer's Disease", Drug Discovery Today Oct. 15, 2001, 6(20), 1049-1055 (Abstract only).

Han, Dong P. et al., "Development of a safe neutralization assay for SARS-CoV and characterization of S-glycoprotein", Virology 2004, 326:140-149.

Hatch, et al., "Advances in Lipid Research, Practical Methods for Plasma Lipoprotein Analysis", Lipoprotein Analysis 1968, 6, 1-68.

Ngu, V. A. "The viral envelope in the evolution of HIV: a hypothetical approach to inducing an effective immune response to the virus", Medical Hypotheses 1997, vol. 48, pp. 517-521.

Offit, Paul A. et al., "Noninfectious Rotavirus (Strain RRV) Induces an Immune Response in Mice Which Protects against Rotavirus Challenge", Journal of Clinical Microbiology May 1989, v. 27, No. 5, 885-888.

Okazaki, et al., "Improved High-Performance Liquid Chromatographic Method for the Determination of Apolopoproteins in Serum High-Density Lipoproteins", Journal of Chromatography, Biomedical Applications 1988, v. 430, 135-142.

Parker, Thomas S. et al., "Plasma high density lipoprotein is increased in man when low density lipoprotein (LDL) is lowered by LDL-pheresis", Proc. Natl. Acad. Sci. USA Feb. 1986, vol. 82, pp. 771-781.

Paterno, et al., "Reconstituted High-Density Lipoprotein Exhibits Neuroprotection in Two Rat Models of Stroke", Cerebrovasc Dis. Epub Dec. 29, 2003, 17, 2-2, 204-11(Abstract only).

Perrin, P et al., "Inactivation of DNA by beta-propiolactone", Bilogicals 3 1995, 207-11.

Refolo, et al., "Cholesterol Metabolism: A Potential Target for Alzheimer's Disease Therapy", Neuroscience Abstracts 2001, 27(2), 1518, (Abstract only).

Robern, et al., "The Application of Sodium Deoxycholate and Sephacryl-200 for the Delipidation and Separation of High Density Lipoproteins", Experientia 1982, 38, 437-439.

Ryan, et al., "An improved Extraction Procedure for the Determination of Triglycerides and Cholesterol in Plasma or Serum", Clinical Chemistry 1967, 13, 769-772.

Scanu, et al., "Solubility in Aqueous Solutions of Ethanol of the Small Molecular Weight Peptides of the Serum Very Low Density and High Density Lipoproteins: Relevance to the Recovery Problem During Delipidation of Serum Lipoproteins", Anallytical Biochemistry 1971, 44, 576-588.

Segrest, et al., "A Detailed Molecular Belt Model for Apolipoprotein A-I in Discoidal High Density Lipoprotein", Journal of Biological Chemistry Nov. 5, 1999, 274(45), 31755-31758.

Slater, et al., "A Comparison of Delipidated Sera Used in Studies of Sterol Synthesis by Human Mononuclear Leukocytes", J. of Lipid Research 1979, v. 20, 413-416.

Slater, et al., "The Effect of Delipidated High Density Lipoprotein on Human Leukocyte Sterol Synthesis", Atherosclerosis 1980, 35, 41-49.

Strickland, G. T. et al., "Hepatitis C Vaccine: Supply and demand", Lancet Infect. Dis. 2008, vol. 8, 379-386.

Sturman, Lawrence S. "Isolation of Coronavirus Envelope Glycoproteins and Interaction with the Viral Nucleocapsid", Journal of Virology Jan. 1980, vol. 33, No. 1, pp. 449-462.

Thompson, et al., "Plasma Exchange in the Management of Homozygous Familial Hypercholesterolaemia", Lancet (LOS) 1975, 1, 1208-1211.

U.S. Department of Health, and Human Services "Occupational Safety and Health Guideline for beta-propiolactone potential human carcinogen", available from http://origin.cdc.gov/niosh/docs/81-123/pdfs/0528.pdf 1998, pp. 1-6.

Walker, et al., "Escape from Immune System", Nature 2000, v. 407, pp. 313-134.

Williams, et al., "Low Density Lipoprotein Receptor-independent Hepatic Uptake of a Synthetic, Cholesterol-Scavenging Lipoprotein: Implications for the Treatment of Receptor-Deficient Atherosclerosis", Proc. Natl. Acad. Scci. USA 1988, 85:242-246.

Williams, et al., "Uptake of Endogenous Cholesterol by a Synthetic Lipoprotein", Biochim. Biophys. Act. Feb. 12, 1986, v. 875(2), 183-194.

Wong, et al., "Retention of gangliosides in serium delipidated by diisopropyl ether-1-butanol extraction", Journal of Lipid Research 1983, v. 24, 666-669.

Wormser, Henry "Lipids", PSC3110—Fall Semester 2002 2002.

Yokoyama, et al., "Selective Removal of Low Density Lipoprotein by Plasmapheresis in Familial Hypercholesterolemia", Arteriosclerosis 1985, v. 5, 613-622.

Yoshidome, et al., "Serum Amyloid A andn P Protein Levels are Lowered by Dextran Sulfate Cellulose Low-Density Lipoprotein Apheresis", Artif Organs 1998, 22(2), 144-148.

Zetia, http://www/zetia.com/ezetimbe/zetia/hcp/product_highlights/index.jsp, Zetia (ezetimibe) Jul. 18, 2003, 1-2.

Zetia, "Zetia: Compliments Statin with a Unique Mechanism", http://www.zetia.com/ezetimibe/zetia.hcp/mechanism_of_action/index.jsp Jul. 18, 2003, 1-2.

Zhang, et al., "Characterization of phospholipids in a pre-alpha HDL: Selective Phospholipid Efflux with Apolipoprotein A-I", Journal of Lipid Research 1998, 39, 1601-1607.

* cited by examiner

Direct magnification=13000X

Direct magnification=23000X

SARS peptide pools generated and used for the ELISPOT assay

| N.C. | 1 | 2 | 3 | 4 | 5 | 6 | 7 |
|---|---|---|---|---|---|---|---|
| 8 | 9539 | 9540 | 9541 | 9542 | 9543 | 9544 | 9545 |
| 9 | 9546 | 9547 | 9548 | 9549 | 9550 | 9551 | 9552 |
| 10 | 9553 | 9554 | 9555 | 9556 | 9557 | 9558 | 9559 |
| 11 | 9560 | 9561 | 9562 | 9563 | 9564 | 9565 | 9566 |
| 12 | 9567 | 9569 | 9570 | 9571 | 9572 | 9573 | 9574 |
| 13 | 9575 | 9576 | 9577 | 9578 | 9579 | 9580 | 9581 |
| 14 | 9582 | 9583 | 9584 | 9585 | 9586 | 9587 | 9588 |
| 15 | 9589 | 9590 | 9591 | 9592 | 9594 | 9595 | |

| SPIKE | 1 | 2 | 3 | 4 | 5 | 6 | 7 | 8 | 9 | 10 | 11 | 12 |
|---|---|---|---|---|---|---|---|---|---|---|---|---|
| 13 | 9597 | 9598 | 9599 | 9601 | 9602 | 9603 | 9604 | 9605 | 9606 | 9607 | 9608 | 9609 |
| 14 | 9610 | 9611 | 9612 | 9614 | 9615 | 9616 | 9619 | 9620 | 9621 | 9622 | 9623 | 9624 |
| 15 | 9625 | 9626 | 9627 | 9628 | 9629 | 9631 | 9632 | 9633 | 9634 | 9636 | 9637 | 9638 |
| 16 | 9639 | 9640 | 9641 | 9642 | 9643 | 9644 | 9645 | 9646 | 9647 | 9648 | 9649 | 9650 |
| 17 | 9651 | 9652 | 9653 | 9655 | 9656 | 9657 | 9658 | 9659 | 9660 | 9661 | 9663 | 9665 |
| 18 | 9666 | 9667 | 9668 | 9669 | 9670 | 9671 | 9672 | 9673 | 9674 | 9675 | 9676 | 9678 |
| 19 | 9679 | 9680 | 9681 | 9682 | 9684 | 9685 | 9686 | 9687 | 9688 | 9689 | 9690 | 9691 |
| 20 | 9692 | 9694 | 9697 | 9698 | 9699 | 9700 | 9701 | 9702 | 9703 | 9704 | 9705 | 9706 |
| 21 | 9707 | 9708 | 9709 | 9710 | 9711 | 9713 | 9715 | 9716 | 9718 | 9719 | 9721 | 9723 |
| 22 | 9725 | 9727 | 9728 | 9731 | 9732 | 9733 | 9734 | 9735 | 9736 | 9737 | 9738 | 9739 |
| 23 | 9740 | 9741 | 9742 | 9743 | 9744 | 9745 | 9748 | 9749 | 9750 | 9751 | 9752 | 9753 |
| 24 | 9754 | 9755 | 9756 | 9757 | 9758 | 9759 | 9760 | 9761 | 9762 | 9763 | 9764 | 9765 |

SEQUENCE LISTING

<160> NUMBER OF SEQ ID NOS: 199

<210> SEQ ID NO 1
<211> LENGTH: 16
<212> TYPE: PRT
<213> ORGANISM: Artificial Sequence
<220> FEATURE:
<223> OTHER INFORMATION: Note:  Artificial = synthetic construct

```
<400> SEQUENCE: 1

Met Ser Asp Asn Gly Pro Gln Ser Asn Gln Arg Ser Ala Pro Arg Ile
1               5                   10                  15

<210> SEQ ID NO 2
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 2

Gln Ser Asn Gln Arg Ser Ala Pro Arg Ile Thr Phe Gly Gly Pro Thr
1               5                   10                  15

Asp Ser

<210> SEQ ID NO 3
<211> LENGTH: 19
<212> TYPE: PRT
<213> ORGANISM: Artificial Sequence
<220> FEATURE:
<223> OTHER INFORMATION: Note:   Artificial = synthetic construct

<400> SEQUENCE: 3

Arg Ile Thr Phe Gly Gly Pro Thr Asp Ser Thr Asp Asn Asn Gln Asn
1               5                   10                  15

Gly Gly Arg

<210> SEQ ID NO 4
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 4

Ser Thr Asp Asn Asn Gln Asn Gly Gly Arg Asn Gly Ala Arg Pro Lys
1               5                   10                  15

Gln Arg

<210> SEQ ID NO 5
<211> LENGTH: 15
<212> TYPE: PRT
<213> ORGANISM: Artificial Sequence
<220> FEATURE:
<223> OTHER INFORMATION: Note:   Artificial = synthetic construct

<400> SEQUENCE: 5

Gly Arg Asn Gly Ala Arg Pro Lys Gln Arg Arg Pro Gln Gly Leu
1               5                   10                  15

<210> SEQ ID NO 6
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 6

Arg Pro Lys Gln Arg Arg Pro Gln Gly Leu Pro Asn Asn Thr Ala Ser
1               5                   10                  15

Trp Phe
```

```
<210> SEQ ID NO 7
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 7

Gly Leu Pro Asn Asn Thr Ala Ser Trp Phe Thr Ala Leu Thr Gln His
1               5                   10                  15

Gly Lys

<210> SEQ ID NO 8
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 8

Trp Phe Thr Ala Leu Thr Gln His Gly Lys Glu Glu Leu Arg Phe Pro
1               5                   10                  15

Arg

<210> SEQ ID NO 9
<211> LENGTH: 16
<212> TYPE: PRT
<213> ORGANISM: Artificial Sequence
<220> FEATURE:
<223> OTHER INFORMATION: Note:   Artificial = synthetic construct

<400> SEQUENCE: 9

His Gly Lys Glu Glu Leu Arg Phe Pro Arg Gly Gln Gly Val Pro Ile
1               5                   10                  15

<210> SEQ ID NO 10
<211> LENGTH: 20
<212> TYPE: PRT
<213> ORGANISM: Artificial Sequence
<220> FEATURE:
<223> OTHER INFORMATION: Note:   Artificial = synthetic construct

<400> SEQUENCE: 10

Arg Phe Pro Arg Gly Gln Gly Val Pro Ile Asn Thr Asn Ser Gly Pro
1               5                   10                  15

Asp Asp Gln Ile
            20

<210> SEQ ID NO 11
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 11

Asn Thr Asn Ser Gly Pro Asp Asp Gln Ile Gly Tyr Tyr Arg Arg Ala
1               5                   10                  15

Thr Arg

<210> SEQ ID NO 12
<211> LENGTH: 18
<212> TYPE: PRT
<213> ORGANISM: Artificial Sequence
<220> FEATURE:
<223> OTHER INFORMATION: Note:   Artificial = synthetic construct
```

```
<400> SEQUENCE: 12

Gln Ile Gly Tyr Tyr Arg Arg Ala Thr Arg Arg Val Arg Gly Gly Asp
1               5                   10                  15

Gly Lys

<210> SEQ ID NO 13
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 13

Thr Arg Arg Val Arg Gly Gly Asp Gly Lys Met Lys Glu Leu Ser Pro
1               5                   10                  15

Arg Trp

<210> SEQ ID NO 14
<211> LENGTH: 15
<212> TYPE: PRT
<213> ORGANISM: Artificial Sequence
<220> FEATURE:
<223> OTHER INFORMATION: Note:  Artificial = synthetic construct

<400> SEQUENCE: 14

Gly Lys Met Lys Glu Leu Ser Pro Arg Trp Tyr Phe Tyr Tyr Leu
1               5                   10                  15

<210> SEQ ID NO 15
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 15

Leu Ser Pro Arg Trp Tyr Phe Tyr Tyr Leu Gly Thr Gly Pro Glu Ala
1               5                   10                  15

Ser Leu

<210> SEQ ID NO 16
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 16

Tyr Leu Gly Thr Gly Pro Glu Ala Ser Leu Pro Tyr Gly Ala Asn Lys
1               5                   10                  15

<210> SEQ ID NO 17
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 17

Glu Ala Ser Leu Pro Tyr Gly Ala Asn Lys Glu Gly Ile Val Trp Val
1               5                   10                  15

Ala
```

```
<210> SEQ ID NO 18
<211> LENGTH: 15
<212> TYPE: PRT
<213> ORGANISM: Artificial Sequence
<220> FEATURE:
<223> OTHER INFORMATION: Note:  Artificial = synthetic construct

<400> SEQUENCE: 18

Ala Asn Lys Glu Gly Ile Val Trp Val Ala Thr Glu Gly Ala Leu
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 19

Ile Val Trp Val Ala Thr Glu Gly Ala Leu Asn Thr Pro Lys Asp His
1               5                   10                  15

Ile

<210> SEQ ID NO 20
<211> LENGTH: 19
<212> TYPE: PRT
<213> ORGANISM: Artificial Sequence
<220> FEATURE:
<223> OTHER INFORMATION: Note:  Artificial = synthetic construct

<400> SEQUENCE: 20

Gly Ala Leu Asn Thr Pro Lys Asp His Ile Gly Thr Arg Asn Pro Asn
1               5                   10                  15

Asn Asn Ala

<210> SEQ ID NO 21
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 21

Ile Gly Thr Arg Asn Pro Asn Asn Asn Ala Ala Thr Val Leu Gln Leu
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 22

Asn Asn Asn Ala Ala Thr Val Leu Gln Leu Pro Gln Gly Thr Thr Leu
1               5                   10                  15

Pro Lys

<210> SEQ ID NO 23
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 23
```

Gln Leu Pro Gln Gly Thr Thr Leu Pro Lys Gly Phe Tyr Ala Glu Gly
1               5                   10                  15

Ser Arg

<210> SEQ ID NO 24
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 24

Pro Lys Gly Phe Tyr Ala Glu Gly Ser Arg Gly Gly Ser Gln Ala Ser
1               5                   10                  15

Ser Arg

<210> SEQ ID NO 25
<211> LENGTH: 16
<212> TYPE: PRT
<213> ORGANISM: Artificial Sequence
<220> FEATURE:
<223> OTHER INFORMATION: Note:   Artificial = synthetic construct

<400> SEQUENCE: 25

Ser Arg Gly Gly Ser Gln Ala Ser Ser Arg Ser Ser Ser Arg Ser Arg
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 26

Ala Ser Ser Arg Ser Ser Ser Arg Ser Arg Gly Asn Ser Arg Asn Ser
1               5                   10                  15

Thr

<210> SEQ ID NO 27
<211> LENGTH: 15
<212> TYPE: PRT
<213> ORGANISM: Artificial Sequence
<220> FEATURE:
<223> OTHER INFORMATION: Note:   Artificial = synthetic construct

<400> SEQUENCE: 27

Arg Ser Arg Gly Asn Ser Arg Asn Ser Thr Pro Gly Ser Ser Arg
1               5                   10                  15

<210> SEQ ID NO 28
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 28

Ser Arg Asn Ser Thr Pro Gly Ser Ser Arg Gly Asn Ser Pro Ala Arg
1               5                   10                  15

Met Ala

<210> SEQ ID NO 29
<211> LENGTH: 18
<212> TYPE: PRT

```
<213> ORGANISM: Artificial Sequence
<220> FEATURE:
<223> OTHER INFORMATION: Note:   Artificial = synthetic construct

<400> SEQUENCE: 29

Ser Arg Gly Asn Ser Pro Ala Arg Met Ala Ser Gly Gly Gly Glu Thr
1               5                   10                  15

Ala Leu

<210> SEQ ID NO 30
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 30

Ala Leu Ala Leu Leu Leu Leu Asp Arg Leu Asn Gln Leu Glu Ser Lys
1               5                   10                  15

Val

<210> SEQ ID NO 31
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 31

Asp Arg Leu Asn Gln Leu Glu Ser Lys Val Ser Gly Lys Gly Gln Gln
1               5                   10                  15

Gln Gln

<210> SEQ ID NO 32
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 32

Lys Val Ser Gly Lys Gly Gln Gln Gln Gly Gln Thr Val Thr Lys
1               5                   10                  15

Lys

<210> SEQ ID NO 33
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 33

Gln Gln Gln Gly Gln Thr Val Thr Lys Lys Ser Ala Ala Glu Ala Ser
1               5                   10                  15

Lys Lys

<210> SEQ ID NO 34
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 34
```

```
Lys Lys Ser Ala Ala Glu Ala Ser Lys Lys Pro Arg Gln Lys Arg Thr
1               5                   10                  15

Ala

<210> SEQ ID NO 35
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 35

Ser Lys Lys Pro Arg Gln Lys Arg Thr Ala Thr Lys Gln Tyr Asn Val
1               5                   10                  15

<210> SEQ ID NO 36
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 36

Lys Arg Thr Ala Thr Lys Gln Tyr Asn Val Thr Gln Ala Phe Gly Arg
1               5                   10                  15

Arg

<210> SEQ ID NO 37
<211> LENGTH: 19
<212> TYPE: PRT
<213> ORGANISM: Artificial Sequence
<220> FEATURE:
<223> OTHER INFORMATION: Note:  Artificial = synthetic construct

<400> SEQUENCE: 37

Tyr Asn Val Thr Gln Ala Phe Gly Arg Arg Gly Pro Glu Gln Thr Gln
1               5                   10                  15

Gly Asn Phe

<210> SEQ ID NO 38
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 38

Arg Gly Pro Glu Gln Thr Gln Gly Asn Phe Gly Asp Gln Asp Leu Ile
1               5                   10                  15

Arg

<210> SEQ ID NO 39
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 39

Gly Asn Phe Gly Asp Gln Asp Leu Ile Arg Gln Gly Thr Asp Tyr Lys
1               5                   10                  15

His Trp
```

```
<210> SEQ ID NO 40
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 40

Ile Arg Gln Gly Thr Asp Tyr Lys His Trp Pro Gln Ile Ala Gln Phe
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 41

Lys His Trp Pro Gln Ile Ala Gln Phe Ala Pro Ser Ala Ser Ala Phe
1               5                   10                  15

Phe

<210> SEQ ID NO 42
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 42

Gln Phe Ala Pro Ser Ala Ser Ala Phe Phe Gly Met Ser Arg Ile Gly
1               5                   10                  15

Met

<210> SEQ ID NO 43
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 43

Ala Phe Phe Gly Met Ser Arg Ile Gly Met Glu Val Thr Pro Ser Gly
1               5                   10                  15

Thr Trp

<210> SEQ ID NO 44
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 44

Gly Met Glu Val Thr Pro Ser Gly Thr Trp Leu Thr Tyr His Gly Ala
1               5                   10                  15

Ile Lys

<210> SEQ ID NO 45
<211> LENGTH: 18
<212> TYPE: PRT
<213> ORGANISM: Artificial Sequence
<220> FEATURE:
```

<223> OTHER INFORMATION: Note:  Artificial = synthetic construct

<400> SEQUENCE: 45

Thr Trp Leu Thr Tyr His Gly Ala Ile Lys Leu Asp Asp Lys Asp Pro
1               5                   10                  15

Gln Phe

<210> SEQ ID NO 46
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 46

Ile Lys Leu Asp Asp Lys Asp Pro Gln Phe Lys Asp Asn Val Ile Leu
1               5                   10                  15

Leu

<210> SEQ ID NO 47
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 47

Pro Gln Phe Lys Asp Asn Val Ile Leu Leu Asn Lys His Ile Asp Ala
1               5                   10                  15

Tyr Lys

<210> SEQ ID NO 48
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 48

Leu Leu Asn Lys His Ile Asp Ala Tyr Lys Thr Phe Pro Pro Thr Glu
1               5                   10                  15

Pro Lys

<210> SEQ ID NO 49
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 49

Tyr Lys Thr Phe Pro Pro Thr Glu Pro Lys Lys Asp Lys Lys Lys Lys
1               5                   10                  15

<210> SEQ ID NO 50
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 50

Thr Glu Pro Lys Lys Asp Lys Lys Lys Lys Thr Asp Glu Ala Gln Pro
1               5                   10                  15

Leu

<210> SEQ ID NO 51
<211> LENGTH: 16
<212> TYPE: PRT
<213> ORGANISM: Artificial Sequence
<220> FEATURE:
<223> OTHER INFORMATION: Note: Artificial = synthetic construct

<400> SEQUENCE: 51

Lys Lys Lys Thr Asp Glu Ala Gln Pro Leu Pro Gln Arg Gln Lys Lys
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 52

Ala Gln Pro Leu Pro Gln Arg Gln Lys Lys Gln Pro Thr Val Thr Leu
1               5                   10                  15

Leu

<210> SEQ ID NO 53
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 53

Gln Lys Lys Gln Pro Thr Val Thr Leu Leu Pro Ala Ala Asp Met Asp
1               5                   10                  15

Asp Phe

<210> SEQ ID NO 54
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 54

Leu Leu Pro Ala Ala Asp Met Asp Asp Phe Ser Arg Gln Leu Gln Asn
1               5                   10                  15

Ser Met

<210> SEQ ID NO 55
<211> LENGTH: 15
<212> TYPE: PRT
<213> ORGANISM: Artificial Sequence
<220> FEATURE:
<223> OTHER INFORMATION: Note: Artificial = synthetic construct

<400> SEQUENCE: 55

Asp Phe Ser Arg Gln Leu Gln Asn Ser Met Ser Gly Ala Ser Ala
1               5                   10                  15

<210> SEQ ID NO 56
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 56

Met Phe Ile Phe Leu Leu Phe Leu Thr Leu Thr Ser Gly Ser Asp Leu
1               5                   10                  15

Asp Arg

<210> SEQ ID NO 57
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 57

Thr Leu Thr Ser Gly Ser Asp Leu Asp Arg Cys Thr Thr Phe Asp Asp
1               5                   10                  15

Val

<210> SEQ ID NO 58
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 58

Leu Asp Arg Cys Thr Thr Phe Asp Asp Val Gln Ala Pro Asn Tyr Thr
1               5                   10                  15

Gln His

<210> SEQ ID NO 59
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 59

Gln His Thr Ser Ser Met Arg Gly Val Tyr Tyr Pro Asp Glu Ile Phe
1               5                   10                  15

Arg

<210> SEQ ID NO 60
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 60

Gly Val Tyr Tyr Pro Asp Glu Ile Phe Arg Ser Asp Thr Leu Tyr Leu
1               5                   10                  15

<210> SEQ ID NO 61
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 61

Glu Ile Phe Arg Ser Asp Thr Leu Tyr Leu Thr Gln Asp Leu Phe Leu
1               5                   10                  15

Pro Phe

<210> SEQ ID NO 62
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 62

Tyr Leu Thr Gln Asp Leu Phe Leu Pro Phe Tyr Ser Asn Val Thr Gly
1               5                   10                  15

Phe His

<210> SEQ ID NO 63
<211> LENGTH: 16
<212> TYPE: PRT
<213> ORGANISM: Artificial Sequence
<220> FEATURE:
<223> OTHER INFORMATION: Note: Artificial = synthetic construct

<400> SEQUENCE: 63

Pro Phe Tyr Ser Asn Val Thr Gly Phe His Thr Ile Asn His Thr Phe
1               5                   10                  15

<210> SEQ ID NO 64
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 64

Thr Gly Phe His Thr Ile Asn His Thr Phe Gly Asn Pro Val Ile Pro
1               5                   10                  15

Phe Lys

<210> SEQ ID NO 65
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 65

Thr Phe Gly Asn Pro Val Ile Pro Phe Lys Asp Gly Ile Tyr Phe Ala
1               5                   10                  15

Ala

<210> SEQ ID NO 66
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 66

Pro Phe Lys Asp Gly Ile Tyr Phe Ala Ala Thr Glu Lys Ser Asn Val
1               5                   10                  15

Val Arg

<210> SEQ ID NO 67
<211> LENGTH: 18
<212> TYPE: PRT
<213> ORGANISM: Artificial Sequence
<220> FEATURE:

```
<223> OTHER INFORMATION: Note:   Artificial = synthetic construct

<400> SEQUENCE: 67

Ala Ala Thr Glu Lys Ser Asn Val Val Arg Gly Trp Val Phe Gly Ser
1               5                   10                  15

Thr Met

<210> SEQ ID NO 68
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 68

Val Arg Gly Trp Val Phe Gly Ser Thr Met Asn Asn Lys Ser Gln Ser
1               5                   10                  15

Val Ile

<210> SEQ ID NO 69
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 69

Thr Met Asn Asn Lys Ser Gln Ser Val Ile Ile Ile Asn Asn Ser Thr
1               5                   10                  15

Asn Val

<210> SEQ ID NO 70
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 70

Val Ile Ile Ile Asn Asn Ser Thr Asn Val Val Ile Arg Ala Cys Asn
1               5                   10                  15

Phe

<210> SEQ ID NO 71
<211> LENGTH: 16
<212> TYPE: PRT
<213> ORGANISM: Artificial Sequence
<220> FEATURE:
<223> OTHER INFORMATION: Note:   Artificial = synthetic construct

<400> SEQUENCE: 71

Asn Phe Glu Leu Cys Asp Asn Pro Phe Phe Ala Val Ser Lys Pro Met
1               5                   10                  15

<210> SEQ ID NO 72
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 72

Asn Pro Phe Phe Ala Val Ser Lys Pro Met Gly Thr Gln Thr His Thr
1               5                   10                  15
```

Met Ile

<210> SEQ ID NO 73
<211> LENGTH: 15
<212> TYPE: PRT
<213> ORGANISM: Artificial Sequence
<220> FEATURE:
<223> OTHER INFORMATION: Note: Artificial = synthetic construct

<400> SEQUENCE: 73

Pro Met Gly Thr Gln Thr His Thr Met Ile Phe Asp Asn Ala Phe
1               5                   10                  15

<210> SEQ ID NO 74
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 74

Tyr Ile Ser Asp Ala Phe Ser Leu Asp Val Ser Glu Lys Ser Gly Asn
1               5                   10                  15

Phe Lys

<210> SEQ ID NO 75
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 75

Asp Val Ser Glu Lys Ser Gly Asn Phe Lys His Leu Arg Glu Phe Val
1               5                   10                  15

Phe Lys

<210> SEQ ID NO 76
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 76

Phe Lys His Leu Arg Glu Phe Val Phe Lys Asn Lys Asp Gly Phe Leu
1               5                   10                  15

Tyr Val

<210> SEQ ID NO 77
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 77

Phe Lys Asn Lys Asp Gly Phe Leu Tyr Val Tyr Lys Gly Tyr Gln Pro
1               5                   10                  15

Ile

<210> SEQ ID NO 78
<211> LENGTH: 16
<212> TYPE: PRT
<213> ORGANISM: Artificial Sequence

```
-continued

<220> FEATURE:
<223> OTHER INFORMATION: Note:  Artificial = synthetic construct

<400> SEQUENCE: 78

Leu Tyr Val Tyr Lys Gly Tyr Gln Pro Ile Asp Val Val Arg Asp Leu
1               5                   10                  15

<210> SEQ ID NO 79
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 79

Tyr Gln Pro Ile Asp Val Val Arg Asp Leu Pro Ser Gly Phe Asn Thr
1               5                   10                  15

Leu Lys

<210> SEQ ID NO 80
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 80

Asp Leu Pro Ser Gly Phe Asn Thr Leu Lys Pro Ile Phe Lys Leu Pro
1               5                   10                  15

Leu

<210> SEQ ID NO 81
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 81

Thr Leu Lys Pro Ile Phe Lys Leu Pro Leu Gly Ile Asn Ile Thr Asn
1               5                   10                  15

Phe Arg

<210> SEQ ID NO 82
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 82

Pro Leu Gly Ile Asn Ile Thr Asn Phe Arg Ala Ile Leu Thr Ala Phe
1               5                   10                  15

<210> SEQ ID NO 83
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 83

Thr Asn Phe Arg Ala Ile Leu Thr Ala Phe Ser Pro Ala Gln Asp Ile
1               5                   10                  15

Trp
```

-continued

```
<210> SEQ ID NO 84
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 84

Thr Ala Phe Ser Pro Ala Gln Asp Ile Trp Gly Thr Ser Ala Ala Ala
1               5                   10                  15

Tyr Phe

<210> SEQ ID NO 85
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 85

Ala Ala Ala Tyr Phe Val Gly Tyr Leu Lys Pro Thr Thr Phe Met Leu
1               5                   10                  15

Lys Tyr

<210> SEQ ID NO 86
<211> LENGTH: 16
<212> TYPE: PRT
<213> ORGANISM: Artificial Sequence
<220> FEATURE:
<223> OTHER INFORMATION: Note:   Artificial = synthetic construct

<400> SEQUENCE: 86

Leu Lys Pro Thr Thr Phe Met Leu Lys Tyr Asp Glu Asn Gly Thr Ile
1               5                   10                  15

<210> SEQ ID NO 87
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 87

Met Leu Lys Tyr Asp Glu Asn Gly Thr Ile Thr Asp Ala Val Asp Cys
1               5                   10                  15

Ser Gln

<210> SEQ ID NO 88
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 88

Thr Ile Thr Asp Ala Val Asp Cys Ser Gln Asn Pro Leu Ala Glu Leu
1               5                   10                  15

Lys

<210> SEQ ID NO 89
<211> LENGTH: 15
<212> TYPE: PRT
<213> ORGANISM: Artificial Sequence
<220> FEATURE:
```

```
<223> OTHER INFORMATION: Note:  Artificial = synthetic construct

<400> SEQUENCE: 89

Leu Lys Cys Ser Val Lys Ser Phe Glu Ile Asp Lys Gly Ile Tyr
1               5                   10                  15

<210> SEQ ID NO 90
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 90

Lys Ser Phe Glu Ile Asp Lys Gly Ile Tyr Gln Thr Ser Asn Phe Arg
1               5                   10                  15

Val Val

<210> SEQ ID NO 91
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 91

Ile Tyr Gln Thr Ser Asn Phe Arg Val Val Pro Ser Gly Asp Val Val
1               5                   10                  15

Arg Phe

<210> SEQ ID NO 92
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 92

Val Val Pro Ser Gly Asp Val Val Arg Phe Pro Asn Ile Thr Asn Leu
1               5                   10                  15

<210> SEQ ID NO 93
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 93

Val Val Arg Phe Pro Asn Ile Thr Asn Leu Cys Pro Phe Gly Glu Val
1               5                   10                  15

Phe

<210> SEQ ID NO 94
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 94

Thr Asn Leu Cys Pro Phe Gly Glu Val Phe Asn Ala Thr Lys Phe Pro
1               5                   10                  15

Ser Val
```

```
<210> SEQ ID NO 95
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 95

Val Phe Asn Ala Thr Lys Phe Pro Ser Val Tyr Ala Trp Glu Arg Lys
1               5                   10                  15

Lys Ile

<210> SEQ ID NO 96
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 96

Ser Val Tyr Ala Trp Glu Arg Lys Lys Ile Ser Asn Cys Val Ala Asp
1               5                   10                  15

Tyr

<210> SEQ ID NO 97
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 97

Lys Lys Ile Ser Asn Cys Val Ala Asp Tyr Ser Val Leu Tyr Asn Ser
1               5                   10                  15

Thr Phe

<210> SEQ ID NO 98
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 98

Asp Tyr Ser Val Leu Tyr Asn Ser Thr Phe Phe Ser Thr Phe Lys Cys
1               5                   10                  15

Tyr

<210> SEQ ID NO 99
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 99

Ser Thr Phe Phe Ser Thr Phe Lys Cys Tyr Gly Val Ser Ala Thr Lys
1               5                   10                  15

Leu

<210> SEQ ID NO 100
<211> LENGTH: 18
<212> TYPE: PRT
<213> ORGANISM: Artificial Sequence
```

```
<220> FEATURE:
<223> OTHER INFORMATION: Note: Artificial = synthetic construct

<400> SEQUENCE: 100

Lys Cys Tyr Gly Val Ser Ala Thr Lys Leu Asn Asp Leu Cys Phe Ser
1               5                   10                  15

Asn Val

<210> SEQ ID NO 101
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 101

Lys Leu Asn Asp Leu Cys Phe Ser Asn Val Tyr Ala Asp Ser Phe Val
1               5                   10                  15

Val Lys

<210> SEQ ID NO 102
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 102

Asn Val Tyr Ala Asp Ser Phe Val Val Lys Gly Asp Asp Val Arg Gln
1               5                   10                  15

Ile Ala

<210> SEQ ID NO 103
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 103

Val Lys Gly Asp Asp Val Arg Gln Ile Ala Pro Gly Gln Thr Gly Val
1               5                   10                  15

Ile Ala

<210> SEQ ID NO 104
<211> LENGTH: 16
<212> TYPE: PRT
<213> ORGANISM: Artificial Sequence
<220> FEATURE:
<223> OTHER INFORMATION: Note: Artificial = synthetic construct

<400> SEQUENCE: 104

Ile Ala Pro Gly Gln Thr Gly Val Ile Ala Asp Tyr Asn Tyr Lys Leu
1               5                   10                  15

<210> SEQ ID NO 105
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 105

Gly Val Ile Ala Asp Tyr Asn Tyr Lys Leu Pro Asp Asp Phe Met Gly
1               5                   10                  15
```

Cys Val

<210> SEQ ID NO 106
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 106

Lys Leu Pro Asp Asp Phe Met Gly Cys Val Leu Ala Trp Asn Thr Arg
1               5                   10                  15

Asn Ile

<210> SEQ ID NO 107
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 107

Asn Ile Asp Ala Thr Ser Thr Gly Asn Tyr Asn Tyr Lys Tyr Arg Tyr
1               5                   10                  15

Leu Arg

<210> SEQ ID NO 108
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 108

Asn Tyr Asn Tyr Lys Tyr Arg Tyr Leu Arg His Gly Lys Leu Arg Pro
1               5                   10                  15

Phe

<210> SEQ ID NO 109
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 109

Tyr Leu Arg His Gly Lys Leu Arg Pro Phe Glu Arg Asp Ile Ser Asn
1               5                   10                  15

Val

<210> SEQ ID NO 110
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 110

Arg Pro Phe Glu Arg Asp Ile Ser Asn Val Pro Phe Ser Pro Asp Gly
1               5                   10                  15

Lys

<210> SEQ ID NO 111

```
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 111

Ser Asn Val Pro Phe Ser Pro Asp Gly Lys Pro Cys Thr Pro Pro Ala
1               5                   10                  15
Leu

<210> SEQ ID NO 112
<211> LENGTH: 16
<212> TYPE: PRT
<213> ORGANISM: Artificial Sequence
<220> FEATURE:
<223> OTHER INFORMATION: Note: Artificial = synthetic construct

<400> SEQUENCE: 112

Asp Gly Lys Pro Cys Thr Pro Pro Ala Leu Asn Cys Tyr Trp Pro Leu
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Note: Artificial = synthetic construct

<400> SEQUENCE: 113

Pro Pro Ala Leu Asn Cys Tyr Trp Pro Leu Asn Asp Tyr Gly Phe Tyr
1               5                   10                  15

<210> SEQ ID NO 114
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 114

Gly Phe Tyr Thr Thr Thr Gly Ile Gly Tyr Gln Pro Tyr Arg Val Val
1               5                   10                  15
Val Leu

<210> SEQ ID NO 115
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 115

Val Val Leu Ser Phe Glu Leu Leu Asn Ala Pro Ala Thr Val Cys Gly
1               5                   10                  15
Pro Lys

<210> SEQ ID NO 116
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 116

Asn Ala Pro Ala Thr Val Cys Gly Pro Lys Leu Ser Thr Asp Leu Ile
```

```
                    1               5                  10                  15
Lys

<210> SEQ ID NO 117
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 117

Gly Pro Lys Leu Ser Thr Asp Leu Ile Lys Asn Gln Cys Val Asn Phe
1               5                   10                  15

Asn Phe

<210> SEQ ID NO 118
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 118

Ile Lys Asn Gln Cys Val Asn Phe Asn Phe Asn Gly Leu Thr Gly Thr
1               5                   10                  15

Gly Val

<210> SEQ ID NO 119
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 119

Asn Phe Asn Gly Leu Thr Gly Thr Gly Val Leu Thr Pro Ser Ser Lys
1               5                   10                  15

Arg Phe

<210> SEQ ID NO 120
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 120

Gly Val Leu Thr Pro Ser Ser Lys Arg Phe Gln Pro Phe Gln Gln Phe
1               5                   10                  15

Gly Arg

<210> SEQ ID NO 121
<211> LENGTH: 15
<212> TYPE: PRT
<213> ORGANISM: Artificial Sequence
<220> FEATURE:
<223> OTHER INFORMATION: Note:  Artificial = synthetic construct

<400> SEQUENCE: 121

Arg Phe Gln Pro Phe Gln Gln Phe Gly Arg Asp Val Ser Asp Phe
1               5                   10                  15

<210> SEQ ID NO 122
<211> LENGTH: 18
```

```
<212> TYPE: PRT
<213> ORGANISM: Artificial Sequence
<220> FEATURE:
<223> OTHER INFORMATION: Note:  Artificial = synthetic construct

<400> SEQUENCE: 122

Gln Gln Phe Gly Arg Asp Val Ser Asp Phe Thr Asp Ser Val Arg Asp
1               5                   10                  15

Pro Lys

<210> SEQ ID NO 123
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 123

Asp Phe Thr Asp Ser Val Arg Asp Pro Lys Thr Ser Glu Ile Leu Asp
1               5                   10                  15

Ile

<210> SEQ ID NO 124
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 124

Asp Pro Lys Thr Ser Glu Ile Leu Asp Ile Ser Pro Cys Ser Phe Gly
1               5                   10                  15

Gly Val

<210> SEQ ID NO 125
<211> LENGTH: 19
<212> TYPE: PRT
<213> ORGANISM: Artificial Sequence
<220> FEATURE:
<223> OTHER INFORMATION: Note:  Artificial = synthetic construct

<400> SEQUENCE: 125

Asp Ile Ser Pro Cys Ser Phe Gly Gly Val Ser Val Ile Thr Pro Gly
1               5                   10                  15

Thr Asn Ala

<210> SEQ ID NO 126
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 126

Val Ser Val Ile Thr Pro Gly Thr Asn Ala Ser Ser Glu Val Ala Val
1               5                   10                  15

Leu Tyr

<210> SEQ ID NO 127
<211> LENGTH: 16
<212> TYPE: PRT
<213> ORGANISM: Artificial Sequence
<220> FEATURE:
<223> OTHER INFORMATION: Note:  Artificial = synthetic construct
```

```
-continued
```

```
<400> SEQUENCE: 127

Leu Tyr Gln Asp Val Asn Cys Thr Asp Val Ser Thr Ala Ile His Ala
1               5                   10                  15

<210> SEQ ID NO 128
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 128

Cys Thr Asp Val Ser Thr Ala Ile His Ala Asp Gln Leu Thr Pro Ala
1               5                   10                  15

Trp Arg

<210> SEQ ID NO 129
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 129

His Ala Asp Gln Leu Thr Pro Ala Trp Arg Ile Tyr Ser Thr Gly Asn
1               5                   10                  15

Asn Val

<210> SEQ ID NO 130
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 130

Trp Arg Ile Tyr Ser Thr Gly Asn Asn Val Phe Gln Thr Gln Ala Gly
1               5                   10                  15

Cys Leu

<210> SEQ ID NO 131
<211> LENGTH: 16
<212> TYPE: PRT
<213> ORGANISM: Artificial Sequence
<220> FEATURE:
<223> OTHER INFORMATION: Note:   Artificial = synthetic construct

<400> SEQUENCE: 131

Asn Val Phe Gln Thr Gln Ala Gly Cys Leu Ile Gly Ala Glu His Val
1               5                   10                  15

<210> SEQ ID NO 132
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 132

His Val Asp Thr Ser Tyr Glu Cys Asp Ile Pro Ile Gly Ala Gly Ile
1               5                   10                  15

Cys Ala

<210> SEQ ID NO 133
```

```
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 133

Asp Ile Pro Ile Gly Ala Gly Ile Cys Ala Ser Tyr His Thr Val Ser
 1               5                  10                  15

Leu Leu

<210> SEQ ID NO 134
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 134

Cys Ala Ser Tyr His Thr Val Ser Leu Leu Arg Ser Thr Ser Gln Lys
 1               5                  10                  15

Ser Ile

<210> SEQ ID NO 135
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 135

Leu Leu Arg Ser Thr Ser Gln Lys Ser Ile Val Ala Tyr Thr Met Ser
 1               5                  10                  15

Leu

<210> SEQ ID NO 136
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 136

Lys Ser Ile Val Ala Tyr Thr Met Ser Leu Gly Ala Asp Ser Ser Ile
 1               5                  10                  15

Ala Tyr

<210> SEQ ID NO 137
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 137

Ser Leu Gly Ala Asp Ser Ser Ile Ala Tyr Ser Asn Asn Thr Ile Ala
 1               5                  10                  15

Ile

<210> SEQ ID NO 138
<211> LENGTH: 18
<212> TYPE: PRT
<213> ORGANISM: Artificial Sequence
<220> FEATURE:
<223> OTHER INFORMATION: Note:  Artificial = synthetic construct
```

-continued

<400> SEQUENCE: 138

Ile Ala Tyr Ser Asn Asn Thr Ile Ala Ile Pro Thr Asn Phe Ser Ile
1               5                   10                  15
Ser Ile

<210> SEQ ID NO 139
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 139

Ala Ile Pro Thr Asn Phe Ser Ile Ser Ile Thr Thr Glu Val Met Pro
1               5                   10                  15
Val

<210> SEQ ID NO 140
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 140

Ile Ser Ile Thr Thr Glu Val Met Pro Val Ser Met Ala Lys Thr Ser
1               5                   10                  15
Val

<210> SEQ ID NO 141
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 141

Lys Thr Ser Val Asp Cys Asn Met Tyr Ile Cys Gly Asp Ser Thr Glu
1               5                   10                  15
Cys Ala

<210> SEQ ID NO 142
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 142

Leu Gln Tyr Gly Ser Phe Cys Thr Gln Leu Asn Arg Ala Leu Ser Gly
1               5                   10                  15
Ile Ala

<210> SEQ ID NO 143
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 143

Gln Leu Asn Arg Ala Leu Ser Gly Ile Ala Ala Glu Gln Asp Arg Asn
1               5                   10                  15

Thr Arg

<210> SEQ ID NO 144
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 144

Ile Ala Ala Glu Gln Asp Arg Asn Thr Arg Glu Val Phe Ala Gln Val
1               5                   10                  15

Lys

<210> SEQ ID NO 145
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 145

Asn Thr Arg Glu Val Phe Ala Gln Val Lys Gln Met Tyr Lys Thr Pro
1               5                   10                  15

Thr Leu

<210> SEQ ID NO 146
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 146

Val Lys Gln Met Tyr Lys Thr Pro Thr Leu Lys Tyr Phe Gly Gly Phe
1               5                   10                  15

Asn Phe

<210> SEQ ID NO 147
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 147

Thr Leu Lys Tyr Phe Gly Gly Phe Asn Phe Ser Gln Ile Leu Pro Asp
1               5                   10                  15

Pro Leu

<210> SEQ ID NO 148
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 148

Asn Phe Ser Gln Ile Leu Pro Asp Pro Leu Lys Pro Thr Lys Arg Ser
1               5                   10                  15

Phe Ile

<210> SEQ ID NO 149

```
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 149

Pro Leu Lys Pro Thr Lys Arg Ser Phe Ile Glu Asp Leu Leu Phe Asn
1               5                   10                  15

Lys Val

<210> SEQ ID NO 150
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 150

Phe Ile Glu Asp Leu Leu Phe Asn Lys Val Thr Leu Ala Asp Ala Gly
1               5                   10                  15

Phe Met

<210> SEQ ID NO 151
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 151

Lys Val Thr Leu Ala Asp Ala Gly Phe Met Lys Gln Tyr Gly Glu Cys
1               5                   10                  15

Leu

<210> SEQ ID NO 152
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 152

Gly Phe Met Lys Gln Tyr Gly Glu Cys Leu Gly Asp Ile Asn Ala Arg
1               5                   10                  15

Asp Leu

<210> SEQ ID NO 153
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 153

Cys Leu Gly Asp Ile Asn Ala Arg Asp Leu Ile Cys Ala Gln Lys Phe
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 154
```

Ala Arg Asp Leu Ile Cys Ala Gln Lys Phe Asn Gly Leu Thr Val Leu
1               5                   10                  15

<210> SEQ ID NO 155
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 155

Ala Gln Lys Phe Asn Gly Leu Thr Val Leu Pro Pro Leu Leu Thr Asp
1               5                   10                  15

Asp Met

<210> SEQ ID NO 156
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 156

Val Leu Pro Pro Leu Leu Thr Asp Asp Met Ile Ala Ala Tyr Thr Ala
1               5                   10                  15

Ala Leu

<210> SEQ ID NO 157
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 157

Ala Ala Leu Val Ser Gly Thr Ala Thr Ala Gly Trp Thr Phe Gly Ala
1               5                   10                  15

Gly Ala

<210> SEQ ID NO 158
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 158

Gly Ala Ala Leu Gln Ile Pro Phe Ala Met Gln Met Ala Tyr Arg Phe
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Note:  Artificial = synthetic construct

<400> SEQUENCE: 159

Pro Phe Ala Met Gln Met Ala Tyr Arg Phe Asn Gly Ile Gly Val
1               5                   10                  15

<210> SEQ ID NO 160
<211> LENGTH: 17
<212> TYPE: PRT
<213> ORGANISM: Artificial Sequence

```
<220> FEATURE:
<223> OTHER INFORMATION: Note:  Artificial = synthetic construct

<400> SEQUENCE: 160

Gly Ile Gly Val Thr Gln Asn Val Leu Tyr Glu Asn Gln Lys Gln Ile
1               5                   10                  15

Ala

<210> SEQ ID NO 161
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 161

Val Leu Tyr Glu Asn Gln Lys Gln Ile Ala Asn Gln Phe Asn Lys Ala
1               5                   10                  15

Ile

<210> SEQ ID NO 162
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 162

Lys Ala Ile Ser Gln Ile Gln Glu Ser Leu Thr Thr Thr Ser Thr Ala
1               5                   10                  15

Leu

<210> SEQ ID NO 163
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 163

Thr Ala Leu Gly Lys Leu Gln Asp Val Val Asn Gln Asn Ala Gln Ala
1               5                   10                  15

Leu

<210> SEQ ID NO 164
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 164

Gln Ala Leu Asn Thr Leu Val Lys Gln Leu Ser Ser Asn Phe Gly Ala
1               5                   10                  15

Ile

<210> SEQ ID NO 165
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 165
```

```
Ala Ile Ser Ser Val Leu Asn Asp Ile Leu Ser Arg Leu Asp Lys Val
1               5                   10                  15

Glu Ala

<210> SEQ ID NO 166
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 166

Ile Leu Ser Arg Leu Asp Lys Val Glu Ala Glu Val Gln Ile Asp Arg
1               5                   10                  15

Leu Ile

<210> SEQ ID NO 167
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 167

Ser Leu Gln Thr Tyr Val Thr Gln Gln Leu Ile Arg Ala Ala Glu Ile
1               5                   10                  15

Arg Ala

<210> SEQ ID NO 168
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 168

Gln Leu Ile Arg Ala Ala Glu Ile Arg Ala Ser Ala Asn Leu Ala Ala
1               5                   10                  15

Thr Lys

<210> SEQ ID NO 169
<211> LENGTH: 16
<212> TYPE: PRT
<213> ORGANISM: Artificial Sequence
<220> FEATURE:
<223> OTHER INFORMATION: Note:   Artificial = synthetic construct

<400> SEQUENCE: 169

Arg Ala Ser Ala Asn Leu Ala Ala Thr Lys Met Ser Glu Cys Val Leu
1               5                   10                  15

<210> SEQ ID NO 170
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 170

Ala Ala Thr Lys Met Ser Glu Cys Val Leu Gly Gln Ser Lys Arg Val
1               5                   10                  15

Asp Phe

<210> SEQ ID NO 171
```

```
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 171

Val Leu Gly Gln Ser Lys Arg Val Asp Phe Cys Gly Lys Gly Tyr His
1               5                   10                  15

Leu Met

<210> SEQ ID NO 172
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 172

Asp Phe Cys Gly Lys Gly Tyr His Leu Met Ser Phe Pro Gln Ala Ala
1               5                   10                  15

Pro His

<210> SEQ ID NO 173
<211> LENGTH: 17
<212> TYPE: PRT
<213> ORGANISM: Artificial Sequence
<220> FEATURE:
<223> OTHER INFORMATION: Note:  Artificial = synthetic construct

<400> SEQUENCE: 173

Leu Met Ser Phe Pro Gln Ala Ala Pro His Gly Val Val Phe Leu His
1               5                   10                  15

Val

<210> SEQ ID NO 174
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 174

Ala Pro His Gly Val Val Phe Leu His Val Thr Tyr Val Pro Ser Gln
1               5                   10                  15

Glu Arg

<210> SEQ ID NO 175
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 175

His Val Thr Tyr Val Pro Ser Gln Glu Arg Asn Phe Thr Thr Ala Pro
1               5                   10                  15

Ala Ile

<210> SEQ ID NO 176
<211> LENGTH: 18
<212> TYPE: PRT
<213> ORGANISM: Artificial Sequence
<220> FEATURE:
<223> OTHER INFORMATION: Note:  Artificial = synthetic construct
```

```
<400> SEQUENCE: 176

Glu Arg Asn Phe Thr Thr Ala Pro Ala Ile Cys His Glu Gly Lys Ala
1               5                   10                  15

Tyr Phe

<210> SEQ ID NO 177
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 177

Ala Ile Cys His Glu Gly Lys Ala Tyr Phe Pro Arg Glu Gly Val Phe
1               5                   10                  15

Val Phe

<210> SEQ ID NO 178
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 178

Tyr Phe Pro Arg Glu Gly Val Phe Val Phe Asn Gly Thr Ser Trp Phe
1               5                   10                  15

Ile

<210> SEQ ID NO 179
<211> LENGTH: 16
<212> TYPE: PRT
<213> ORGANISM: Artificial Sequence
<220> FEATURE:
<223> OTHER INFORMATION: Note:   Artificial = synthetic construct

<400> SEQUENCE: 179

Phe Val Phe Asn Gly Thr Ser Trp Phe Ile Thr Gln Arg Asn Phe Phe
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Note:   Artificial = synthetic construct

<400> SEQUENCE: 180

Ser Trp Phe Ile Thr Gln Arg Asn Phe Phe Ser Pro Gln Ile Ile
1               5                   10                  15

<210> SEQ ID NO 181
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 181

Gln Arg Asn Phe Phe Ser Pro Gln Ile Ile Thr Thr Asp Asn Thr Phe
1               5                   10                  15

Val
```

```
<210> SEQ ID NO 182
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 182

Val Ile Gly Ile Ile Asn Asn Thr Val Tyr Asp Pro Leu Gln Pro Glu
1               5                   10                  15

Leu

<210> SEQ ID NO 183
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 183

Thr Val Tyr Asp Pro Leu Gln Pro Glu Leu Asp Ser Phe Lys Glu Glu
1               5                   10                  15

Leu

<210> SEQ ID NO 184
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 184

Pro Glu Leu Asp Ser Phe Lys Glu Glu Leu Asp Lys Tyr Phe Lys Asn
1               5                   10                  15

His

<210> SEQ ID NO 185
<211> LENGTH: 17
<212> TYPE: PRT
<213> ORGANISM: Artificial Sequence
<220> FEATURE:
<223> OTHER INFORMATION: Note:   Artificial = synthetic construct

<400> SEQUENCE: 185

Glu Glu Leu Asp Lys Tyr Phe Lys Asn His Thr Ser Pro Asp Val Asp
1               5                   10                  15

Leu

<210> SEQ ID NO 186
<211> LENGTH: 18
<212> TYPE: PRT
<213> ORGANISM: Artificial Sequence
<220> FEATURE:
<223> OTHER INFORMATION: Note:   Artificial = synthetic construct

<400> SEQUENCE: 186

Lys Asn His Thr Ser Pro Asp Val Asp Leu Gly Asp Ile Ser Gly Ile
1               5                   10                  15

Asn Ala

<210> SEQ ID NO 187
<211> LENGTH: 17
<212> TYPE: PRT
<213> ORGANISM: Artificial Sequence
<220> FEATURE:
```

-continued

<223> OTHER INFORMATION: Note: Artificial = synthetic construct

<400> SEQUENCE: 187

Asp Leu Gly Asp Ile Ser Gly Ile Asn Ala Ser Val Val Asn Ile Gln
1               5                   10                  15

Lys

<210> SEQ ID NO 188
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 188

Ile Asn Ala Ser Val Val Asn Ile Gln Lys Glu Ile Asp Arg Leu Asn
1               5                   10                  15

Glu Val

<210> SEQ ID NO 189
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 189

Gln Lys Glu Ile Asp Arg Leu Asn Glu Val Ala Lys Asn Leu Asn Glu
1               5                   10                  15

Ser Leu

<210> SEQ ID NO 190
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 190

Glu Val Ala Lys Asn Leu Asn Glu Ser Leu Ile Asp Leu Gln Glu Leu
1               5                   10                  15

Gly Lys

<210> SEQ ID NO 191
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 191

Ser Leu Ile Asp Leu Gln Glu Leu Gly Lys Tyr Glu Gln Tyr Ile Lys
1               5                   10                  15

Trp

<210> SEQ ID NO 192
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 192

Leu Gly Lys Tyr Glu Gln Tyr Ile Lys Trp Pro Trp Tyr Val Trp Leu

```
1               5                   10                  15
Gly Phe

<210> SEQ ID NO 193
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 193

Lys Trp Pro Trp Tyr Val Trp Leu Gly Phe Ile Ala Gly Leu Ile Ala
1               5                   10                  15

Ile Val

<210> SEQ ID NO 194
<211> LENGTH: 16
<212> TYPE: PRT
<213> ORGANISM: Artificial Sequence
<220> FEATURE:
<223> OTHER INFORMATION: Note:  Artificial = synthetic construct

<400> SEQUENCE: 194

Gly Phe Ile Ala Gly Leu Ile Ala Ile Val Met Val Thr Ile Leu Leu
1               5                   10                  15

<210> SEQ ID NO 195
<211> LENGTH: 20
<212> TYPE: PRT
<213> ORGANISM: Artificial Sequence
<220> FEATURE:
<223> OTHER INFORMATION: Note:  Artificial = synthetic construct

<400> SEQUENCE: 195

Ile Ala Ile Val Met Val Thr Ile Leu Leu Cys Cys Met Thr Ser Cys
1               5                   10                  15

Cys Ser Cys Leu
            20

<210> SEQ ID NO 196
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 196

Cys Cys Met Thr Ser Cys Cys Ser Cys Leu Lys Gly Ala Cys Ser Cys
1               5                   10                  15

Gly Ser

<210> SEQ ID NO 197
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 197

Cys Leu Lys Gly Ala Cys Ser Cys Gly Ser Cys Cys Lys Phe Asp Glu
1               5                   10                  15

Asp Asp

<210> SEQ ID NO 198
```

```
<211> LENGTH: 18
<212> TYPE: PRT
<213> ORGANISM: Artificial Sequence
<220> FEATURE:
<223> OTHER INFORMATION: Note:  Artificial = synthetic construct

<400> SEQUENCE: 198

Gly Ser Cys Cys Lys Phe Asp Glu Asp Asp Ser Glu Pro Val Leu Lys
1               5                   10                  15

Gly Val

<210> SEQ ID NO 199
<211> LENGTH: 15
<212> TYPE: PRT
<213> ORGANISM: Artificial Sequence
<220> FEATURE:
<223> OTHER INFORMATION: Note:  Artificial = synthetic construct

<400> SEQUENCE: 199

Asp Asp Ser Glu Pro Val Leu Lys Gly Val Lys Leu His Tyr Thr
1               5                   10                  15
```

SARS VACCINE COMPOSITIONS AND METHODS OF MAKING AND USING THEM

RELATED APPLICATIONS

The present application is a continuation of U.S. patent application Ser. No. 12/106,021, filed Apr. 18, 2008, now abandoned which is a continuation-in-part of U.S. non-provisional patent application Ser. No. 11/401,434, filed Apr. 10, 2006, which issued Oct. 21, 2008, as U.S. Pat. No. 7,439,052, and which claims the benefit of U.S. provisional patent application Ser. No. 60/670,574, filed Apr. 11, 2005, U.S. provisional patent application Ser. No. 60/669,738, filed Apr. 8, 2005, and is a continuation-in-part of U.S. non-provisional patent application Ser. No. 10/873,015, filed Jun. 21, 2004, which issued Aug. 5, 2008, as U.S. Pat. No. 7,407,662, and which is a continuation in part of U.S. non-provisional patent application Ser. No. 10/601,656, filed Jun. 20, 2003, which issued Aug. 5, 2008, as U.S. Pat. No. 7,407,663, and which is a continuation-in-part of U.S. non-provisional patent application Ser. No. 10/311,679 filed Dec. 18, 2002, abandoned, which is a U.S. national phase from PCT patent application number PCT/IB01/01099, filed Jun. 21, 2001, which claims the benefit of Australian patent application PQ8469, filed Jun. 29, 2000, and PCT patent application number PCT/AU00/01603, filed Dec. 28, 2000. U.S. patent application Ser. No. 12/106,021 also claims the benefit of U.S. provisional patent application Ser. No. 60/925,628, filed Apr. 20, 2007. U.S. non-provisional patent application Ser. No. 10/651,066 claims the benefit of U.S. provisional patent application Ser. No. 60/390,066 filed Jun. 20, 2002. U.S. non-provisional patent application Ser. No. 10/873,015, filed Jun. 21, 2004, also claims the benefit of U.S. provisional patent application Ser. No. 60/491,928 filed Aug. 1, 2003, 60/533,542 filed Dec. 31, 2003, and 60/542,947 filed Feb. 9, 2004. All of these applications are herein incorporated by reference in their entirety.

GOVERNMENT LICENSE RIGHTS

The U.S. Government has a paid-up license in this invention and the right in limited circumstances to require the patent owner to license others on reasonable terms as provided for by the terms of STIR Grant #1 41 AI060267-01 awarded by NIAID.

FIELD OF THE INVENTION

The present invention relates to a delipidation method employing a solvent system useful for extracting lipids from a virus, thereby creating a modified viral particle. In a preferred embodiment, the virus is severe acute respiratory syndrome (SARS) caused by Coronaviruses. The solvent system of the present invention is optimally designed such that upon delipidation of the virus, the viral particle remains substantially intact. By dissolving the lipid envelope surrounding the viral particle using the method of the present invention, the resultant modified viral particle has exposed antigens (or epitopes), which foster and promote cellular responses and antibody production when introduced into a human or an animal. The resulting modified viral particle of the present invention initiates a positive immunogenic response in the species into which it is re-introduced. The present invention can be applied to delipidating viruses from a specific patient for future reintroduction into the patient, to delipidating stock viruses, or non-patient specific viruses, for use as a vaccine, or to delipidating and combining both non-patient specific viruses and patient specific viruses to create a therapeutic cocktail.

BACKGROUND OF THE INVENTION

Introduction

Viruses, of varied etiology, affect billions of animals and humans each year and inflict an enormous economic burden on society. Many viruses contain lipid as a major component of the membrane that surrounds them. Viruses affect animals and humans causing extreme suffering, morbidity, and mortality. These viruses travel throughout the body in biological fluids such as blood, peritoneal fluid, lymphatic fluid, pleural fluid, pericardial fluid, cerebrospinal fluid, and in various fluids of the reproductive system. Fluid contact at any site promotes transmission of disease. Other viruses reside primarily in different organ systems and in specific tissues, proliferate and then enter the circulatory system to gain access to other tissues and organs at remote sites. If the body does not exhibit a positive immune response against these pathogens, they infect many cell types within the body, inhibiting these cells from performing their normal functions.

The human immune system is composed of various cell types that collectively protect the body from different viruses. The immune system provides multiple means for targeting and eliminating foreign elements, including humoral and cellular immune responses, participating primarily in antigen recognition and elimination. An immune response to foreign elements requires the presence of B-lymphocytes (B cells) or T-lymphocytes (T cells) in combination with antigen-presenting cells (APC), which are usually macrophage or dendrite cells. The APCs are specialized immune cells that capture antigens. Once inside an APC, antigens are broken down into smaller fragments called epitopes—the unique markers carried by the antigen surface. These epitopes are subsequently displayed on the surface of the APCs and are responsible for triggering an antibody response in defense of the infection.

In a humoral immune response, when an APC displaying antigens (in the form of unique epitope markers) foreign to the body are recognized, B cells are activated, proliferating and producing antibodies. These antibodies specifically bind to the antigens present on the virus. After the antibody attaches, the APC engulfs the entire antigen and kills it. This type of antibody immune response is primarily involved in the prevention of viral infection.

In a cellular immune response, T cells are activated on recognizing the antigen displayed on the APC. There are two steps in the cellular immune response. The first step involves activation of cytotoxic T cells (CTL) or $CD8^+$ T killer cells that proliferate and kill target cells that specifically present antigens. The second involves helper T cells (HTL) or $CD4^+$ T cells that regulate the production of antibodies and the activity of $CD8^+$ cells. The $CD4^+$ T cells provide growth factors to $CD8^+$ T cells that allow them to proliferate and function efficiently.

Certain infective pathogens are deemed "chronic" due to their structure. For example, some viruses are able to evade an immune response because of their ability to hide some of their antigens from the immune system. Viruses contain an outer envelope made up of lipids and fats derived from the host cell membrane during the budding process. Viruses are comprised of virions, non-cellular infectious agents consisting of a single type of nucleic acid (either RNA or DNA), surrounded by a protein coat. The outer protein covering of viruses is called a capsid, made up of repeating subunits called capsomeres.

Since viruses are non-metabolic, they only reproduce within living host cells. The virus codes the proteins of the viral envelope while the host cell codes the lipids and carbohydrates. Therefore, the lipid and carbohydrate content within a given viral envelope is dependent on the particular host. The enveloped viral particles therefore partially adopt the identity of the host cell, via lipid and carbohydrate content, and are able to conceal antigens associated with them, which would normally have initiated an immune response. Instead, the viral particle confuses the host immune system by presenting it with an antigenic complex that contains components of host tissues, and is perceived by the host immune system as partly "self" and partly "foreign". The immune system is forced to produce the "compromise", ineffective antibodies which do not destroy the viral particles, allowing them to proliferate and slowly cause severe damage to the body, while destroying host cells.

Recent epidemics affecting the immune system include acquired immune deficiency syndrome (AIDS), believed to be caused by the human immunodeficiency virus (HIV). Related viruses affect animal species, for example, simians and felines (SIV and FIV, respectively). Other major viral infections include, but are not limited to, severe acute respiratory syndrome (SARS) caused by Coronaviruses, meningitis, cytomegalovirus, and hepatitis in its various forms.

Current Methods of Treatment

One prior art method of treating viruses of varied etiology is via drug therapy. Most anti-viral drug therapies are directed toward preventing or inhibiting viral replication and appear to focus on the initial attachment of the virus to the T4 lymphocyte or macrophage, the transcription of viral RNA to viral DNA and the assembly of new virus during replication. The high mutation rate of the virus, especially in the case of HIV, is a major difficulty with existing treatments because the various strains become resistant to anti-viral drug therapy. Furthermore, anti-viral drug therapy treatment may cause the evolution of resistant strains of the virus. Other drawbacks to drug therapies are the undesirable side effects and patient compliance requirements. In addition, many individuals are afflicted with multiple viral infections such as a combination of HIV and hepatitis. Such individuals require even more aggressive and expensive drug regimens to counteract disease progression, which in turn cause greater side effects and a greater likelihood of multiple drug resistance.

Also known in the prior art is prevention of disease via the use of vaccinations. Vaccines have been singularly responsible for conferring immune response against several human pathogens. They are designed to stimulate the immune system to protect against various viral infections. In general, a vaccine is produced from an antigen, isolated or produced from the disease-causing microorganism, which can elicit an immune response. When a vaccine is injected into the blood stream as a preventive measure to create an effective immune response, the B cells in the blood stream perceive the antigens contained by the vaccine as foreign or 'non-self' and respond by producing antibodies, which bind to the antigens and inactivate them. Memory cells are thereby produced and remain ready to mount a quick protective immune response against subsequent infection with the same disease-causing agent. Thus when an infective pathogen containing similar antigens as the vaccine enters the body, the immune system will recognize the protein and instigate an effective defense against infection.

The current methods of vaccination do have drawbacks, making them less than optimally desirable for immunizing individuals against particular pathogens, such as coronavirus and HIV. The existing vaccine strategies aim to expose the body to the antigens associated with infective pathogens so that the body builds an immune response against these pathogens. For example, coronavirus, hepatitis B and HIV pathogens are able to survive and proliferate in the human body despite the immune response. One explanation offered in the prior art is that the antigens of these microorganisms change constantly so the antibodies produced in response to a particular antigen are no longer effective when the antigen mutates. Although antigenic variation has been addressed via the attempted use of combination drugs or antigens, no prior art vaccine has succeeded adequately in addressing infections such as SARS.

Another approach to treating viruses of varied etiology is to inactivate the virus. Prior art methods of inactivating viruses using chemical agents have relied on organic solvents such as chloroform or glutaraldehyde. Viral inactivation does present problems since inactivation of a virus does not provide a protective immune response against viral infection. In addition, it is largely geared towards denaturing viral proteins, thereby destroying the structure of the viral particle. In sum, prior art methods have largely focused on destroying, yet not suitably modifying, viral particles to produce an immune response.

Current Methods of Manufacture of Viral Treatments and Medicaments

Viral Inactivation (or Chemical Kill)

Described in the prior art are methods of treating viral particles with organic solvents and high temperatures thus dissolving the lipid envelopes and subsequently inactivating the virus. In those methods, blood is withdrawn from the patient and separated into two phases—the first phase including red cells and platelets and the second phase containing plasma, white cells, and cell-free virus (virion). The second phase is treated with an organic solvent, thereby killing the infected cells and virions, and subsequently reintroduced into the patient. In addition to dissolving the lipid envelope of the virus, the high organic solvent concentrations cause cell death and damage to the antigens. Essentially, this method results in a "chemical kill" of the cell.

Glutaraldehyde is one such solvent whereby cell inactivation is achieved as known by those of ordinary skill in the art by fixation with a dilute solution of glutaraldehyde at about 1:250. Although treating the virus with glutaraldehyde effectively delipidates the virus, it also destroys the core. Destruction of the core is not desirable for producing a modified viral particle useful for inducing an immune response in a recipient.

Chloroform is another such solvent. Chloroform, however, denatures many plasma proteins and is not suitable for use with biological fluids, which will be reintroduced into the animal or human. These plasma proteins deleteriously affected by chloroform serve important biological functions including coagulation, hormonal response, and immune response. These functions are essential to life and thus damage to these proteins may have an adverse effect on a patient's health, possibly leading to death.

Further, many of the methods described in the prior art involve extensive exposure to elevated temperature in order to kill free virus and infected cells. Elevated temperatures have deleterious effects on the proteins contained in biological fluids, such as plasma.

Current Methods of Manufacturing Vaccines

To date, several manufacturing methods have been employed in search of safe and effective vaccines for immunizing individuals against infective pathogenic agents. To protect an individual from a specific pathogenic infection, a target protein or antigen associated with the infective pathogen is administered to the individual. This includes presenting the protein as part of a non-infective (inactivated) or less infective (attenuated) agent or as a discrete protein composition. Known to one of ordinary skill in the art are the following different types of vaccines: live attenuated vaccines, whole inactivated vaccines, DNA vaccines, combination vaccines, recombinant vaccines, live recombinant vector vaccines, virus like particles and synthetic peptide vaccines.

In live attenuated vaccines, the viruses are rendered less pathogenic to the host, either by specific genetic manipulation of the virus genome or by passage in some type of tissue culture system. In order to achieve genetic manipulation, an inessential gene is deleted or one or more essential genes in the virus are partially damaged. Upon genetic manipulation, the viral particles become less virulent yet retain antigenic features. Live attenuated vaccines can also be used as "vaccine vectors" for other genes, wherein they act as carriers of genes from a second virus (or other pathogen) against which protection is required. Attenuated vaccines (less infective and not inactivated), however, pose several problems. First, it is difficult to ascertain when the attenuated vaccine is no longer pathogenic. The risk of viral infection from the vaccine is too great to properly test for effective attenuation. In addition, attenuated vaccines carry the risk of reverting into a virulent form of the pathogen.

Whole inactivated vaccines are known in the art for immunizing against infection by introducing killed or inactivated viruses to introduce pathogen proteins to an individual's immune system. The administration of killed or inactivated pathogens, via heat or chemical means, into an individual introduces the pathogens to the individual's immune system in a non-infective form thereby initiating an immune response defense. Wholly inactivated vaccines provide protection by directly generating cellular and humoral immune responses against the pathogenic immunogens. There is little threat of infection, because the viral pathogen is killed or otherwise inactivated.

Subunit vaccines are yet another form of vaccination well known to one of ordinary skill in the art. These consist of one or more isolated proteins derived from the pathogen. These proteins act as target antigens against which an immune response is exhibited. The proteins selected for the subunit vaccine are displayed by the pathogen so that upon infection of an individual by the pathogen, the individual's immune system recognizes the pathogen and instigates an immune response. Subunit vaccines are not whole infective agents and are therefore incapable of becoming infective.

DNA vaccine is another type known in the art and uses actual genetic material of pathogens. In addition, synthetic peptide vaccines are made up of parts of synthetic peptides. These synthetic peptides comprise portions of viral proteins chosen specifically to achieve an anti-viral immune response. Also mentioned in the prior art are combination vaccines that, when used in conjunction with one another, generate a broad spectrum of immune responses.

What is needed is a therapeutic method and system for providing patients with patient-specific viral antigens capable of initiating a protective immune response. Accordingly, what is needed is a simple, effective method that does not appreciably denature or extract proteins from the biological sample being treated. What is also needed is an effective delipidation process via which a viral particle is modified, rather than destroyed, thereby both reducing and/or eliminating infectivity of the viral particle and invoking a patient specific, autologous immune response to further reduce viral infection and prevent further infection.

What is also needed is an effective means to immunize individuals against viral pathogen infection that is unique to the individual due to viral mutations. Preferably the means would elicit a broad protective immune response with minimized risk of infecting the individual.

SUMMARY OF THE INVENTION

The present invention solves the problems described above by providing a simple, effective and efficient method for treating and preventing viral infection. In a preferred embodiment, the present invention provides a simple, effective and efficient method for treating and preventing SARS viral infection. The method of the present invention affects the lipid envelope of a virus by utilizing an efficient solvent system, which does not denature or destroy the virus. The present invention employs an optimal solvent and energy system to create, via delipidation, a non-synthetic, host-derived or non host-derived modified viral particle that has its lipid envelope at least partially removed, generating a positive immunologic response when administered to a patient, thereby providing that patient with some degree of protection against the virus. It is believed that these modified viral particles have at least one antigen exposed that was not exposed prior to the delipidation process.

The present invention is also effective in producing an autologous, patient-specific therapeutic vaccine against the virus, by treating a biological fluid containing the virus such that the virus is present in a modified form, with reduced infectivity, and such that an immune response is initiated upon reintroduction of the fluid with reduced lipid content into the patient. This autologous method ensures that patient specific antigens, for example patient specific viral antigens, are introduced into the same patient from which they were obtained to induce an immune response. This is an important feature since a patient's physiology may modify the antigens present in an infectious organism such as a virus. To create the vaccine, a biological fluid (for example, blood) is removed from the patient, the plasma is separated from the blood and treated to reduce the lipid content of the virus in the plasma using an optimal solvent system. A lipid-containing virus, treated in this manner in order to reduce its infectivity and create a modified viral particle with reduced lipid content is administered to a patient, such as an animal or a human, optionally together with a pharmaceutically acceptable carrier, in order to initiate an immune response in the animal or human and create antibodies that bind the exposed epitopes of the modified viral particle. Adjuvants may also be administered with the modified viral particle in the pharmaceutically acceptable carrier or separately.

The present method is also employed to produce non-autologous vaccines, wherein biological fluids with lipid containing viruses from at least one animal or human are treated to produce a modified viral particle for administration into a different (non-autologous) animal or human. The present invention is also effective in producing an non-autologous, vaccine against the virus, by treating a biological fluid such as plasma obtained from an animal or a human with the present method to reduce lipid levels in the fluid and in the virus within the fluid. Such treated fluid with reduced lipid levels and containing modified virus with reduced lipid levels may be introduced into another animal or human which was not the source of the treated biological fluid. This non-autologous method is employed to vaccinate a recipient animal or human against one or more infectious organisms such as viruses. Biological fluids may be used from animals or humans infected with one or more infectious organisms such as viruses, and treated with the present methods to produce a vaccine for administration to a recipient animal or human. Alternatively, or in addition, various stock supplies of virus may be added to a biological fluid before treating the fluid with the method of the present invention to create a vaccine.

The present invention encompasses vaccines made with the delipidation method of the present invention that include more than one strain of the same infectious organism, for example more than one clade of the coronavirus that causes SARS. Such vaccines provide an immune response to more than one strain of the same infectious organism. Any number of different infectious strains or clades of the same virus may be chosen and treated with the delipidation method of the present invention to form numerous vaccines. Alternatively, or in addition, various stock supplies of different strains or clades of virus may be added to a biological fluid before treating the fluid with the method of the present invention to create a vaccine capable of generating an immune response. Stocks of one or more viral preparation may be employed to make a non-autologous vaccine directed to one or more viruses. In this manner combination vaccines are produced which provide protection against multiple strains or clades of a virus or against multiple viruses.

The present invention encompasses vaccines made with the delipidation method of the present invention that include more than one infectious organism, such as more than one virus. Such combination vaccines provide an immune response to more than one infectious organism, for example, SARS, HIV and hepatitis. Any number of different infectious organisms may be chosen and treated with the delipidation method of the present invention to form numerous combination vaccines.

Thus an effective method is presented, by which new vaccines can be developed from lipid containing viruses by removing lipid from the lipid envelope and exposing antigens hidden within the lipid envelope or beneath the surface of the lipid envelope, in turn generating an immune response when re-introduced into the patient.

The present invention provides a modified viral particle comprising at least a partially delipidated viral particle, wherein the partially delipidated viral particle initiates an immune response in a patient and incites protection against an infectious organism in the patient.

The present invention provides a method for creating a modified viral particle comprising the steps of: receiving a plurality of viral particles, each having a viral envelope, in a fluid; exposing the viral particles to a delipidation process; and, partially delipidating the viral particles wherein the delipidation process at least partially removes the viral envelopes to create the modified viral particle and wherein the modified viral particle is capable of provoking a positive immune response in a patient.

The present invention also provides an antigen delivery vehicle and a method for creating an antigen delivery vehicle comprising the steps of: receiving a plurality of viral particles, each having a viral envelope, in a fluid; exposing the viral particles to a delipidation process; and, partially delipidating the viral particles to create modified viral particles that act as antigen delivery vehicles, wherein the delipidation process at least partially removes the viral envelopes to expose at least one antigen and wherein the at least one antigen is capable of provoking a positive immune response in a patient.

The modified viral particles of the present invention comprise at least a partially delipidated viral particle, wherein the partially delipidated viral particle is produced by exposing a non-delipidated viral particle to a delipidation process and wherein the partially delipidated viral particle comprises at least one exposed patient specific antigen that was not exposed in the non-delipidated viral particle.

The present invention also provides a vaccine composition, comprising at least a partially delipidated viral particle having patient-specific viral antigens and optionally a pharmaceutically acceptable carrier, wherein the partially delipidated viral particle is capable of provoking a positive immune response when the composition is administered to a patient.

The present invention also provides a method for making a vaccine comprising: contacting a lipid-containing viral particle in a fluid with a first organic solvent capable of extracting lipid from the lipid-containing viral particle; mixing the fluid and the first organic solvent for a time sufficient to extract lipid from the lipid-containing viral particle; permitting organic and aqueous phases to separate; and collecting the aqueous phase containing a modified viral particle with reduced lipid content wherein the modified viral particle is capable of provoking a positive immune response when administered to a patient. In one embodiment the vaccine protects against SARS caused by coronavirus.

The present invention also provides a method to protect a patient against an infectious viral particle comprising administering to the patient an effective amount of a composition comprising a modified viral particle, wherein the modification comprises at least partial removal of a lipid envelope of the infectious viral particle, and optionally a pharmaceutically acceptable carrier, wherein the amount is effective to provide a protective effect against infection by the infectious viral particle in the animal or the human. In one embodiment, the infectious viral particle is coronavirus.

The present invention also provides a method for provoking a positive immune response in a patient having a plurality of lipid-containing viral particles, comprising the steps of: obtaining a fluid containing the lipid-containing viral particles from the patient; contacting the fluid containing the lipid-containing viral particles with a first organic solvent capable of extracting lipid from the lipid-containing viral particles; mixing the fluid and the first organic solvent: permitting organic and aqueous phases to separate; collecting the aqueous phase containing modified viral particles with reduced lipid content; and introducing the aqueous phase containing the modified viral particles with reduced lipid content into the animal or the human wherein the modified viral particles with reduced lipid content provoke a positive immune response in the animal or the human. In one embodiment, the positive immune response is to the coronavirus which causes SARS.

The present invention also provides a method for treating a viral infection in a patient comprising: removing blood containing a plurality of lipid-containing infectious viral particles from the patient; obtaining plasma from the blood, the plasma containing the lipid-containing infectious viral particles; contacting the plasma containing the lipid-containing infectious viral particles with a first organic solvent capable of extracting lipid from the lipid-containing infectious viral particles to produce modified viral particles having reduced lipid content; mixing the plasma and the first organic solvent; permitting organic and aqueous phases to separate; collecting the aqueous phase containing the modified viral particles;

removing residual solvent from the aqueous phase; and, introducing the aqueous phase containing the modified viral particles into the patient wherein the modified viral particles have at least one exposed patient-specific antigen that was not exposed in the plurality of lipid-containing infectious viral particles. Introduction of these modified viral particles into the patient produces an immune response to treat or lessen the severity of the viral infection. In one embodiment the viral infection that is treated is SARS caused by coronavirus.

The present invention also provides a method for treating a viral infection in a patient comprising: obtaining a fluid comprising plurality of lipid-containing infectious viral particles from a plurality of patients; optionally combining the lipid-containing infectious viral particles with a suitable biologically acceptable carrier; contacting the fluid containing lipid-containing infectious viral particles with a first organic solvent capable of extracting lipid from the lipid-containing infectious viral particles to produce modified viral particles having reduced lipid content; mixing the carrier and the first organic solvent; permitting organic and aqueous phases to separate; collecting the aqueous phase containing the modified viral particles; and introducing the aqueous phase containing the modified viral particles into a different patient wherein the modified viral particles have at least one exposed antigen that was not exposed in the plurality of lipid-containing infectious viral particles. In this embodiment, the lipid-containing infectious viral particles represent one or more viral strains or one or more types of virus and are not patient specific. Introduction of these modified viral particles into the patient produces an immune response to treat or lessen the severity of the viral infection. In one embodiment the viral infection that is treated is SARS caused by coronavirus.

As shown below, the characteristics of the modified viral particle are exhibited in experimental data, showing mice having a positive immunogenic response when vaccinated as compared with a wholly inactivated vaccine. In addition, data exhibiting protein recovery indicate retention of the structural integrity of the viral particle, removing only its lipid-containing envelope.

Fluids which may be treated with the method of the present invention include but are not limited to the following: plasma; serum; lymphatic fluid; cerebrospinal fluid; peritoneal fluid; pleural fluid; pericardial fluid; various fluids of the reproductive system including but not limited to semen, ejaculatory fluids, follicular fluid and amniotic fluid; cell culture reagents such as normal sera, fetal calf serum or serum derived from any other animal or human; and immunological reagents such as various preparations of antibodies and cytokines.

The method of the present invention may be used to treat viruses containing lipid in the viral envelope. A preferred virus treated with the method of the present invention is the coronavirus that causes SARS, and subtypes and clades thereof. Other viruses that can be treated with the method of the present invention include the various immunodeficiency viruses including but not limited to human (HIV) and subtypes and clades such as HIV-1 and HIV-2, simian (SIV), feline (FIV), as well as any other form of immunodeficiency virus. Other preferred viruses to be treated with the method of the present invention include but are not limited to hepatitis in its various forms. Another preferred virus treated with the method of the present invention is the bovine pestivirus. It is to be understood that the present invention is not limited to the viruses provided in the list above. Additional specific viruses are described in the detailed description of this application. All viruses containing lipid, especially in their viral envelope, are included within the scope of the present invention.

Accordingly, it is an object of the present invention to provide a method for treating lipid containing virus in order to create modified viral particles.

It is an object of the present invention to provide a method for treating lipid containing virus in order to create modified viral particles with reduced lipid content while substantially unaffecting protein levels when compared to unmodified viral particles.

Yet another object of the present invention is to provide a method for treating lipid containing virus in order to create modified viral particles with reduced lipid content, with substantially unaffected protein levels when compared to unmodified viral particles, and with at least one exposed antigen associated with the viral particles that was substantially unexposed in unmodified viral particles.

It is another object of the present invention to provide a method for treating or preventing viral disease by administering to a patient modified viral particles with reduced lipid content and at least one exposed antigen associated with the viral particles that was substantially unexposed in unmodified viral particles.

Another object of the present invention is to provide a method for treating a biological fluid in order to reduce or eliminate the infectivity of infectious viral organisms contained therein.

Yet another object of the present invention is to provide a method for creating, in a biological fluid, a plurality of modified lipid containing viral particles having a distribution of reduced lipid content, with a substantial percentage of viral particles having substantially unaffected protein levels when compared to unmodified viral particles.

It is further an object of the present invention to provide a method for treatment of lipid-containing viruses within a fluid, which minimizes deleterious effects on proteins contained within the fluid, thereby creating a modified viral particle with properties that are capable of initiating a positive immune response in a patient.

It is a further object of the present invention to provide a method for treatment of lipid-containing viruses within a fluid, which minimizes deleterious effects on proteins contained within the fluid, thereby creating a modified viral particle with patient-specific viral antigens.

It is another object of the present invention to provide a method for reducing the infectivity of viruses, wherein the method exposes antigenic determinants on the modified viral particle.

Another object of the present invention is to completely or partially delipidate viral particles, wherein the viral particles comprise coronavirus, immunodeficiency virus, hepatitis in its various forms, or any other lipid-containing virus, thereby creating a modified viral particle.

It is a further object of the present invention to completely or partially delipidate viral particles, wherein the viral particles comprise coronavirus, immunodeficiency virus, hepatitis in its various forms, or any other lipid-containing virus, while retaining the structural protein core of the virus.

It is another object of the present invention to provide a method for reducing the infectivity of viruses, wherein the newly formed viral particle can be used as an antigen delivery vehicle.

Yet another object of the present invention is to treat infectious organisms with the method of the present invention in order to reduce their infectivity and provide a vaccine comprising a modified viral particle with reduced lipid content which may be administered to an animal or a human, optionally with a pharmaceutically acceptable carrier and optionally an immunostimulant compound, to prevent or minimize clinical manifestation of disease in a patient following exposure to the virus.

Still another object of the present invention is to treat infectious organisms with the method of the present invention in order to reduce their infectivity and provide a vaccine comprising a modified viral particle with reduced lipid content which may be administered to an animal or a human optionally with a pharmaceutically acceptable carrier and optionally an immunostimulant compound, to initiate a positive immunogenic response in the animal or human.

It is another object of the present invention to provide a SARS anti-viral vaccine.

Another object is to provide a method of modifying viral particles to prepare a preventative vaccine for SARS.

Another object of the present invention is to provide an anti-viral vaccine that induces cellular responses in cells of the immune system, wherein the cellular responses include but are not limited to proliferation of cells and production of immune system molecules such as interferon gamma.

It is a further object of the present invention to lessen the severity of a disease, particularly SARS, caused by a lipid-containing virus in an animal or human receiving a vaccine comprising a composition comprising a virus treated with the method of the present invention, optionally combined with a pharmaceutically acceptable carrier.

It is another object of the present invention to combine viral particles with reduced lipid content having patient specific antigens with delipidated stock viral particles with reduced lipid content to create a therapeutic combination vaccine for the treatment or prevention of more than one viral disease.

These and other features and advantages of the present invention will become apparent after review of the following drawings and detailed description of the disclosed embodiments. Various modifications to the stated embodiments will be readily apparent to those of ordinary skill in the art, and the disclosure set forth herein may be applicable to other embodiments and applications without departing from the spirit and scope of the present invention.

BRIEF DESCRIPTION OF THE DRAWINGS

The accompanying drawings, which are incorporated in and form a part of the specification, illustrate preferred embodiments of the present invention.

FIG. 6 illustrates the Spike Ab titers, comparing the titers in mice vaccinated with delipidated SARS to those in mice vaccinated with inactivated SARS.

FIG. 7 illustrates the NC Ab titers comparing the titers in mice vaccinated with delipidated SARS to those in mice vaccinated with inactivated SARS.

FIG. 9 shows the SARS peptide pools generated and used for the ELISPOT assay FIG. 10 demonstrates IFN-γ ELISPOT responses to SARS CoV NC and Spike peptide pools (Responses from a representative mouse/group).

DETAILED DESCRIPTION OF THE INVENTION

Definitions

Figure 1:
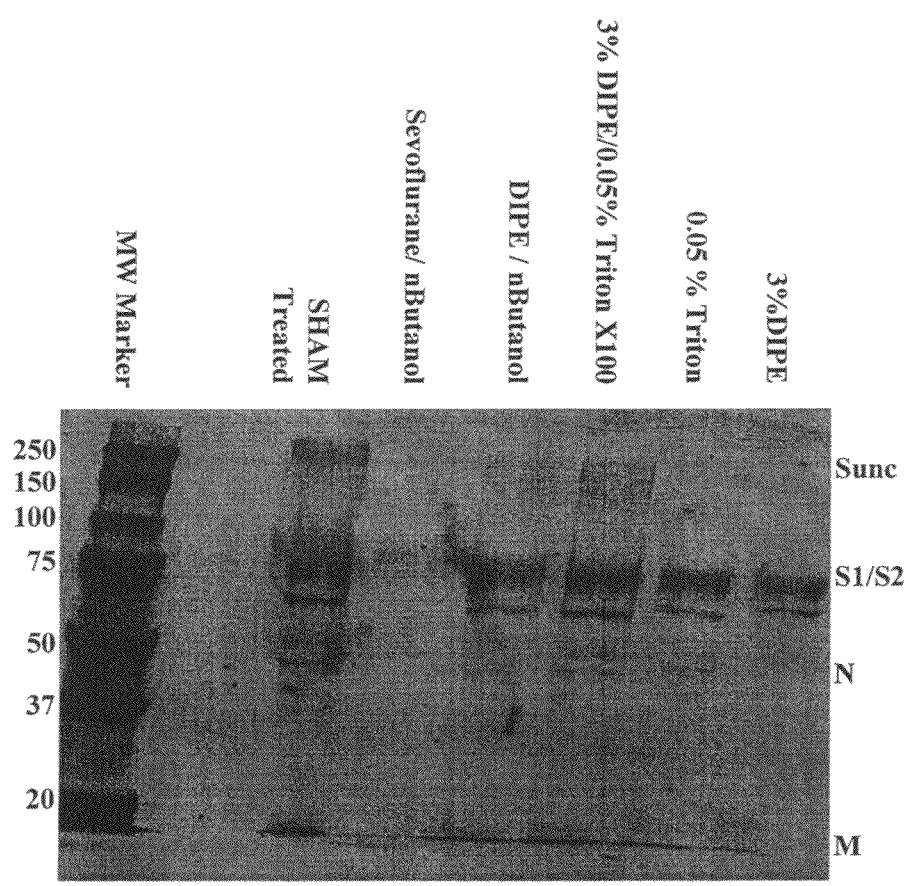
FIG. 1 is a Western blot showing MHV antigenicity following the delipidation procedure with various solvent conditions, as indicated.

By the term "fluid" is meant any fluid containing an infectious organism, including but not limited to, a biological fluid obtained from an organism such as an animal or human. Preferred infectious organisms treated with the method of the present invention are viruses, particularly coronavirus. Such biological fluids obtained from an organism include but are not limited to blood, plasma, serum, cerebrospinal fluid, lymphatic fluid, peritoneal fluid, follicular fluid, amniotic fluid, pleural fluid, pericardial fluid, reproductive fluids and any other fluid contained within the organism. Other fluids may include laboratory samples containing infectious organisms suspended in any chosen fluid. Other fluids include cell culture reagents, many of which include biological compounds such as fluids obtained from living organisms, including but not limited to "normal serum" obtained from various animals and used as growth medium in cell and tissue culture applications.

By the terms "first solvent" or "first organic solvent" "or first extraction solvent" are meant a solvent, comprising one or more solvents, used to facilitate extraction of lipid from a fluid or from a lipid-containing biological organism in the fluid. This solvent will enter the fluid and remain in the fluid until being removed. Suitable first extraction solvents include solvents that extract or dissolve lipid, including but not limited to alcohols, hydrocarbons, amines, ethers, fluoroethers (including but not limited to fluoromethyl hexafluoroisopropyl ether (Sevoflurane)), surfactants, detergents, and combinations thereof. First extraction solvents may be combinations such as the following: 1) an alcohol and an ether; 2) an alcohol and a fluoroether; 3) an alcohol and a surfactant, 4) an ether and a surfactant; or 5) an alcohol, an ether and a surfactant. First extraction solvents include, but are not limited to n-butanol, di-isopropyl ether (DIPE), fluoroether such as sevoflurane, surfactants such as TRITON X-100™ (polyethylene glycol p-(1,1,3,3-tetramethylbutyl)-phenyl ether or polyoxyethylene octyl phenyl ether) or Tween 20™ (PEG (20)sorbitan monolaurate), diethyl ether, and combinations thereof.

The term "second extraction solvent" is defined as one or more solvents that may be employed to facilitate the removal of a portion of the first extraction solvent. Suitable second extraction solvents include any solvent that facilitates removal of the first extraction solvent from the fluid. Second extraction solvents include any solvent that facilitates removal of the first extraction solvent including but not limited to ethers, alcohols, hydrocarbons, amines, and combinations thereof. Preferred second extraction solvents include diethyl ether and di-isopropyl ether, which facilitate the removal of alcohols, such as n-butanol, from the fluid. The term "de-emulsifying agent" is a second extraction solvent that assists in the removal of the first solvent which may be present in an emulsion in an aqueous layer.

The term "delipidation" refers to the process of removing at least a portion of a total concentration of lipids in a fluid or in a lipid-containing organism. Lipid-containing organisms may be found within fluids which may or may not contain additional lipids.

The terms "pharmaceutically acceptable carrier" or "pharmaceutically acceptable vehicle" are used herein to mean any liquid including but not limited to water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The term "patient" refers to animals and humans.

The term "patient specific antigen" refers to an antigen that is capable of inducing a patient specific immune response when introduced into that patient. Such patient specific antigens may be viral antigens. A patient specific antigen includes any antigen, for example a viral antigen, that has been modified or influenced within the patient.

A Modified Viral Particle

Practice of the method of the present invention to reduce the lipid content of a virus creates a modified viral particle, particularly a coronavirus particle. These modified viral particles have lower levels of cholesterol and are immunogenic. The present methods expose epitopes that are not usually presented to the immune system by untreated virus. A structural change occurs in the modified viral particles, and proteins on, in, or near the surface of the virus are modified such that a conformational change occurs. Some of these proteins may also separate from the modified viral particle. The modified viral particle has a lower lipid content in the envelope, displays modified proteins, reduced infectivity and is immunogenic. Several embodiments of the delipidation methods provided herein do not lead to destruction of the viral envelope of the modified, partially delipidated immunogenic viral particles. A significant proportion of the viral envelopes are present following the partial delipidation. Thus, some embodiments of the partial delipidation methods provided herein result in partially delipidated particles comprising viral envelopes, including envelope proteins.

Modified Viral Particle Resulting from Removal of Lipid from Lipid-Containing Organisms Methods of the present invention solve numerous problems encountered with prior art methods. By substantially removing the lipid envelope of the virus, and keeping the viral particle intact, the method of the present invention exposes additional antigens. The host immune system recognizes the viral particle as foreign. Using the method of the present invention, what is created is a modified viral particle in which the antigenic core remains intact, thereby using the epitopes of the actual viral particle to initiate a positive immunogenic response in the patient into which it is reintroduced. In addition, the method of the present invention reduces the deleterious effect on the other plasma proteins, measured by protein recovery, such that the plasma can be reintroduced into the patient.

In creating this modified viral particle what is also created is a patient-specific antigen that induces protection against the viral particle in the species in which it is introduced. The method of the present invention creates an effective means to immunize individuals against viral pathogen infection and elicit a broad, biologically active protective immune response without risk of infecting the individual. New vaccines may be developed from certain lipid containing viruses by removing the lipid envelope and exposing antigens hidden beneath the envelope, in turn generating a positive immune response. These "autologous vaccines" can be created by the partial removal of the lipid envelope using suitable solvent systems (one which would not damage the antigens contained in the particle) exposing antigens and/or forcing a structural modification in the viral protein structures, which when introduced into the body, would provoke an effective immune response. Non-autologous vaccines are also created in the present invention which are administered to patients that are different from the source of the virus to be delipidated. Combination vaccines directed against multiple viruses are also within the scope of the present invention. Such combination vaccines may be made from various biological fluids, from stock supplies of multiple viruses (e.g., HIV, hepatitis and SARS virus) and/or from multiple strains or clades of a virus (e.g., SARS virus or HIV-1 and HIV-2).

Modified, partially delipidated viral particles obtained with some embodiments of the methods disclosed herein represent, in some aspects, new therapeutic vaccine compositions for therapeutic immunization and induction of an immune response in animals or humans. In one aspect, modified, partially delipidated viral particles obtained with the methods disclosed herein are useful for therapeutic immunization and induction of an immune response in animals or humans infected by a coronavirus. In one embodiment of the present invention, administration of the modified, partially delipidated viral particles and compositions comprising such particles provides a new method of treatment, alleviation, or attenuation of coronavirus infections, conditions or clinical symptoms associated with these infections such as those coronaviruses leading to the condition known as SARS.

Partially delipidated coronavirus viral particles obtained according to some of aspects of the present invention possess at least some structural characteristics that distinguish them from the conventional delipidated viruses. Such characteristics include, but are not limited to, the content of viral proteins, including viral envelope proteins or host viral membrane associated proteins, the cholesterol content of the partially delipidated viral particles, or the ratio of cholesterol content to viral protein. For example, a partially delipidated coronavirus viral particle according to some embodiments of the present invention has a lower cholesterol content than the cholesterol content of the non-delipidated coronavirus viral particle. In one embodiment, the lower cholesterol content of the partially delipidated coronavirus viral particle can be at least 20% to 30% lower than the cholesterol content of the non-delipidated coronavirus viral particle. In other embodiments, the cholesterol content in the modified, partially delipidated coronavirus viral particle is reduced, for example, no more than 80%, 60%, 55%, or 50% as compared to the unmodified viral particle. In other embodiments, the protein content in the modified, partially delipidated coronavirus viral particle is reduced, for example, no more than 5%, 10%, 15%, 20%, 30%, 40%, 50% or 55% as compared to the unmodified coronavirus viral particle. According to other embodiments, the modified, partially delipidated coronavirus viral particle has a ratio of µg of cholesterol relative to µg of total protein of at least 0.06.

Infectious Organisms Treated with the Present Invention

Viruses are the preferred infectious organism treated with the method of the present invention. Viral infectious organisms which may be delipidated by the present invention to form modified viral particles include, but are not limited to the lipid-containing viruses of the following genuses: Alphavirus (alphaviruses), Rubivurus (rubella virus), Flavivirus (Flaviviruses), Pestivirus (mucosal disease viruses), (unnamed, hepatitis C virus), Coronavirus, (Coronaviruses) severe acute respiratory syndrome (SARS), Torovirus, (toroviruses), Arteivirus, (arteriviruses), Paramyxovirus, (Paramyxoviruses), Rubulavirus (rubulavriuses), Morbillivirus (morbillivuruses), Pneumovirinae (the pneumoviruses), Pneumovirus (pneumoviruses), Vesiculovirus (vesiculoviruses), Lyssavirus (lyssaviruses), Ephemerovirus (ephemeroviruses), Cytorhabdovirus (plant rhabdovirus group A), Nucleorhabdovirus (plant rhabdovirus group B), Filovirus (filoviruses), Influenzavirus A, B (influenza A and B viruses), Influenza virus C (influenza C virus), (unnamed, Thogoto-like viruses), Bunyavirus (bunyaviruses), Phlebovirus (phleboviruses), Nairovirus (nairoviruses), Hantavirus (hantaviruses), Tospovirus (tospoviruses), Arenavirus (arenaviruses), unnamed mammalian type B retroviruses, unnamed, mammalian and reptilian type C retroviruses, unnamed, type D retroviruses, Lentivirus (lentiviruses), Spumavirus (spumaviruses), Orthohepadnavirus (hepadnaviruses of mammals), Avihepadnavirus (hepadnaviruses of birds), Simplexvirus (simplexviruses), Varicellovirus (varicelloviruses), Betaherpesvirinae (the cytomegaloviruses), Cytomegalovirus (cytomegaloviruses), Muromegalovirus (murine cytomegaloviruses), Roseolovirus (human herpes virus 6, 7, 8), Gammaherpesvirinae (the lymphocyte-associated herpes viruses), Lymphocryptovirus (Epstein-Barr-like viruses), Rhadinovirus (saimiri-ateles-like herpes viruses), Orthopoxvirus (orthopoxviruses), Parapoxvirus (parapoxviruses), Avipoxvirus (fowlpox viruses), Capripoxvirus (sheeppox-like viruses), Leporipoxvirus (myxomaviruses), Suipoxvirus (swine-pox viruses), Molluscipoxvirus (molluscum contagiosum viruses), Yatapoxvirus (yabapox and tanapox viruses), Unnamed, African swine fever-like viruses, Iridovirus (small iridescent insect viruses), Ranavirus (front iridoviruses), Lymphocystivirus (lymphocystis viruses of fish), Togaviridae, Flaviviridae, Coronaviridae, Enabdoviridae, Filoviridae, Paramyxoviridae, Orthomyxoviridae, Bunyaviridae, Arenaviridae, Retroviridae, Hepadnaviridae, Herpesviridae, Poxyiridae, and any other lipid-containing virus.

These viruses include the following human and animal pathogens: Ross River virus, fever virus, dengue viruses, Murray Valley encephalitis virus, tick-borne encephalitis viruses (including European and far eastern tick-borne encephalitis viruses, California encephalitis virus, St. Louis encephalitis virus, sand fly fever virus, human coronaviruses 229-E and OC43 and others causing the common cold, upper respiratory tract infection, probably pneumonia and possibly gastroenteritis), human parainfluenza viruses 1 and 3, mumps virus, human parainfluenza viruses 2, 4a and 4b, measles virus, human respiratory syncytial virus, rabies virus, Marburg virus, Ebola virus, influenza A viruses and influenza B viruses, Arenavirus: lymphocytic choriomeningitis (LCM) virus; Lassa virus, human immunodeficiency viruses 1 and 2, or any other immunodeficiency virus, hepatitis B virus, hepatitis C virus, hepatitis G virus, Subfamily: human herpes viruses 1 and 2, herpes virus B, Epstein-Barr virus), (smallpox) virus, cowpox virus, monkeypox virus, molluscum contagiosum virus, yellow fever virus, poliovirus, Norwalk virus, orf virus, and any other lipid-containing virus.

Methods of Manufacture of the Modified Viral Particle

One of ordinary skill in the art would appreciate that there may be multiple delipidation processes employed under the scope of this invention. In a preferred embodiment, a solvent system together with applied energy, for example a mechanical mixing system, is used to substantially delipidate the viral particle. The delipidation process is dependent upon the total amount of solvent and energy input into a system. Various solvent levels and mixing methods, as described below, may be used depending upon the overall framework of the process.

Exemplary Solvent Systems for Use in Removal of Lipid from Viruses and Effective in Maintaining Integrity of the Viral Particle The solvent or combinations of solvents to be employed in the process of partially or completely delipidating lipid-containing organisms may be any solvent or combination of solvents effective in solubilizing lipids in the viral envelope while retaining the structural integrity of the modified viral particle, which can be measured, in one embodiment, via protein recovery. A delipidation process falling within the scope of the present invention uses an optimal combination of energy input and solvent to delipidate the viral particle, while still keeping it intact. Suitable solvents comprise hydrocarbons, ethers, fluoroethers, alcohols, phenols, esters, halohydrocarbons, halocarbons, amines, detergents, surfactants, and mixtures thereof. Aromatic, aliphatic, or alicyclic hydrocarbons may also be used. Other suitable solvents, which may be used with the present invention, include amines and mixtures of amines. One solvent system is DIPE, either concentrated or diluted in water or a buffer such as a physiologically acceptable buffer. One solvent combination comprises alcohols and ethers. Another solvent comprises ether or combinations of ethers and a surfactant, such as polyethylene glycol p-(1,1,3,3-tetramethylbutyl)-phenyl ether (also known and referred to herein as TRITON X-100™ or polyoxyethylene octyl phenyl ether). Another solvent comprises ether or combinations of ethers, either in the form of symmetrical ethers, asymmetrical ethers or halogenated ethers such as fluoroethers.

Suitable first extraction solvents include solvents that extract or dissolve lipid, including but not limited to alcohols, hydrocarbons, amines, ethers, fluoroethers (including but not limited to fluoromethyl hexafluoroisopropyl ether (sevoflurane)), surfactants, detergents, and combinations thereof. First extraction solvents may be combinations such as the following: 1) an alcohol and an ether; 2) an alcohol and a fluoroether; 3) an alcohol and a surfactant, 4) an ether and a surfactant; or 5) an alcohol, an ether and a surfactant. First extraction solvents include, but are not limited to n-butanol, di-isopropyl ether (DIPE), fluoroether such as sevoflurane, surfactants such as TRITON X-100™ (polyethylene glycol p-(1,1,3,3-tetramethylbutyl)-phenyl ether or polyoxyethylene octyl phenyl ether) or Tween 20™ (PEG(20)sorbitan monolaurate), diethyl ether, and combinations thereof.

The optimal solvent systems are those that accomplish two objectives: first, at least partially delipidating the infectious organism or viral particle and second, employing a set of conditions such that there are few or no deleterious effects on the other plasma proteins. In addition, the solvent system should maintain the integrity of the viral particle such that it can be used to initiate an immune response in the patient. It should therefore be noted that certain solvents, solvent combinations, and solvent concentrations may be too harsh to use in the present invention because they result in a chemical kill.

It is preferred that the solvent or combination of solvents has a relatively low boiling point to facilitate removal through a vacuum and possibly heat without destroying the antigenic core of the viral particle. It is also preferred that the solvent or combination of solvents be employed at a low temperature because heat has deleterious effects on the proteins contained in biological fluids such as plasma. It is also preferred that the solvent or combination of solvents at least partially delipidate the viral particle.

Liquid hydrocarbons dissolve compounds of low polarity such as the lipids found in the viral envelopes of the infectious organisms. Particularly effective in disrupting the lipid membrane of a viral particle are hydrocarbons which are substantially water immiscible and liquid at about 37° C. Suitable hydrocarbons include, but are not limited to the following: $C_5$ to $C_{20}$ aliphatic hydrocarbons such as petroleum ether, hexane, heptane, octane; haloaliphatic hydrocarbons such as chloroform, 1,1,2-trichloro-1,2,2-trifluoroethane, 1,1,1-trichloroethane, trichloroethylene, tetrachloroethylene, dichloromethane and carbon tetrachloride; thioaliphatic hydrocarbons each of which may be linear, branched or cyclic, saturated or unsaturated; aromatic hydrocarbons such as benzene; ketones; alkylarenes such as toluene; haloarenes; haloalkylarenes; and thioarenes. Other suitable solvents may also include saturated or unsaturated heterocyclic compounds such as pyridine and aliphatic, thio- or halo-derivatives thereof.

Suitable esters for use in the present invention include, but are not limited to, ethyl acetate, propylacetate, butylacetate and ethylpropionate. Suitable detergents/surfactants that may be used include but are not limited to the following: sulfates, sulfonates, phosphates (including phospholipids), carboxylates, and sulfosuccinates. Some anionic amphiphilic materials useful with the present invention include but are not limited to the following: sodium dodecyl sulfate (SDS), sodium decyl sulfate, bis-(2-ethylhexyl) sodium sulfosuccinate (AOT), cholesterol sulfate and sodium laurate.

Solvents may be removed from delipidated viral mixtures through the use of additional solvents. For example, demulsifying agents such as ethers may be used to remove a first solvent such as an alcohol from an emulsion. Removal of solvents may also be accomplished through other methods, which do not employ additional solvents, including but not limited to the use of charcoal. Charcoal may be used in a slurry or alternatively, in a column to which a mixture is applied. Charcoal is a preferred method of removing solvents. Pervaporation may also be employed to remove one or more solvents from delipidated viral mixtures.

Examples of suitable amines for use in removal of lipid from lipid-containing organisms in the present invention are those which are substantially immiscible in water. Typical amines are aliphatic amines—those having a carbon chain of at least 6 carbon atoms. A non-limiting example of such an amine is $C_6H_{13}NH_2$.

Ether is a preferred solvent for use in the method of the present invention. Particularly preferred are the $C_4$-$C_8$ containing-ethers, including but not limited to ethyl ether, diethyl ether, and propyl ethers (including but not limited to di-isopropyl ether (DIPE)). Asymmetrical ethers may also be employed. Halogenated symmetrical and asymmetrical ethers may also be employed. Fluoroethers including but not limited to fluoromethyl hexafluoroisopropyl ether may also be employed. Halogenated symmetrical and asymmetrical ethers, such as fluoroethers may be employed alone or in combination with other solvents in different ratios such as (sevoflurane:DIPE ratios of 0.01 parts sevoflurane to 99.99 parts DIPE to 60 parts sevoflurane to 40 parts DIPE, with a specific ratio range of about 10 parts sevoflurane to 90 parts DIPE to 5 parts sevoflurane to 95 parts DIPE, with a specific ratio range of about 10 parts sevoflurane to 90 parts DIPE to 50 parts sevoflurane to 50 parts DIPE, with a specific ratio range of about 20 parts sevoflurane to 80 parts DIPE to 45 parts sevoflurane to 55 parts DIPE, with a specific range of about 25 parts sevoflurane to 75 parts DIPE.

Low concentrations of solvents, such as ethers, may be employed to remove lipids when used alone and not in combination with other solvents. For example, a low concentration range of solvents, such as ethers includes but is not limited to 0.5% to 30%, 0.01% to 10%, 0.01% to 5%, 0.1% to 5%, 0.01% to 2%, or 0.1% to 2%, or any number within these ranges. Specific concentrations of solvents, such as ethers, that may be employed include, but are not limited to the following: 0.1%, 0.625%, 1.0% 1.25%, 2%, 2.5%, 3.0%, 3.5%, 5.0% and 10% or higher. It has been observed that dilute solutions of solvents, such as ethers, are effective. Such solutions may be aqueous solutions or solutions in aqueous buffers, such as phosphate buffered saline (PBS). Other physiological buffers may be used, including but not limited to bicarbonate, citrate, Tris, Tris/EDTA, and Trizma. Preferred ethers are di-isopropyl ether (DIPE) and diethyl ether (DEE). Low concentrations of ethers may also be used in combination with alcohols, for example, n-butanol.

When used in the present invention, appropriate alcohols are those which are not appreciably miscible with plasma or other biological fluids. Such alcohols include, but are not limited to, straight chain and branched chain alcohols, including pentanols, hexanols, heptanols, octanols and those alcohols containing higher numbers of carbons.

When alcohols are used in combination with another solvent, for example, an ether, a hydrocarbon, an amine, or a combination thereof, $C_1$-$C_8$ containing alcohols may be used. Alcohols for use in combination with another solvent include $C_4$-$C_8$ containing alcohols. Accordingly, alcohols that fall within the scope of the present invention are butanols, pentanols, hexanols, heptanols and octanols, and iso forms thereof, in particular, $C_4$ alcohols or butanols (1-butanol and 2-butanol). The specific alcohol choice is dependent on the second solvent employed.

Ethers and alcohols can be used in combination as a first solvent for treating the fluid containing the lipid-containing virus, or viral particle. Any combination of alcohol and ether may be used provided the combination is effective to at least partially remove lipid from the infectious organism, without having deleterious effects on the plasma proteins. In one embodiment, lipid is removed from the viral envelope of the infectious organism. When alcohols and ether are combined as a first solvent for treating the infectious organism contained in a fluid, ratios of alcohol to ether in this solvent range from about 0.01 parts alcohol to 99.99 parts ether to 60 parts alcohol to 40 parts ether, with a specific ratio range of about 10 parts alcohol to 90 parts ether to 5 parts alcohol to 95 parts ether, with a specific ratio range of about 10 parts alcohol to 90 parts ether to 50 parts alcohol to 50 parts ether, with a specific ratio range of about 20 parts alcohol to 80 parts ether to 45 parts alcohol to 55 parts ether, with a specific range of about 25 parts alcohol to 75 parts ether.

One combination of alcohol and ether is the combination of butanol and di-isopropyl ether (DIPE). When butanol and DIPE are combined as a first solvent for treating the infectious organism contained in a fluid, ratios of butanol to DIPE in this solvent are about 0.01 parts butanol to 99.99 parts DIPE to 60 parts butanol to 40 parts DIPE, with a specific ratio range of about 10 parts butanol to 90 parts DIPE to 5 parts butanol to 95 parts DIPE, with a specific ratio range of about 10 parts butanol to 90 parts DIPE to 50 parts butanol to 50 parts DIPE, with a specific ratio range of about 20 parts butanol to 80 parts DIPE to 45 parts butanol to 55 parts DIPE, with a specific range of about 25 parts butanol to 75 parts DIPE.

Another combination of alcohol and ether is the combination of butanol with diethyl ether (DEE). When butanol is used in combination with DEE as a first solvent, ratios of butanol to DEE are about 0.01 parts butanol to 99.99 parts DEE to 60 parts butanol to 40 parts DEE, with a specific ratio range of about 10 parts butanol to 90 parts DEE to 5 parts butanol to 95 parts DEE with a specific ratio range of about 10 parts butanol to 90 parts DEE to 50 parts butanol to 50 parts DEE, with a specific ratio range of about 20 parts butanol to 80 parts DEE to 45 parts butanol to 55 parts DEE, with a specific range of about 40 parts butanol to 60 parts DEE. This combination of about 40% butanol and about 60% DEE (vol:vol) has been shown to have no significant effect on a variety of biochemical and hematological blood parameters, as shown for example in U.S. Pat. No. 4,895,558.

Surfactants such anionic and nonionic surfactants may also be employed alone or together with other solvents. Nonionic surfactants are known to one of ordinary skill in the art and may include without limitation surfactants known as Triton, for example TRITON X-100™ (polyethylene glycol p-(1,1,3,3-tetramethylbutyl)-phenyl ether or polyoxyethylene octyl phenyl ether), Tweens such as Tween 20™ (PEG(20)sorbitan monolaurate), or Pluronic™ (block copolymers based on ethylene oxide and propylene oxide). When employed alone, or together with other solvents such as ethers or lower order alcohols, for example DIPE or n-butanol or combinations thereof, surfactants may be used in concentrations of from 0.001% to 1%, 0.07% to 0.8%, 0.05% to 0.5%, or 0.03% to 0.3%.

Biological Fluids and Treatment Thereof for Reducing Infectivity of Infectious, Lipid-Containing Organisms As stated above, various biological fluids may be treated with the method of the present invention in order to reduce the levels of infectivity of the lipid-containing organism in the biological fluid and to create modified viral particles. In a preferred embodiment, plasma obtained from an animal or human is treated with the method of the present invention in order to reduce the concentration and/or infectivity of lipid-containing infectious organisms, such as coronavirus viral particles, within the plasma and to create modified coronavirus viral particles. In this embodiment, plasma may be obtained from an animal or human patient by withdrawing blood from the patient using well-known methods and treating the blood in order to separate the cellular components of the blood (red and white cells) from the plasma. Such methods for treating the blood are known to one of ordinary skill in the art and include but are not limited to centrifugation and filtration. One of ordinary skill in the art understands the proper centrifugation conditions for separating such lipid-containing organisms from the red and white cells. Use of the present invention permits treatment of lipid-containing organisms, for example those found within plasma, without having deleterious effects on other plasma proteins and maintaining the integrity of the viral core.

Viruses in the plasma are affected by the treatment of the plasma with the method of the present invention. The lipid-containing viral organism may be separated from the red and white cells using techniques known to one of ordinary skill in the art.

Biological fluids include stocks of viral preparations including various strains of viruses as well as different types of viruses. Treatment of such biological fluids with the method of the present invention produces modified viral particles that may be administered to a patient as a non-autologous vaccine. Such non-autologous vaccines provide protection in the patient against more than strain of a virus and/or against more than one type of virus. Treatment of lipid-containing organisms may occur in biological fluids other than blood and plasma. For example, peritoneal fluid may be treated with the present invention to affect the levels and infectivity of lipid-containing organisms without deleterious effects on protein components. The treated fluid may subsequently be reintroduced into the animal or human from which it was obtained. Treatment of non-blood types of fluids affects the lipid-containing organisms in the fluid, such as the virus.

Once a biological fluid, such as plasma, is obtained either in this manner, or for example, from a storage facility housing bags of plasma, the plasma is contacted with a first organic solvent, as described above, capable of solubilizing lipid in the lipid-containing infectious organism. The first organic solvent is combined with the plasma in a ratio wherein the first solvent is present in an amount effective to substantially solubilize the lipid in the infectious organism, for example, dissolve the lipid envelope that surrounds the virus. Exemplary ratios of first solvent to plasma (expressed as a ratio of first organic solvent to plasma) are described in the following ranges: 0.5-4.0:0.5-4.0; 0.8-3.0:0.8-3.0; and 1-2:0.8-1.5. Various other ratios may be applied, depending on the nature of the biological fluid. For example, in the case of cell culture fluid, the following ranges may be employed of first organic solvent to cell culture fluid: 0.5-4.0:0.5-4.0; 0.8-3.0:0.8-3.0; and 1-2:0.8-1.5.

After contacting the fluid containing the infectious organism with the first solvent as described above, the first solvent and fluid are mixed, using methods including but not limited to one of the following suitable mixing methods: gentle stirring; vigorous stirring; vortexing; swirling; homogenization; and, end-over-end rotation.

The amount of time required for adequate mixing of the first solvent with the fluid is related to the mixing method employed. Fluids are mixed for a period of time sufficient to permit intimate contact between the organic and aqueous phases, and for the first solvent to at least partially or completely solubilize the lipid contained in the infectious organism. Typically, mixing will occur for a period of about 10 seconds to about 24 hours, possibly about 10 seconds to about 2 hours, possibly approximately 10 seconds to approximately 10 or 20 minutes, or possibly about 30 seconds to about 1 hour, depending on the mixing method employed. Non-limiting examples of mixing durations associated with different methods include 1) gentle stirring and end-over-end rotation for a period of about 10 seconds to about 24 hours, 2) vigorous stirring and vortexing for a period of about 10 seconds to about 30 minutes, 3) swirling for a period of about 10 seconds to about 2 hours, or 4) homogenization for a period of about 10 seconds to about 10 minutes.

Separation of Solvents

After mixing of the first solvent with the fluid, the solvent is separated from the fluid being treated. The organic and aqueous phases may be separated by any suitable manner known to one of ordinary skill in the art. Since the first solvent is typically immiscible in the aqueous fluid, the two layers are permitted to separate and the undesired layer is removed. The undesired layer is the solvent layer containing dissolved lipids and its identification, as known to one of ordinary skill in the art, depends on whether the solvent is more or less dense than the aqueous phase. An advantage of separation in this manner is that dissolved lipids in the solvent layer may be removed.

In addition, separation may be achieved through means, including but not limited to the following: removing the undesired layer via pipetting; centrifugation followed by removal of the layer to be separated; creating a path or hole in the bottom of the tube containing the layers and permitting the lower layer to pass through; utilization of a container with valves or ports located at specific lengths along the long axis of the container to facilitate access to and removal of specific layers; and any other means known to one of ordinary skill in the art. Another method of separating the layers, especially when the solvent layer is volatile, is through distillation under reduced pressure or evaporation at room temperature, optionally combined with mild heating. In one embodiment employing centrifugation, relatively low g forces are employed, such as 900×g for about 5 to 15 minutes to separate the phases.

A preferred method of removing solvent is through the use of charcoal, preferably activated charcoal. This charcoal is optionally contained in a column. Alternatively the charcoal may be used in slurry form. Various biocompatible forms of charcoal may be used in these columns. Pervaporation methods and use of charcoal to remove solvents are preferred methods for removing solvent.

Following separation of the first solvent from the treated fluid, some of the first solvent may remain entrapped in the aqueous layer as an emulsion. A preferred method of removing a first solvent or a demulsifying agent is through the use of adsorbants, such as charcoal. The charcoal is preferably activated charcoal. This charcoal is optionally contained in a column, as described above. Still another method of removing solvent is the use of hollow fiber contactors. Pervaporation methods and charcoal adsorbant methods of removing solvents are preferred. In yet another embodiment, a de-emulsifying agent is employed to facilitate removal of the trapped first solvent. The de-emulsifying agent may be any agent effective to facilitate removal of the first solvent. A preferred de-emulsifying agent is ether and a more preferred de-emulsifying agent is diethyl ether. The de-emulsifying agent may be added to the fluid or in the alternative the fluid may be dispersed in the de-emulsifying agent. In vaccine preparation, alkanes in a ratio of about 0.5 to 4.0 to about 1 part of emulsion (vol:vol) may be employed as a de-emulsifying agent, followed by washing to remove the residual alkane from the remaining delipidated organism used for preparing the vaccine. Preferred alkanes include, but are not limited to, pentane, hexane and higher order straight and branched chain alkanes.

The de-emulsifying agent, such as ether, may be removed through means known to one of skill in the art, including such means as described in the previous paragraph. One convenient method to remove the de-emulsifying agent, such as ether, from the system, is to permit the ether to evaporate from the system in a running fume hood or other suitable device for collecting and removing the de-emulsifying agent from the environment. In addition, de-emulsifying agents may be removed through application of higher temperatures, for example from about 24 to 37° C. with or without pressures of about 10 to 20 mbar. Another method to remove the de-emulsifying agent involves separation by centrifugation, followed by removal of organic solvent through aspiration, further followed by evaporation under reduced pressure (for example 50 mbar) or further supply of an inert gas, such as nitrogen, over the meniscus to aid in evaporation.

Methods of Treating Biological Fluids (Delipidation)

It is to be understood that the method of the present invention may be employed in either a continuous or discontinuous manner. That is, in a continuous manner, a fluid may be fed to a system employing a first solvent which is then mixed with the fluid, separated, and optionally further removed through application of a de-emulsifying agent. The continuous method also facilitates subsequent return of the fluid containing delipidated infectious organism to a desired location. Such locations may be containers for receipt and/or storage of such treated fluid, and may also include the vascular system of a human or animal or some other body compartment of a human or animal, such as the pleural, pericardial, peritoneal, and abdominopelvic spaces.

In one embodiment of the continuous method of the present invention, a biological fluid, for example, blood, is removed from an animal or a human through means known to one of ordinary skill in the art, such as a catheter. Appropriate anti-clotting factors as known to one of ordinary skill in the art are employed, such as heparin, ethylenediaminetetraacetic acid (EDTA) or citrate. This blood is then separated into its cellular and plasma components through the use of a centrifuge. The plasma is then contacted with the first solvent and mixed with the first solvent to effectuate lipid removal from the infectious organism contained within the plasma. Following separation of the first solvent from the treated plasma, charcoal, pervaporation or a de-emulsifying agent is optionally employed to remove entrapped first solvent. After ensuring that acceptable levels (non-toxic) of first solvent or de-emulsifying agent, if employed, are found within the plasma containing the delipidated infectious organism, the plasma is then optionally combined with the cells previously separated from the blood to form a new blood sample containing at least partially delipidated viral particles, also called modified viral particles herein.

Through the practice of this method, the infectivity of the infectious organism is greatly reduced or eliminated. Following recombination with the cells originally separated from the blood, the fluid with reduced lipid levels and containing virus with reduced lipid levels may be reintroduced into either the vascular system or some other system of the human or animal. The effect of such treatment of plasma removed from the human or animal and return of the sample containing the partially or completely delipidated infectious organism, or modified viral particle, to the human or animal causes a net decrease in the infectivity of the infectious organism contained within the vascular system of the human or animal. The modified viral particle also serves to initiate an autologous immune response in the patient when administered to the patient. In this mode of operation, the method of the present invention is employed to treat body fluids in a continuous manner—while the human or animal is connected to an extracorporeal device for such treatment.

In yet another embodiment, the discontinuous or batch mode, the human or animal is not connected to an extracorporeal device for processing bodily fluids with the method of the present invention. In a discontinuous mode of operation, the present invention employs a fluid previously obtained from a human or animal, which may include, but is not limited to plasma, lymphatic fluid, or follicular fluid. The fluid may be contained within a blood bank or in the alternative, drawn from a human or animal prior to application of the method. The fluid may be a reproductive fluid or any fluid used in the process of artificial insemination or in vitro fertilization. The fluid may also be one not directly obtained from a human or animal but rather any fluid containing a potentially infectious organism, such as cell culture fluid. Stocks of various strains or clades of a virus and also stocks of multiple viruses may be used in the present method to produce vaccines. In this mode of operation, this fluid is treated with the method of the present invention to produce a new fluid with reduced lipid levels which contains at least partially or completely delipidated infectious organisms, or modified viral particles. One embodiment of this mode of the present invention is to treat plasma samples previously obtained from other animals or humans and stored in a blood bank for subsequent transfusion. This is a non-autologous method of providing vaccine protection. These samples may be treated with the method of the present invention to treat or prevent one or more infectious disease, such as SARS, HIV, hepatitis, and/or cytomegalovirus, from the biological sample.

Delipidation of an infectious organism can be achieved by various means. A batch method can be used for fresh or stored biological fluids, for example, fresh frozen plasma. In this case a variety of the described organic solvents or mixtures thereof can be used for viral inactivation. Extraction time depends on the solvent or mixture thereof and the mixing procedure employed.

Through the use of the methods of the present invention, levels of lipid in lipid-containing viruses in a fluid are reduced, and the fluid, for example, delipidated plasma containing the modified viral particles may be administered to the patient. Such fluid contains modified viral particles with reduced infectivity, act as a vaccine and provide protection in the patient against the virus or provide a treatment in an infected patient by generating an immune response and decreasing the severity of the disease. These modified viral particles induce an immune response in the recipient to exposed epitopes on the modified viral particles. Alternatively the modified viral particles may be combined with a pharmaceutically acceptable carrier, and optionally an adjuvant, and administered as a vaccine composition to a human or an animal to induce an immune response in the recipient.

Vaccine Production

In one embodiment, the modified viral particle, which is at least partially or substantially delipidated and has immunogenic properties, is optionally combined with a pharmaceutically acceptable carrier to make a composition comprising a vaccine. In a preferred embodiment, the modified viral particle is retained in the biological fluid, such as plasma, with reduced lipid levels and is administered to a patient as a vaccine. This vaccine composition is optionally combined with an adjuvant or an immunostimulant and administered to an animal or a human. Both autologous and non-autologous vaccines, including combination vaccines, are within the scope of the present invention. It is to be understood that vaccine compositions may contain more than one type of modified viral particle or component thereof, in order to provide protection against more than one strain of a virus or more than one viral disease after vaccination. Such combinations may be selected according to the desired immunity. For example, preferred combinations include, but are not limited to SARS and HIV, SARS and influenza, and SARS and hepatitis. More specifically, the vaccine can comprise a plurality of modified viral particles having patient-specific antigens and modified viral particles having non-patient specific antigens or stock viral particles that have undergone the delipidation process of the present invention. The remaining modified viral particles of the organism are retained in the delipidated biological fluid, and when reintroduced into the animal or human, are presumably ingested by phagocytes and generate an immune response.

Administration of Vaccine Produced with the Method of the Present Invention

When a delipidated infectious organism, for example one in the form of a modified viral particle with exposed antigenic determinants, is administered to an animal or a human, it is optionally combined with a pharmaceutically acceptable carrier to produce a vaccine, and optionally combined with an adjuvant or an immunostimulant as known to one of ordinary skill in the art. The vaccine formulations may conveniently be presented in unit dosage form and may be prepared by conventional pharmaceutical techniques known to one of ordinary skill in the art. Such techniques include uniformly and intimately bringing into association the active ingredient and the liquid carriers (pharmaceutical carrier(s) or excipient(s)). Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers—for example, sealed ampules and vials—and may be stored in a freeze-dried (lyophilized) condition requiring only the addition of the sterile liquid carrier, for example, water for injections, immediately prior to use. The vaccine may be stored at temperatures of from about 4° C. to −100° C. The vaccine may also be stored in a lyophilized state at different temperatures including room temperature. Extemporaneous injection solutions and suspensions may be prepared from sterile powders, granules and tablets commonly used by one of ordinary skill in the art. The vaccine may be sterilized through conventional means known to one of ordinary skill in the art. Such means include, but are not limited to filtration, radiation and heat. The vaccine of the present invention may also be combined with bacteriostatic agents, such as thimerosal, to inhibit bacterial growth.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The vaccine may be administered through different routes, such as oral, including buccal and sublingual, rectal, parenteral, aerosol, nasal, intramuscular, subcutaneous, intradermal, intravenous, intraperitoneal, and topical. The vaccine may also be administered in the vicinity of lymphatic tissue, for example through administration to the lymph nodes such as axillary, inguinal or cervical lymph nodes.

The vaccine of the present invention may be administered in different forms, including but not limited to solutions, emulsions and suspensions, microspheres, particles, microparticles, nanoparticles, and liposomes. It is expected that from about 1 to 5 dosages may be required per immunization regimen. One of ordinary skill in the medical or veterinary arts of administering vaccines will be familiar with the amount of vaccine to be administered in an initial injection and in booster injections, if required, taking into consideration, for example, the age and size of a patient. Initial injections may range from about less than 1 ng to 1 gram based on total viral protein. A non-limiting range may be 1 ml to 10 ml. The volume of administration may vary depending on the administration route.

Vaccination Schedule

The vaccines of the present invention may be administered before, during or after an infection. The vaccine of the present invention may be administered to either humans or animals. In one embodiment, the viral load (one or more viruses) of a human or an animal may be reduced by delipidation treatment of the plasma. The same individual may receive a vaccine directed to the one or more viruses, thereby stimulating the immune system to combat against the virus that remains in the individual. The time for administration of the vaccine before initial infection is known to one of ordinary skill in the art. However, the vaccine may also be administered after initial infection to ameliorate disease progression or to treat the disease.

Adjuvants

A variety of adjuvants known to one of ordinary skill in the art may be administered in conjunction with the modified viral particles in the vaccine composition. Such adjuvants include, but are not limited to the following: polymers, co-polymers such as polyoxyethylene-polyoxypropylene co-polymers, including block co-polymers; polymer P1005; monotide ISA72; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; water-in-oil mixtures, water-in-oil-in-water mixtures or combinations thereof.

Suspending Fluids and Carriers

A variety of suspending fluids or carriers known to one of ordinary skill in the art may be employed to suspend the vaccine composition. Such fluids include without limitation: sterile water, saline, buffer, or complex fluids derived from growth medium or other biological fluids. Preservatives, stabilizers and antibiotics known to one of ordinary skill in the art may be employed in the vaccine composition.

The following experimental examples are illustrative in showing that a delipidation process of the viral particle occurred and in particular, that the viral particle was modified and noted to exhibit a positive immunogenic response in the species from which it was derived. It will be appreciated that other embodiments and uses will be apparent to those skilled in the art and that the invention is not limited to these specific illustrative examples or preferred embodiments.

Example 1

Development of a Modified Coronavirus Viral Particle for Use as a Vaccine

Solvent treatment technology was used to develop a modified coronavirus viral particle to use as a prophylactic vaccine against the SARS virus. In addition, solvent-treated virus that was subsequently subjected to chemical inactivation was tested for the ability to raise neutralizing antibodies and produce a cellular immune response in mice. In the following text and elsewhere in the application, the coronavirus that produces SARS is also referred to as SARS.

The SARS stocks used in the experiments were propagated at the Lovelace Respiratory Research Institute (LRRI), Albuquerque, N. Mex., in the laboratory of Dr. Kevin Harrod, Director of the Infectious Disease Program. The initial SARS seed stock was provided by the Centers for Disease Control (CDC). Supernatants from SARS infected VERO cells were then sent to Dr. Erdman at the CDC for inactivation by gamma irradiation.

The delipidation process was optimized using Mouse Hepatitis Virus (MHV), provided by Dr. Katherine Holmes at the University of Colorado-Health Sciences Center. Dr. Holmes provided a seed stock of MHV as well as the permissive cell line MHV-A59.

Seven different delipidation methods were developed using MHV. The methods were characterized based on the amount of cholesterol removed (measured by the Amplex Red Cholesterol Assay), and protein recovery. Three of these methods were selected for use in in vivo mouse immunization studies using gamma irradiated SARS. Dr. Erdman at the Center for Disease Control gamma irradiated a stock of SARS with 5×106 rads, and certified its inactivation. 1) 3% diisopropyl ether (DIPE) with end-over-end mixing 20 min at room temperature resulted in 80% cholesterol removal, and 85% SARS nucleocapsid (NC) recovery, 2) DIPE/Butanol (n-BuOH) (75:25) at a ratio of 99:1 SARS to solvent (vol:vol) with end-over-end mixing for 20 min at room temperature resulted in 44% cholesterol removal and 80% NC recovery, 3) DIPE/TRITON X-100™ (polyethylene glycol p-(1,1,3,3-tetramethylbutyl)-phenyl ether or polyoxyethylene octyl phenyl ether) (3%/0.05%) end-over-end mixing for 20 min at room temperature resulted in 60% cholesterol removal and 85% NC recovery.

Western blot analysis of the delipidated SARS from each of the three procedures confirmed the presence of SARS NC and SARS envelope specific protein (Spike—S). S protein mediates the receptor binding and membrane fusion process mediated by S protein, indicating that major viral proteins are present after the delipidation procedure. (Gallagher, T. M. & Buchmeier, M. J. (2001) *Virology* 279: 371-374). This data was similar to the initial optimization data obtained from delipidating MHV.

In summary, three unique delipidation processes optimized for inactivated SARS were developed. Gamma-irradiated SARS was used for safety reasons and because gamma irradiation was known not to damage the viral structure of SARS or its antigenicity. Inactivated SARS was structurally similar to live SARS as visualized by ultrastructural analysis (kindly preformed by Dr. Humphrey at the CDC), and by previous findings that gamma irradiation did not affect the structural integrity or antigenicity of SARS, since gamma irradiated VERO-E6 cells that were infected with SARS could be used for immunofluorescence assays (Ksiazek T G et al., 2003 *N. Engl. J. Med.* 348:1953-1966). Thus, inactivated SARS was used to test the utililty of delipidation in enhancing immunogenicity of SARS vaccine. To determine the immunogenicity of the delipidated SARS in vivo, a series of in vivo mouse experiments were performed.

Experiment #1: Evaluation of Delipidation Methods for SARS

The experiments tested the effects of different delipidation methods on the ability of the delipidated and inactivated SARS to generate an immune response. The experiment was designed with four mice per group. Three groups were tested:
 a) Inactivated purified SARS treated with 3% DIPE;
 b) Inactivated purified SARS treated with DIPE/n-BuOH;
 c) Inactivated purified SARS treated with DIPE/TRITON X-100™ (polyethylene glycol p-(1,1,3,3-tetramethylbutyl)-phenyl ether or polyoxyethylene octyl phenyl ether).

Mice were vaccinated subcutaneously (sc) with 50 ug of inactivated purified delipidated SARS in incomplete Freund's Adjuvant in a 50 ul volume in one footpad. SARS was propagated at Lovelace Respiratory Research Institute (LRRI) by Dr. Kevin Harrod, and virions were purified by Lipid Sciences, Inc.). At three weeks post vaccination, mice were sacrificed, and serum was harvested.

Serum aliquots were analyzed by Dr. Michael W. Cho at Case Western Reserve University, where SARS neutralization titers were established. Dr. Cho's laboratory has established a novel and very reliable neutralization assay for SARS using pseudotyped murine leukemia virus (MuLV) with the Spike protein of SARS-coronavirus (CoV) (or vesicular stomatitis virus-G protein (VSV-G) as a negative control) as previously described (Han et al., 2004 *Virology*. 326:140-149). SARS NC and Spike antibody titers were performed at Lipid Sciences, Inc. using recombinant SARS NC and Spike purchased from Virolabs, Inc (NJ).

Results: SARS-CoV-specific neutralizing activities were detected in all three groups above, although the antibody levels were low, possibly because mice only received one vaccination. Of the three groups, however, mice vaccinated with SARS delipidated with the DIPE/TRITON X-100™ (polyethylene glycol p-(1,1,3,3-tetramethylbutyl)-phenyl ether or polyoxyethylene octyl phenyl ether) method exhibited slightly higher neutralization of >50% compared to the other two groups which averaged about 40%. Antibody titers for SARS Spike Protein were similar in all three groups, while the SARS NC titers were higher in mice vaccinated with SARS delipidated with 3% DIPE. Therefore, the "optimal" delipidation was chosen to be the DIPE/TRITON X-100™ (polyethylene glycol p-(1,1,3,3-tetramethylbutyl)-phenyl ether or polyoxyethylene octyl phenyl ether) method.

Experiment #2: Dose Escalation Study of Optimally Delipidated SARS Vaccine

This experiment tested three different concentrations of delipidated inactivated purified SARS in comparison to inactivated purified SARS only, at 0.1 ug, 1 ug, and 10 ug boosts, in a prime-boost vaccine model, with the aim of enhancing the humoral immune response observed in Experiment #1. Mice were primed with SARS supernatant obtained from LRRI in Incomplete Freunds Adjuvant sc with 100 ug total protein. Two weeks later, mice were boosted with the appropriate concentration of DIPE/TRITON X-100™ (polyethylene glycol p-(1,1,3,3-tetramethylbutyl)-phenyl ether or polyoxyethylene octyl phenyl ether) delipidated SARS, or inactivated SARS. Four weeks after the boost, mice were sacrificed and serum collected and sent to Dr. Cho for determination of neutralizing antibody titers. Serum IgG titers to SARS NC and Spike were performed at Lipid Sciences, Inc.

Results: Both the inactivated virus and the delipidated inactivated virus were able to boost neutralizing activity. There were no significant differences in either the neutralizing antibody titers or anti-Spike/NC antibody titers, between mice boosted with DIPE/TRITON X-100™ (polyethylene glycol p-(1,1,3,3-tetramethylbutyl)-phenyl ether or polyoxyethylene octyl phenyl ether) delipidated, inactivated SARS virus and mice boosted with inactivated SARS virus.

These two studies established that the delipidation process did not result in major structural damage to the virus. Immunogenicity was maintained in the delipidated inactivated virions, since the neutralizing antibody titers were not affected by the delipidation. Based upon these results, a 10 ug dose was tested as the boost concentration in Experiment #3.

Experiment #3: Determining the Cell-Mediated Immune Responses in Mice Boosted with Optimally Delipidated Vaccines The experiment tested the cell-mediated immune responses generated by vaccination with delipidated, inactivated SARS at a concentration of 10.0 ug. The experiment was designed with four mice per group in the following four groups:

1) Boost with inactivated SARS that was treated with DIPE/TRITON X-100™ (polyethylene glycol p-(1,1,3,3-tetramethylbutyl)-phenyl ether or polyoxyethylene octyl phenyl ether);
2) Boost with inactivated SARS;
3) Primed only; and
4) No prime/no boost.

All mice in groups 1, 2, and 3 were primed with the same SARS supernatant obtained from LRRI, as per Experiment #2. Mice were injected two weeks post priming, and sacrificed one week after the booster injection since cell mediated immune responses in mice peak at about one week after the booster injection. Cell-mediated immune responses were measured using murine interferon-gamma (IFN-γ) ELISPOT Assay, per manufacturer's protocol (MABTech). Cells were incubated with pools of peptides covering the entire SARS CoV NC and Spike proteins.

The following reagent was obtained through the NIH Biodefense and Emerging Infections Research Resources Repository, NIAID, NIH: SARS Overlapping Peptide Array, NR-143. Pools of peptides (eight peptides per pool, 13- to 20-mers with approximately 10 amino acid overlaps) were generated and used in the enzyme-linked immunosorbent spot (ELISPOT Assay: Czerkinsky C, et al., (1983) "A solid-phase enzyme-linked immunospot (ELISPOT) assay for enumeration of specific antibody-secreting cells". *J Immunol Methods* 65 (1-2): 109-21.).

Results: Mice boosted with delipidated, inactivated SARS had enhanced immune responses to Spike and NC peptide pools compared to booster injection with inactivated SARS. There was a boosting effect observed, compared to the no-boost Group. Booster injections with delipidated, inactivated SARS enhanced cell-mediated immune response, but did not change the antibody titers of Spike and NC.

Conclusion: The above findings indicate that delipidated/inactivated SARS generated better cell mediated immune responses than a preparation of inactivated SARS alone. The enhanced cell-mediated immune responses may greatly assist in preventing establishment of infection due to the broad epitope recognition in recipients primed with our vaccine.

Production of mouse neutralizing antibodies was measured with a neutralization assay for SARS using pseudotyped murine leukemia virus (MuLV) expressing the Spike protein of SARS-CoV (or VSV-G as a negative control) as previously described (Han et al., 2004 *Virology.* 326:140-149). Cell mediated immune responses were measured using ELISPOT Assays for IFN-γ. ELISPOT Assays have been used extensively for measuring cell mediated immune responses in several different disease models.

The experiments demonstrated the utility of the delipidation process in creating a SARS vaccine: 1) capable of triggering a strong cell-mediated immune response; 2) of increased efficacy; and 3) usable separately or as a part of a component vaccine. In addition, this delipidation process is easy to perform and easily scaled for commercial production.

Experimental Protocols: Optimization of solvent and chemical treatment for SARS coronavirus and evaluation of native viral protein structure and viral envelope changes post treatment MHV & SARS Viral Purification MHV Growth and Purification:

MHV-A59, the MHV permissive cell line 17CL.1, and AO4 (a polyclonal goat anti-MHV antibody), were kindly provided by Dr. Kathryn Holmes, University of Colorado Health Sciences. MHV was propagated in 17CL.1 and purified according to Sturman, et al. (*J. Virol* 1980 33:449-462). Briefly, viral supernatant was precipitated using polyethylene glycol (PEG, Sigma, St. Louis, Mo.) at a final concentration of 10%, incubated for 15 min at room temperature (RT), and pelleted at 10,000×g for 1 hr at 4° C. The pellet was resuspended in 4 ml of tris-maleate buffer (TME, Sigma, St. Louis, Mo.), pH 6.0, and layered on top of the 20%-55% sucrose gradient layer. Virus was pelleted by spinning at 32,000 rpm for 4 hr at 4° C. in a 80 Ti rotor (Beckman Coulter, Fullerton, Calif.). Aliquots (0.4 ml) were collected from the bottom of the tube, and quantitated using the Biorad Total Protein Assay (Biorad, Hercules, Calif.).

SARS Growth and Purification:

SARS CoV-Utah strain was obtained from the Centers for Disease Control (CDC). SARS permissive cell line VERO-E6 stock was obtained from ATCC Inc. SARS was propagated in VERO-E6 cells in the laboratory of Dr. Kevin Harrod, Lovelace Respiratory Research Institute (LRRI), Albuquerque, N. Mex., and purified using a modified MHV purification protocol, in which SARS supernatant was not PEG precipitated. SARS supernatant was directly layered on top of a 20%-55% sucrose gradient layer, and pelleted at 32,000 rpm for 4 hr at 4° C. in a 80 Ti rotor (Beckman Coulter, Fullerton, Calif.). Aliquots (0.4 ml) were collected from the bottom of the tube, and analyzed using both the SARS Ag ELISA kit (MedQuick Testing, SimiValley, Calif.) and the Biorad Total Protein Assay kit (Biorad, Hercules, Calif.).

SARS ELISA:

To quantify the amount of SARS antigen, a SARS-CoV-Ag ELISA kit (MedQuick Testing, SimiValley, Calif.) targeting SARS NC protein, was used according to the manufacturer's instructions.

Cholesterol Assay:

Cholesterol in the viral fractions was analyzed by the Amplex Red Total Cholesterol Assay according to manufacturer's protocol (Molecular Probes, Eugene, Oreg.).

Western Blot:

MHV Western Blot:

For both Western blot and Coomasie staining, 10% SDS-PAGE gels (Biorad, Hercules, Calif.) were used. Samples were loaded at 7 ul (concentration of 2 mg/ml) and 7 ul of 2× loading dye with 2-mercaptoethanol (2-ME, Sigma, St. Louis, Calif.). The gels were run at 220 V constant voltage for 1 hr. The Western blot gel was transferred to a nitrocellulose membrane (Biorad, Hercules, Calif.), and blocked with 5% milk and 0.1% Tween-20 (Sigma, St. Louis, Mo.) in a tris-glycine buffer (Biorad, Hercules, Calif.). The primary antibody AO4 (goat anti-MHV Ab) was used at 1:2000 dilution. The secondary antibody was a rabbit anti-goat horseradish peroxidase (HRP) (Sigma, St. Louis, Mo.) used at 1:5000 dilution. A colorimetric substrate diaminobenzidine (DAB) Enhanced Liquid Substrate System for Membrane ELISA, Sigma, St. Louis, Mo.) for HRP was used for Western blot development.

SARS Western Blot:

For both Western blot and Coomasie staining, 10% SDS-PAGE gels (Biorad, Hercules, Calif.) were used. Samples were loaded at 7 ul (concentration of 2 mg/ml) and 7 ul of 2× loading dye with 2-mercaptoethanol (2-ME, Sigma, St. Louis, Mo.). The gels were run at 220 V constant voltage for 1 hr. The Western blot gel was transferred to a nitrocellulose membrane (Biorad, Hercules, Calif.), and blocked with 5% milk and 0.1% Tween-20 (Sigma, St. Louis, Mo.) in a tris-glycine buffer (Biorad, Hercules, Calif.). The primary antibody solution was a cocktail of mouse monoclonal antibodies against SARS Spike and NC (Imgenex, San Diego, Calif.). Positive controls for Spike and NC (Virolabs, Chantilly, Va.) were run at 3.5 ug each. The secondary antibody, a goat anti-mouse-HRP polyclonal antibody (Sigma, St. Louis, Mo.) was used at a dilution of 1:5000. A chemiluminescent substrate (ECL+, Amersham BioSciences, Piscataway, N.J.) for HRP was used for Western blot development. The membrane was developed on a Kodak MS Film (Eastman Kodak, Rochester, N.Y.).

MHV Delipidation Procedures.

A total of seven different delipidation matrices were developed, using MI-IV as a surrogate for SARS, due to SARS material constraints:

1. Diisopropylether (DIPE, VWR, West Chester, Pa.) 17 ul/ml, end-over-end (EOE) mixing for 20 min at room temperature (RT). Solvent was removed by passing the mixture through an activated charcoal column.

2. DIPE and n-butanol (n-BuOH, VWR, West Chester, Pa.) at a 95:5 mixture and at a 99:1 virus:solvent ratio (vol:vol), 20 min EOE mixing at RT. Solvent was removed by passing the mixture through an activated charcoal column.

3. DIPE and n-butanol (n-BuOH) at a 95:5 mixture and at a 99:1 virus:solvent ratio (vol:vol), vortexed at high speed for 15 sec at RT. Solvent was removed by passing the mixture through an activated charcoal column.

4. BuOH and sevoflurane (Abbott Labs, Abbott Park, Ill.) at a 75:25 mixture and at a 1:2 virus:solvent ratio (vol:vol), vortexed high speed for 15 sec, with gravity separation at RT. The aqueous layer was removed. Solvent was removed by passing the mixture through an activated charcoal column.

5. A final concentration of 3% D 5 IPE and 0.05% TRITON X-100™ (polyethylene glycol p-(1,1,3,3-tetramethylbutyl)-phenyl ether or polyoxyethylene octyl phenyl ether), EOE mixing for 20 min at RT. Solvent was removed by passing the mixture through an activated charcoal column.

6. A final concentration of 3% DIPE, EOE mixing for 20 min at RT. Solvent was removed by passing the mixture through an activated charcoal column.

7. A final concentration of 0.05% TRITON X-100™ (polyethylene glycol p-(1,1,3,3-tetramethylbutyl)-phenyl ether or polyoxyethylene octyl phenyl ether) (Sigma, St. Louis, Mo.), EOE mixing for 20 min at RT. Solvent was removed by passing the mixture through an activated charcoal column.

SARS Delipidation Procedure:

The three delipidation procedures selected for SARS delipidation experiments were:

1. DIPE and n-butanol (n-BuOH) at a 95:5 mixture and at a 99:1 virus:solvent ratio (vol:vol), 20 min EOE with mixing at RT. Solvent was removed by passing the mixture through an activated charcoal column.

2. A final concentration of 3% DIPE and 0.05% TRITON X-100™ (polyethylene glycol p-(1,1,3,3-tetramethylbutyl)-phenyl ether or polyoxyethylene octyl phenyl ether), EOE mixing for 20 min at RT. Solvent was removed by passing the mixture through an activated charcoal column.

3. A final concentration of 3% DIPE, EOE mixing for 20 min at RT. Solvent was removed by passing the mixture through an activated charcoal column.

Electron Microscopy:

Electron micrographs (EMs) of γ-irradiated SARS were made by Dr. Dean Erdman and Dr. Charles Humphrey at the CDC. SARS supernatants containing about $1\times10^6$ PFU/ml were gamma irradiated with $5\times10^6$ rads, and certified inactivated by Dr. Dean Erdman.

Results

TABLE 1

Optimization of delipidation protocol using MHV as a surrogate for SARS

| | Solvent | Percent Protein Recovered | Percent Cholesterol Removed |
|---|---|---|---|
| 1 | DIPE | 80.26 | 39.20 |
| 2 | DIPE:n-Butanol, EOE | 91.43 | 43 |
| 3 | DIPE:n-Butanol, vortex | 85.1 | 31 |
| 4 | n-Butanol: Sevoflurane | 48.32 | ND* below detection level |
| 5 | DIPE:TRITON X-100™ (polyethylene glycol p-(1,1,3,3-tetramethylbutyl)-phenyl ether or polyoxy-ethylene octyl phenyl ether) | 70.95 | 70.35 |
| 6 | DIPE (3%) | 75.45 | 70 |
| 7 | TRITON X-100™ (polyethylene glycol p-(1,1,3,3-tetramethylbutyl)-phenyl ether or polyoxy-ethylene octyl phenyl ether) (0.05%) | 78.02 | 25.5 |

Table 1 summarizes the data obtained from the seven delipidations performed on MHV, a surrogate for SARS. Protein recoveries post-delipidation were >70%, except for n-BuOH: Sevoflurane delipidated virus, where the recovery was 48%.

The following three delipidation protocols were used on purified SARS virus:

1. DIPE and n-butanol (n-BuOH) at a 95:5 mixture and at a 99:1 virus:solvent ratio (vol:vol), 20 min EOE, RT. Solvent was removed by passing the mixture through an activated charcoal column. This is protocol #2 in Table 1.
2. A final concentration of 3% DIPE and 0.05% TRITON X-100™ (polyethylene glycol p-(1,1,3,3-tetramethylbutyl)-phenyl ether or polyoxyethylene octyl phenyl ether), EOE 20 min at RT. Solvent was removed by passing the mixture through an activated charcoal column. This is protocol#5 in Table 1.
3. A final concentration of 3% DIPE, EOE 20 min at RT. Solvent was removed by passing the mixture through an activated charcoal column. This is protocol #6 in Table 1.

TABLE 2

Protein and Cholesterol Results: SARS delipidation methods

| Solvent | Percent Nucleocapsid Recovered | Percent Cholesterol Removed |
| --- | --- | --- |
| 1 DIPE (3%) | 85 | 80 |
| 2 DIPE:Triton X-100 DIPE/TRITON X-100™ (polyethylene glycol p-(1,1,3,3-tetramethylbutyl)-phenyl ether or polyoxyethylene octyl phenyl ether) | 85 | 60 |
| 3 DIPE:n-Butanol (95:5) | 80 | 44 |

Table 2 summarizes the data obtained from the three chosen delipidation methods performed on SARS. The protein recoveries as measured by the SARS ELISA detecting SARS NC were all ≧80%. The cholesterol removal was similar to those observed in MHV, as seen in Table 1.

FIG. 1 illustrates a Western Blot performed on delipidated MHV as discussed in Table 1. The polyclonal anti-MHV antibody AO4 was kindly provided by Dr. Kathryn Holmes. All lanes show positive reactivity with the anti-MHV Ab. The Western Blot for samples delipidated by method #1, and #3 of the delipidation matrix in Table 1 also showed the same patterns of staining as the DIPE: triton delipidated SARS (data not shown).

Figure 2:
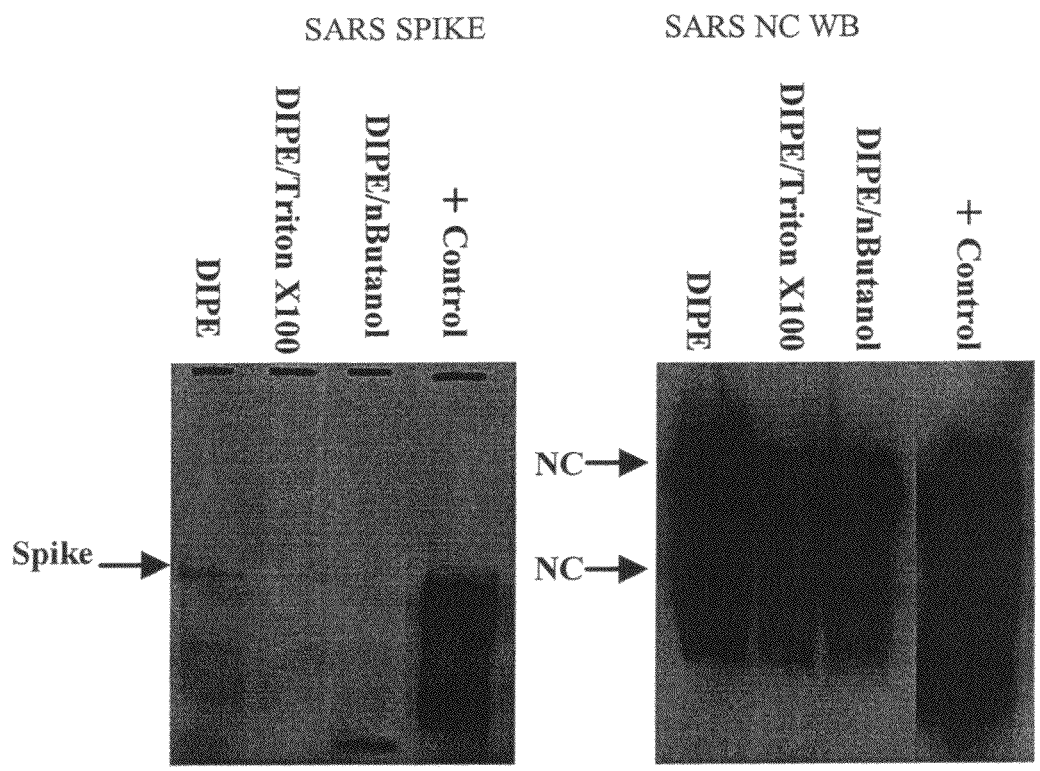
FIG. 2 shows Western Blots of SARS Spike and SARS nucleocapsid (NC) proteins post delipidation with various solvent conditions, as indicated.

FIG. 2 shows Western Blots of SARS Spike and SARS NC proteins post delipidation. Lanes 1-3 correspond to samples 1-3 in the SARS delipidation methods listed in Table 2 above. Lane 4 is purified SARS Spike and NC proteins from Virolabs. Spike reactivity is seen in 3% DIPE delipidated SARS, while very strong reactivity to NC was observed in all three delipidation protocols. The primary antibodies used in SARS Western blots were monoclonal antibodies.

Figure 3:
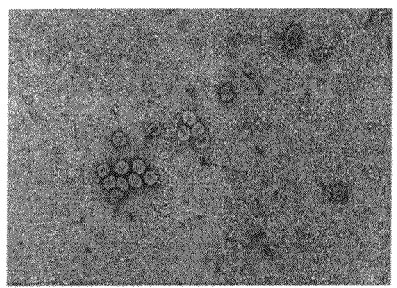
FIG. 3 representative electron micrographs of γ-irradiated SARS.
Figure 3:
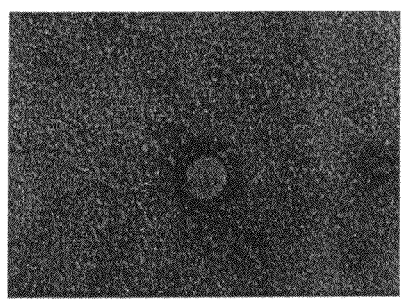

FIG. 3 shows representative electron micrographs of γ-irradiated SARS The EMs of virus pre- and post-irradiation were not significantly different. The picture on the right, a magnification of 23000×, has a typical SARS CoV appearance. The Spike proteins are clearly seen on the membrane, and the morphology is consistent with those of SARS CoV.

Discussion

By using MHV as a surrogate for SARS, seven different delipidation protocols were evaluated, as listed in Table 1. The n-BuOH/sevoflurane method clearly elicited major structural damage, as inferred by the protein recovery. Western blot analysis of the various delipidated MHV (FIG. 1) showed that viral proteins were intact and immunogenic. No significant loss of viral proteins was seen in any of the delipidation methods, except the sevoflurane:n-BuOH delipidated samples. Protocols 1, 3, 4, and 7 (Table 1) were eliminated due to the low percentage of cholesterol removal.

Three delipidation protocols were tested on purified SARS CoV as listed in Table 2. Western blot analysis of the various delipidated SARS samples showed that reactivity to SARS NC was very strong in all delipidated samples. Viruses delipidated with 3% DIPE showed readily detectable reactivity to SARS Spike protein, while the other two samples did not.

Ultrastructural analyses were performed on irradiated SARS supernatant to determine the effects of irradiation on the viral structure. It was confirmed that the cultures were SARS CoV and that irradiation did not significantly alter the virion structure. The results indicated development of three unique delipidation methods for SARS CoV, which were tested for their in vivo immunogenicity.

Testing the Ability of Solvent and Chemically Treated Virions to Produce an Immune Response The ability of solvent and chemically treated SARS virions to produce an immune response was examined by:
A. Vaccinating mice with solvent and chemically treated SARS virions;
B. Testing for production of mouse neutralizing antibodies in serum using Vero E6 cell cytopathic assay; and,
C. Evaluating mouse cellular response to vaccination with solvent-treated SARS virions.

The immunogenicity of delipidated SARS in vivo, in a murine model was tested. Three experimental protocols were used:
1) Evaluation of three Different Delipidation Methods for SARS;
2) Dose Escalation Study of Optimally Delipidated SARS Vaccine; and,
3) Determining The Cell-Mediated Immune Responses in Mice Boosted with Optimally Delipidated Vaccines.

Experiment #1 Evaluation of three Different Delipidation Methods for SARS

The particles obtained by three delipidation processes were tested with respect to generating an immune response. The experiment was designed with three mice per group testing the following three groups:
A. Inactivated SARS treated with 3% DIPE;
B. Inactivated SARS treated with DIPE/n-BuOH (95:5); and,
C. Inactivated SARS treated with 3% DIPE/0.05% TRITON X-100™ (polyethylene glycol p-(1,1,3,3-tetramethylbutyl)-phenyl ether or polyoxyethylene octyl phenyl ether).

Mice were vaccinated sc with 50 μg of inactivated delipidated SARS in 50 μA in one footpad. At three weeks post vaccination, mice were sacrificed, and serum was harvested.

Serum aliquots were sent to the laboratory of Dr. Michael W. Cho (Case Western Reserve University), where SARS neutralization titers were evaluated using a neutralization assay for SARS using pseudotyped murine leukemia virus (MuLV) with the Spike protein of SARS-CoV (or VSV-G as a negative control) as previously described (Han et al., 2004 *Virology.* 326:140-149). SARS NC and Spike antibody titers were performed at Lipid Sciences, Inc. using recombinant SARS NC and Spike purchased from Virolabs, Inc (NJ)

Materials and Methods

Pseudotyped SARS Neutralization Assay:

Neutralization assays were performed using pseudotyped MuLV with Spike protein of SARS-CoV (or VSV-G as negative control) as previously described (Han et al., *Virology.* 326: 140-149). Briefly, VERO-E6 cells were used for the pseudovirus infection and were plated at $0.5 \times 10^4$ cells per well in a 96-well plate one day before infection. Heat-inactivated plasma samples at indicated dilutions were incubated with 100 infectious units of pseudoviruses. The control and experimental samples of each dilution were then dispensed to the triplicate wells containing the VERO-E6 cells for 1 hr at 37° C. After removing the serum:virus mix, cells were further incubated in DMEM with 5% FBS at 37° C. in a 5% $CO_2$ incubator for 1.5 days. To determine the neutralization activity, the Beta-Glo assay system (Promega, Madison, Wis.) was used according to manufacturer's protocol. Cells were washed with PBS, and lysed with 100 µl of Report Lysis Buffer. 75 µl of cell lysates and 75 µl of Beta-Glo reagent were mixed in a white-walled plate. The mixtures were incubated for 30 min at RT and measured using a luminometer (Biorad, Hercules, Calif.).

SARS Spike and NC Antibody Titers:

Serum samples were titrated for antibodies to viral epitopes using routine EIA analysis. Briefly, high protein binding ELISA micro plates (Fisher, Pittsburgh, Pa.) were incubated with 1 µg purified recombinant SARS Spike or SARS NC protein (Virolabs, Chantilly, Va.) overnight in standard bicarbonate coating buffer, pH 9.6 at 4° C. Following three washes with PBS/Tween 20, the plates were blocked for 1 hr at RT with PBS containing 5% normal goat serum (Sigma, St. Louis, Mo.). Serial 1:5 dilutions of the sera to be tested in PBS containing 5% normal goat serum starting at 1:500, were added to the wells for 1 hr at RT. After washing the unbound antibodies, the plates were incubated with an HRP-anti mouse IgG conjugate at 1:5000 (Sigma, St. Louis, Mo.), and developed using tetramethylbenzidine (TMB) substrate (Sigma, St. Louis, Mo.). Plates were read at a 405 nm wavelength using an ELISA plate reader (Molecular Devices, Sunnyvale, Calif.).

ELISPOT Assay:

Mouse interferon-gamma (IFN-γ) ELISPOT assays were performed using splenocytes to determine the cell-mediated immune responses generated post-vaccination with delipidated SARS. Briefly, 96 well Millipore ELLIP 10SSP multiscreen plates (Millipore, Billerica, Mass.) were coated with 100 µl anti-mouse IFN-γ capturing antibody (MABTECH, Cincinnati, Ohio, monoclonal Ab clone AN-18). The capturing Ab was diluted to 10 mg/ml in sterile PBS. Plates were blocked with 150 µl/well of 10% RPMI (RPMI 1640 containing; 10% FBS, 10 mM HEPES buffer, 2 mM glutamine, 0.5 mg/ml gentamicin, and 50 mM 2-mercaptoethanol) and the plates incubated at room temperature for at least 2 hours. The peptide pools mentioned above were added directly to wells in a volume of 50 µl and then freshly isolated splenocytes were added at a concentration of $10^5$ cells/well in 50 µl of 10% RPMI media. The final concentration of the peptides in the screening assay was 10 mM. Plates were incubated for three days at 5% $CO_2$ at 37° C. washed and 100 µl/well of 2 mg/ml biotinylated anti-IFN-γ mAb (clone R4-6A2, MABTECH, Cincinnati, Ohio) in PBS were added and incubated at room temperature for 3 h, followed by 100 µl/well avidin peroxidase conjugate (APC) for 1 hr. After washing, ELISPOTs were developed using the Vectastain ABC Kit (Vector Laboratories, Burlingame, Calif.) according to manufacturer's protocol. The number of spots/$10^5$ cells/well in the ELISPOT plates were read in a plate reader in the Vanderbilt University Core Facility, Nashville, Tenn.

Results

Figure 4:
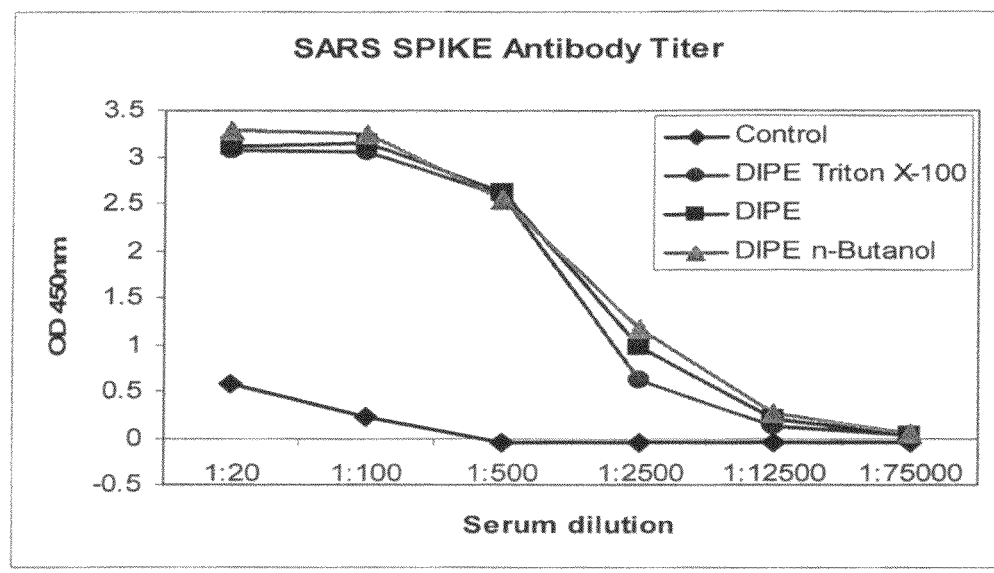
FIG. 4 illustrates the total IgG antibody titers against SARS CoV Spike and NC post delipidation with various solvent conditions, as indicated.
Figure 4:
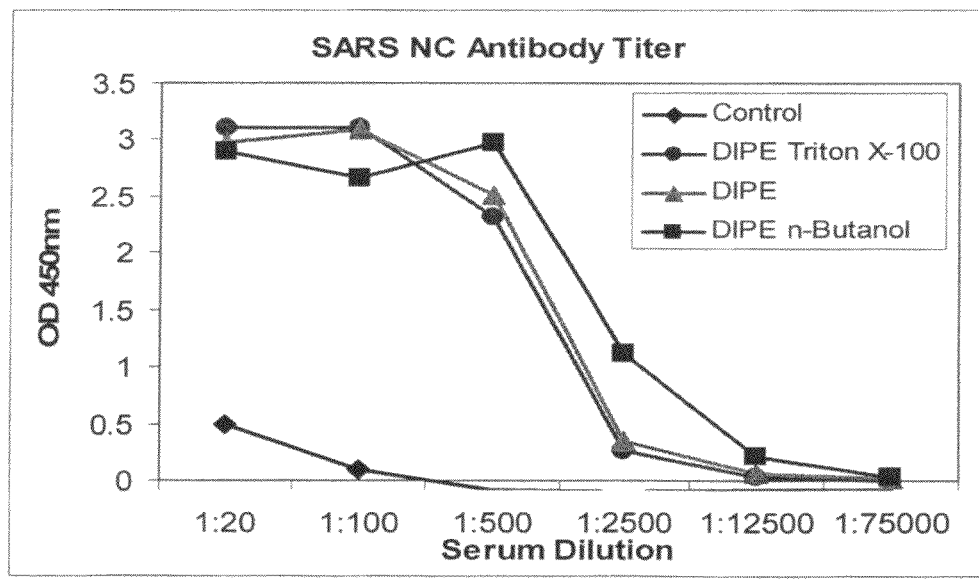

FIG. 4 illustrates the total IgG antibody titers against SARS CoV Spike and NC. The titers obtained from all three delipidated virus vaccines were similar for both Spike and NC. Although mice vaccinated with DIPE:n-BuOH showed slightly higher NC titers, the differences were not significant. Data reflect mean O.D. (standard deviation of <10%). IgM specific titers for all samples were at an O.D. of <1.0 indicating the presence of very low IgM antigen specific antibodies (data not shown).

Figure 5:
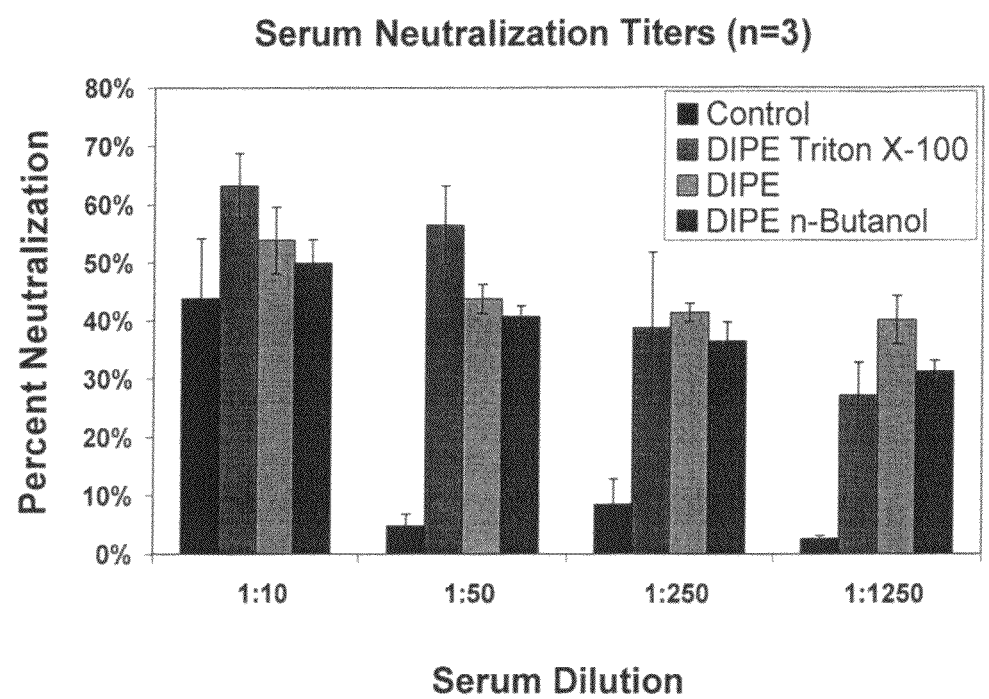
FIG. 5 illustrates the SARS neutralization titers in sera from mice vaccinated with SARS delipidated with various solvent conditions, as indicated.

FIG. 5 illustrates the SARS neutralization titers, performed by Dr. Michael Cho. Sera from mice vaccinated with DIPE/TRITON X-100™ (polyethylene glycol p-(1,1,3,3-tetramethylbutyl)-phenyl ether or polyoxyethylene octyl phenyl ether) treated SARS showed slightly better titers than mice vaccinated with SARS treated with the other delipidation protocols. SARS-CoV-specific neutralizing activities were detected in the sera from all three groups above. The overall antibody levels were low, possibly because mice only received one vaccination. Of the three groups, however, mice vaccinated with SARS delipidated with the DIPE/TRITON X-100™ (polyethylene glycol p-(1,1,3,3-tetramethylbutyl)-phenyl ether or polyoxyethylene octyl phenyl ether) method exhibited slightly higher neutralization of >50% compared to the other two groups which averaged at about 40%.

The DIPE/TRITON X-100™ (polyethylene glycol p-(1,1,3,3-tetramethylbutyl)-phenyl ether or polyoxyethylene octyl phenyl ether) delipidation method was used in Experiment #2, where we performed a titration of three concentrations of DIPE/TRITON X-100™ (polyethylene glycol p-(1,1,3,3-tetramethylbutyl)-phenyl ether or polyoxyethylene octyl phenyl ether) delipidated SARS vaccine of 0.1 µg, 1 µg, and 10 µg of protein, as discussed below.

Experiment #2 SARS-Dose Escalation Study of Optimally Delipidated SARS Vaccine

The objective of this study was to test three different concentrations of delipidated inactivated purified SARS with inactivated purified SARS only, at 0.1 µg, 1 µg, and 10 µg boosts. Mice (3 mice/group) were primed with SARS supernatant (virus was unpurified) obtained from LRRI that was γ-irradiated by Dr. Erdman at the CDC and had a protein concentration of 4 mg/ml. Mice were primed using Incomplete Freunds Adjuvant sc with 100 µg total protein in a volume of 500 µl. Two weeks later, mice were boosted with the appropriate concentration of delipidated SARS, or inactivated SARS in a volume of 500 µl administered sc. Four weeks after the booster injection, mice were sacrificed and serum collected and sent to Dr. Cho for neutralizing antibody titers. Serum IgG titers to SARS NC and Spike were performed at Lipid Sciences, Inc.

Results

Figure 6:
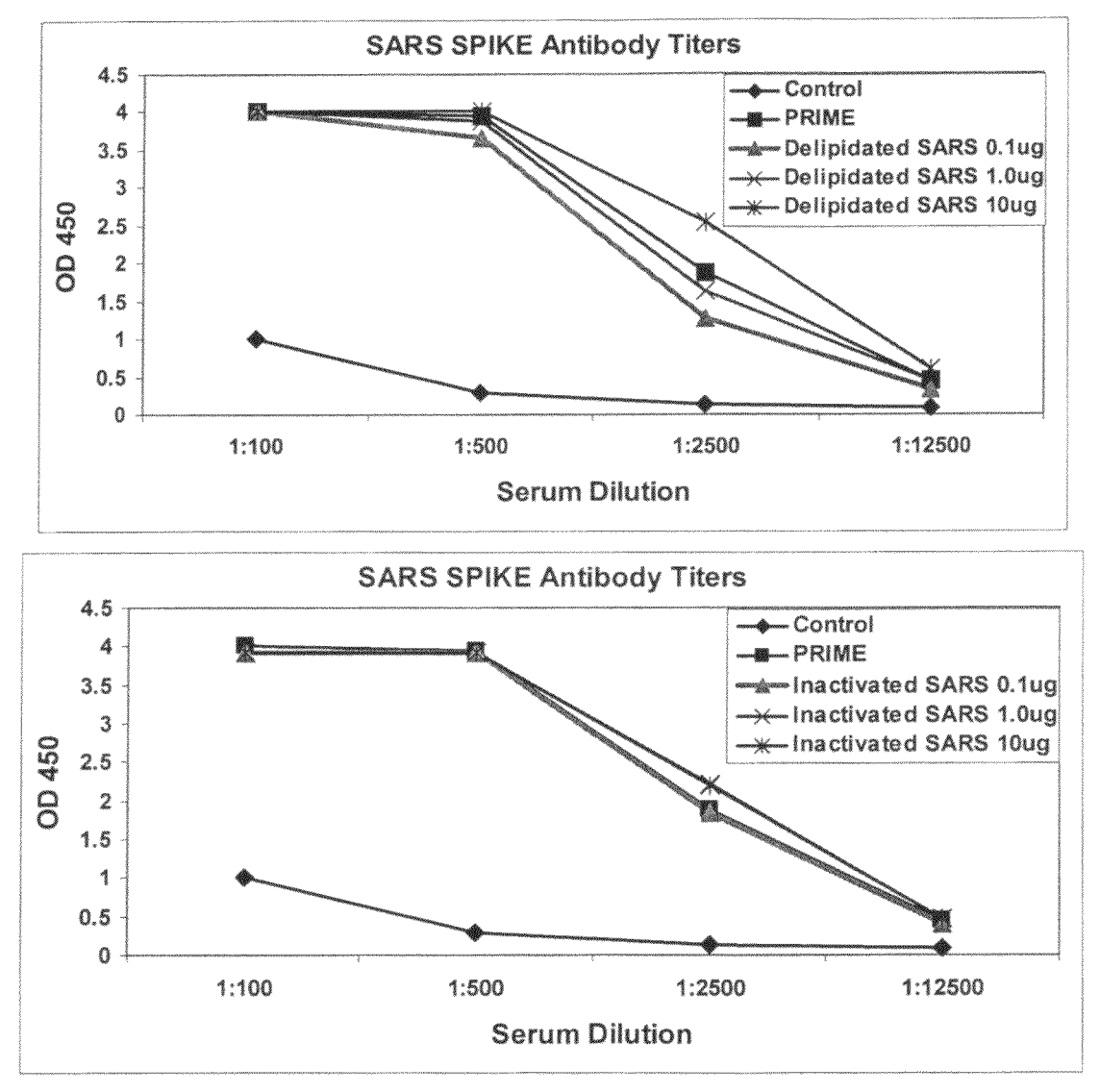
Figure 7:
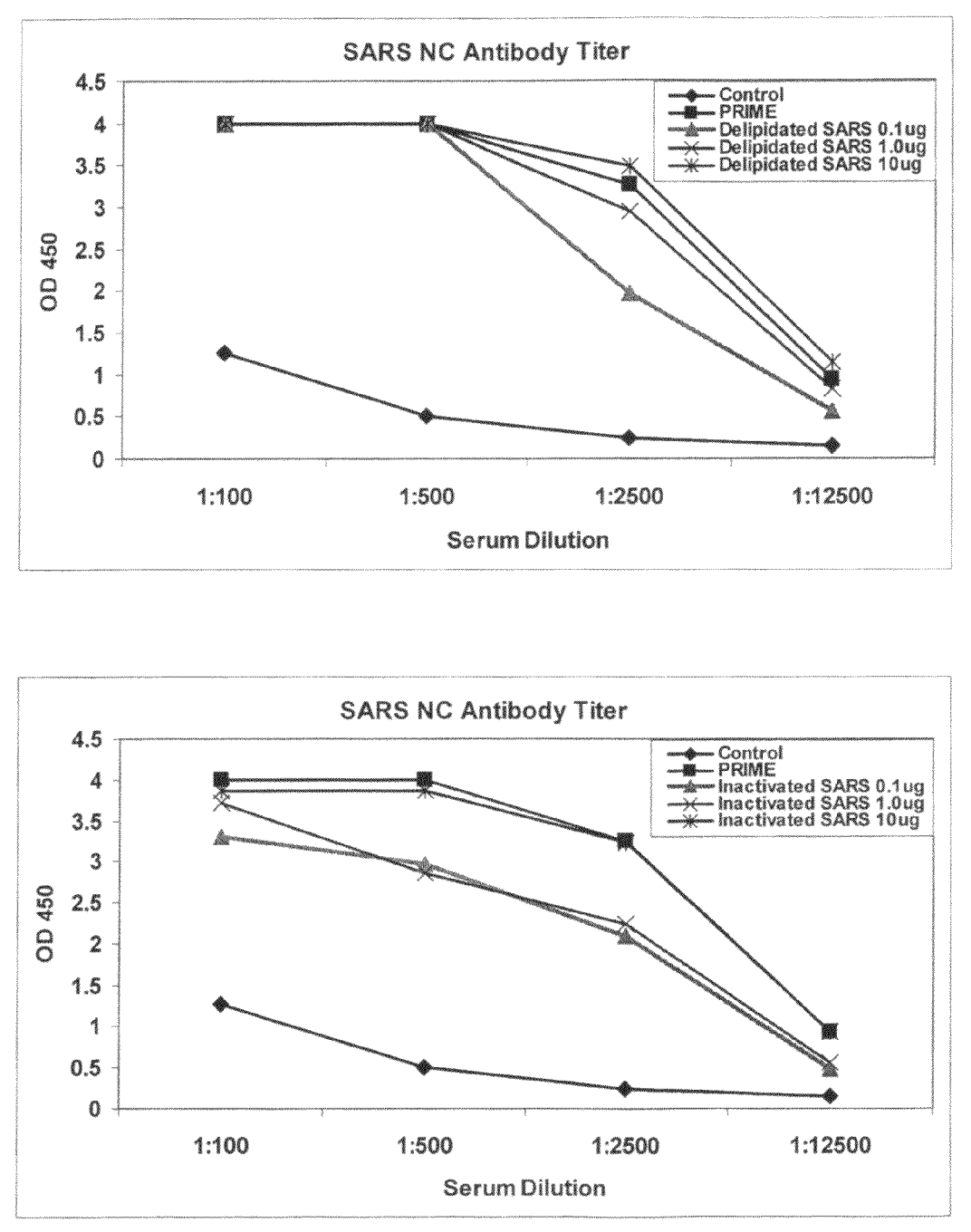

FIG. 6 illustrates the Spike Ab titers from Experiment #2, comparing the titers in mice vaccinated with delipidated SARS to those in mice vaccinated with inactivated SARS. FIG. 7 illustrates the NC Ab titers comparing the titers in mice vaccinated with delipidated SARS to those in mice vaccinated with inactivated SARS. A clear increase in Ab titers was observed for both antigens with the 10 µg booster injection. The Spike and NC titers in delipidated SARS boost showed a clear dose-response. The titers obtained from inactivated SARS boost showed a clear enhancement in titers following the 10 µg boost. However, the overall patterns of Ab titers in both groups were surprisingly similar. When comparing the overall Ab titers to mice primed only, the patterns were similar as well. IgM specific titers for all samples were at an O.D. of <1.0 indicating the presence of very low IgM antigen specific antibodies (data not shown).

Figure 8:
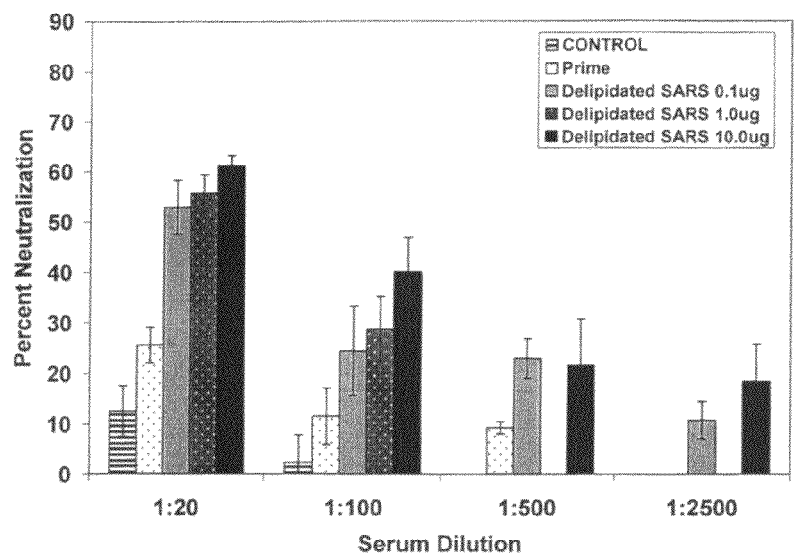
FIG. 8 illustrates the neutralization titers comparing the titers in mice vaccinated with delipidated SARS to mice vaccinated with inactivated SARS.
Figure 8:
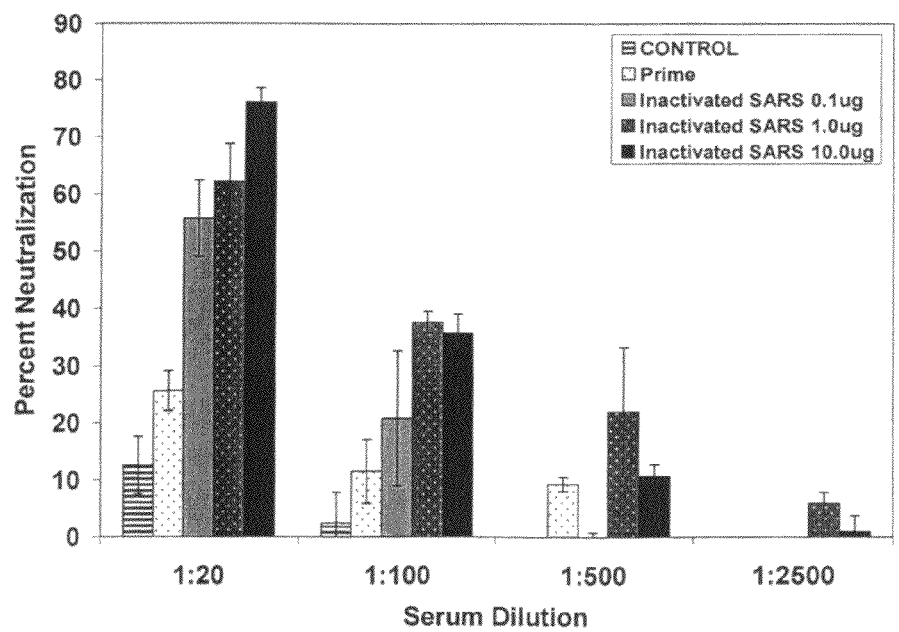
Figure 10:
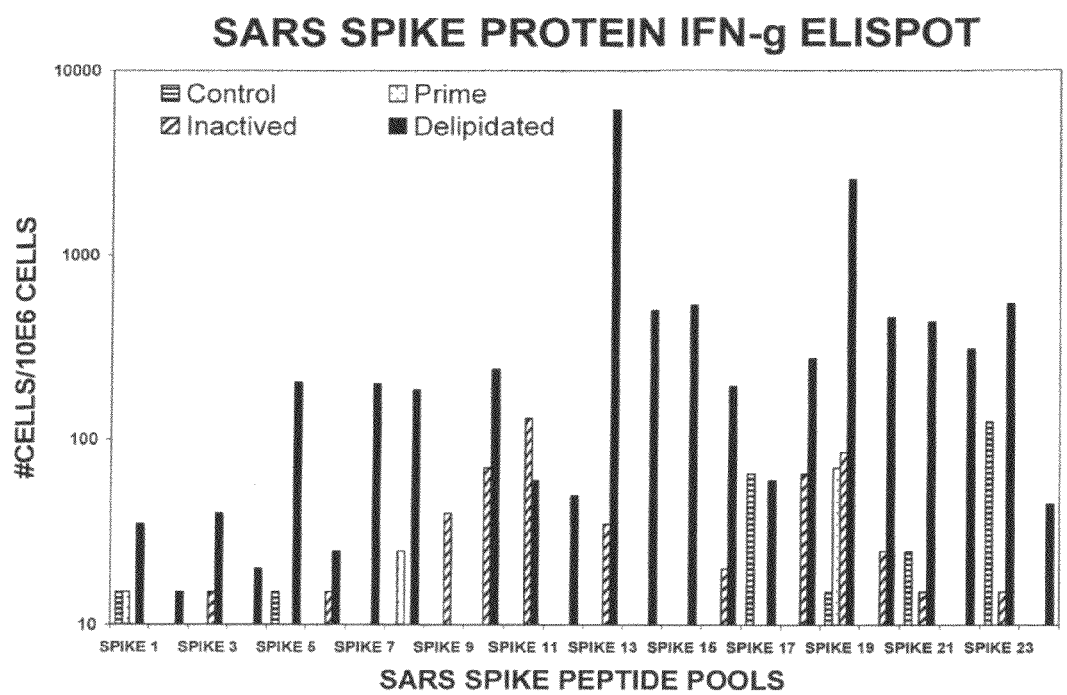
Figure 10:
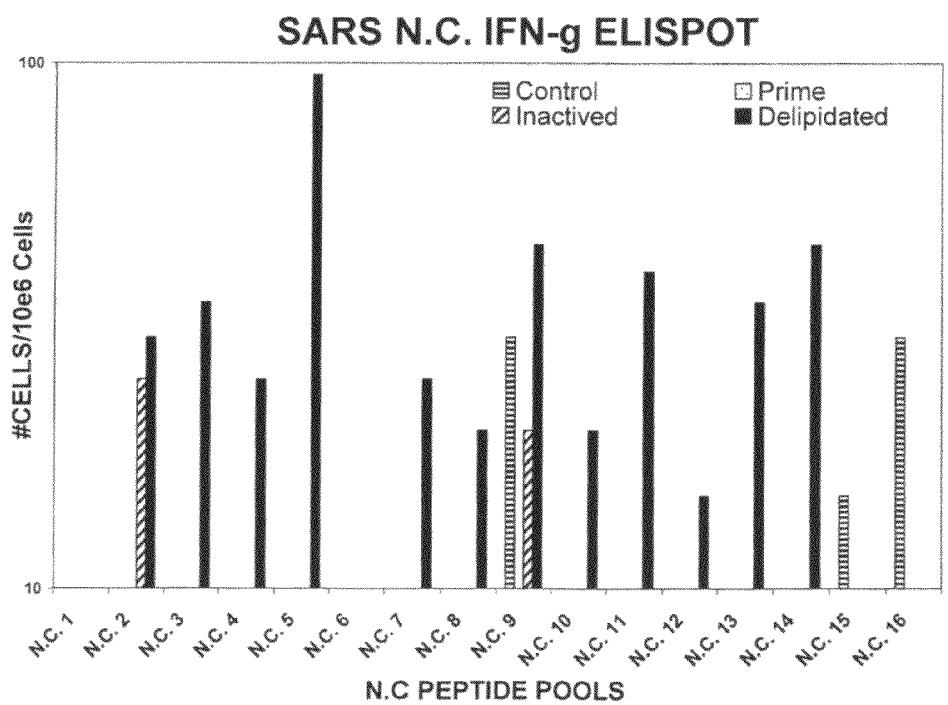

FIG. 8 illustrates the neutralization titers from Experiment #2 comparing the titers in mice vaccinated with delipidated SARS to mice vaccinated with inactivated SARS. Titers obtained from mice vaccinated with 10 µg delipidated SARS had the highest neutralization titers, followed by mice vaccinated with 1 µg, then 0.1 µg delipidated SARS (FIG. 8 top panel). The neutralization titers in mice boosted with either delipidated or inactivated SARS (FIG. 8 bottom panel) were not significantly different, although a clear boosting response was observed when compared to the primed only group. These results were surprising, since the Ab titers to Spike and NC were similar in all groups primed and boosted.

From these results, the dose of 10 µg was chosen as the booster injection dose in Experiment #3, which evaluated the cell-mediated immune responses measured using the mouse IFN-γ ELISPOT assay in vaccinated mice.

Experiment #3 SARS-Determining the Cell-Mediated Immune Responses in Mice Boosted with Optimally Delipidated Vaccines The experiment tested the cell-mediated immune responses generated by vaccination with DIPE/TRITON X-100™ (polyethylene glycol p-(1,1,3,3-tetramethylbutyl)-phenyl ether or polyoxyethylene octyl phenyl ether) delipidated SARS at a concentration of 10 µg. The experiment was designed with four mice per group testing the following four Groups: 1) Boosting with inactivated SARS that was treated with DIPE/TRITON X-100™ (polyethylene glycol p-(1,1,3,3-tetramethylbutyl)-phenyl ether or polyoxyethylene octyl phenyl ether); 2) Boosting with inactivated SARS; 3) Primed only; and, 4) No prime/no boost.

All mice in groups 1, 2, and 3 were primed with the same SARS supernatant (100 sc in incomplete Freunds adjuvant obtained from LRRI), as per Experiment #2. Mice received a booster injection two weeks post priming i.v., and were sacrificed one week later since cell mediated immune responses in mice peak at about one week after a booster injection. Cell-mediated immune responses were measured using murine interferon-gamma (IFN-γ) ELISPOT Assay, per manufacturer's protocol (MABTech). Cells were incubated with pools of peptides covering the entire SARS CoV NC and Spike proteins (FIG. 9).

Pools of peptides (eight peptides per pool for NC, 12 peptides per pool for Spike, 13- to 20-mers with approximately 10 amino acid overlaps) were generated using SARS Overlapping Peptide Array, which was obtained through the NIH Biodefense and Emerging Infections Research Resources Repository, NIAID, NIH. The four digit number in each cell of each table represents a peptide whose amino acid sequence in shown in FIG. 9. The numbers 1-7 at the top of each column for the top table called NC are pool components. For example, pool 1 contains peptides 9539-9589 for NC peptides pool. The amino acid sequences for each NC peptide shown in FIG. 9 is included in Table 3.

The numbers 1-12 at the top of each column for the bottom table called Spike are pool components. For example, pool 12 contains peptides 9609-9765 for the Spike peptide pool. The amino acid sequences for each S peptide shown in FIG. 9 is included in Table 4.

The ELISPOT data showed a significantly enhanced peptide pool response for both NC and Spike in mice vaccinated with delipidated SARS, compared to either the inactivated SARS vaccination, or primed only mice. Surprisingly, mice vaccinated with inactivated SARS did not show robust ELISPOT responses, compared to mice boosted with delipidated SARS.

Discussion

The experiments measured the immune responses in vivo in mice vaccinated with delipidated or inactivated SARS. Experiment #1 tested delipidation methods for use in the dose-escalation study in Experiment #2. We focused on a single immunization with SARS delipidated by 3% DIPE, DIPE:n-BuOH, or DIPE/TRITON X-100™ (polyethylene glycol p-(1,1,3,3-tetramethylbutyl)-phenyl ether or polyoxyethylene octyl phenyl ether). Total IgG Ab titers to SARS Spike and NC antigens were measured, as well as the neutralization Ab titers. FIG. 4 illustrates the Ab titers to SARS Spike and NC. The Ab titers from SARS delipidated with the three different methods were similar. The neutralization Ab titers (FIG. 5) showed that mice vaccinated with DIPE/TRITON X-100™ (polyethylene glycol p-(1,1,3,3-tetramethylbutyl)-phenyl ether or polyoxyethylene octyl phenyl ether) had slightly higher neutralization titers (>60%). The overall titers were low compared to the positive control sera (data not shown), probably because mice were given one vaccination prior to serum collection.

Experiment #2 was a prime/boost protocol, which compared boosting primed mice with 0.1 μg, 1 μg, and 10 μg inactivated SARS or DIPE/TRITON X-100™ (polyethylene glycol p-(1,1,3,3-tetramethylbutyl)-phenyl ether or polyoxyethylene octyl phenyl ether) delipidated SARS vaccines. Priming was performed using a SARS supernatant propagated at LRRI, which had been irradiated by Dr. Dean Erdman at the CDC. The prime/boost strategy was adopted because this protocol would enhance both cell-and humoral immune responses. Total Ab titers to SARS Spike and NC were similar in mice boosted with either inactivated or delipidated SARS (FIG. 6-*Spike*, FIG. 7-NC). These titers were higher than in mice that were primed only and did not receive a booster injection, indicating a clear enhancement of humoral immune responses by adding a booster injection. A dose-dependant increase in Ab titers was observed in delipidated SARS boosted mice; overall, the 10 μg booster injections—52—US2008 39226.2 gave higher titers than other doses used for booster injections. The neutralizing Ab titers (FIG. 8) also showed a dose-dependant response: 10 μg>1 μg>0.1 μg booster injections.

It was decided that a booster injection of 10 μg DIPE/TRITON X-100™ (polyethylene glycol p-(1,1,3,3-tetramethylbutyl)-phenyl ether or polyoxyethylene octyl phenyl ether) delipidated SARS, and the resulting cell-mediated immune responses (measured by IFN-γ ELISPOT) would be compared to a 10 μg inactivated SARS boost. The ELISPOT plates were read using an ELISPOT plate reader. The ELISPOT data (FIG. 10) was surprising. Mice boosted with delipidated SARS had greatly enhanced responses to both Spike and NC peptide pools, compared to mice boosted with inactivated SARS. These data were surprising, since the neutralizing Ab titers in the two groups were similar, and the total Ab titers for both Spike and NC were similar in the two groups.

The data indicate that delipidated SARS vaccination clearly enhanced cell mediated immune responses. The current data indicated that delipidation may favor augmentation of cell mediated immune responses by either enhancing existing pathways of antigen processing and presentation, or by using additional and more efficient pathways of antigen processing and presentation.

Virus Purification: A Direct Pelleting Procedure for Purifying SARS

Gamma-irradiated SARS supernatant was used for priming mice in the prime/boost Experiment #2 and 3. The SARS supernatant used to generate the vaccines for Experiment #1-3, yielded highly purified SARS for the boosting doses, post purification using Dr. Holmes method (as discussed below). Mouse hepatitis virus (MHV) was kindly provided by Dr. Kathryn Holmes, at the University of Colorado Health Sciences. Dr. Holmes purification method for MHV entailed layering viral supernatant onto a 20-55% sucrose gradient made in a tris-maleate buffer.

This purification method for SARS using a different SARS culture propagated by LRRI, was used to yield highly purified virus that was subsequently used as the boosts for Experiment #1, 2, and 3. It was determined that SARS can be efficiently purified by layering the supernatant on a 20-55% sucrose gradient and spinning at 32,000 rpm for 4 hr at 4° C.

TABLE 3

SARS Nucleocapsid (NC) Peptides

| Cat # | SEQ ID NO: | Peptide Sequence |
|---|---|---|
| 9539 | 1 | MSDNGPQSNQRSAPRI |
| 9540 | 2 | QSNQRSAPRITFGGPTDS |
| 9541 | 3 | RITFGGPTDSTDNNQNGGR |
| 9542 | 4 | STDNNQNGGRNGARPKQR |
| 9543 | 5 | GRNGARPKQRRPQGL |
| 9544 | 6 | RPKQRRPQGLPNNTASWF |
| 9545 | 7 | GLPNNTASWFTALTQHGK |
| 9546 | 8 | WFTALTQHGKEELRFPR |
| 9547 | 9 | HGKEELRFPRGQGVPI |
| 9548 | 10 | RFPRGQGVPINTNSGPDDQI |
| 9549 | 11 | NTNSGPDDQIGYYRRATR |
| 9550 | 12 | QIGYYRRATRRVRGGDGK |
| 9551 | 13 | TRRVRGGDGKMKELSPRW |
| 9552 | 14 | GKMKELSPRWYFYYL |
| 9553 | 15 | LSPRWYFYYLGTGPEASL |
| 9554 | 16 | YLGTGPEASLPYGANK |
| 9555 | 17 | EASLPYGANKEGIVWVA |
| 9556 | 18 | ANKEGIVWVATEGAL |
| 9557 | 19 | IVWVATEGALNTPKDHI |
| 9558 | 20 | GALNTPKDHIGTRNPNNNA |
| 9559 | 21 | IGTRNPNNNAATVLQL |
| 9560 | 22 | NNNAATVLQLPQGTTLPK |
| 9561 | 23 | QLPQGTTLPKGFYAEGSR |
| 9562 | 24 | PKGFYAEGSRGGSQASSR |
| 9563 | 25 | SRGGSQASSRSSSRSR |
| 9564 | 26 | ASSRSSSRSRGNSRNST |
| 9565 | 27 | RSRGNSRNSTPGSSR |
| 9566 | 28 | SRN STPGSSRGNSPARMA |
| 9567 | 29 | SRGNSPARMASGGGETAL |
| 9569 | 30 | ALALLLLDRLNQLESKV |
| 9570 | 31 | DRLNQLESKVSGKGQQQQ |
| 9571 | 32 | KVSGKGQQQQGQTVTKK |
| 9572 | 33 | QQQGQTVTKKSAAEASKK |
| 9573 | 34 | KKSAAEASKKPRQKRTA |
| 9574 | 35 | SKKPRQKRTATKQYNV |

TABLE 3-continued

SARS Nucleocapsid (NC) Peptides

| Cat # | SEQ ID NO: | Peptide Sequence |
|---|---|---|
| 9575 | 36 | KRTATKQYNVTQAFGRR |
| 9576 | 37 | YNVTQAFGRRGPEQTQGNF |
| 9577 | 38 | RGPEQTQGNFGDQDLIR |
| 9578 | 39 | GNFGDQDLIRQGTDYKHW |
| 9579 | 40 | IRQGTDYKHWPQIAQFA |
| 9580 | 41 | KHWPQIAQFAPSASAFF |
| 9581 | 42 | QFAPSASAFFGMSRIGM |
| 9582 | 43 | AFFGMSRIGMEVTPSGTW |
| 9583 | 44 | GMEVTPSGTWLTYHGAIK |
| 9584 | 45 | TWLTYHGAIKLDDKDPQF |
| 9585 | 46 | IKLDDKDPQFKDNVILL |
| 9586 | 47 | PQFKDNVILLNKHIDAYK |
| 9587 | 48 | LLNKHIDAYKTFPPTEPK |
| 9588 | 49 | YKTFPPTEPKKDKKKK |
| 9589 | 50 | TEPKKDKKKKTDEAQPL |
| 9590 | 51 | KKKTDEAQPLPQRQKK |
| 9591 | 52 | AQPLPQRQKKQPTVTLL |
| 9592 | 53 | QKKQPTVTLLPAADMDDF |
| 9594 | 54 | LLPAADMDDFSRQLQNSM |
| 9595 | 55 | DFSRQLQNSMSGASA |

TABLE 4

SARS Spike (S) Peptides

| Cat # | SEQ ID NO: | Peptide Sequence |
|---|---|---|
| 9597 | 56 | MFIFLLFLTLTSGSDLDR |
| 9598 | 57 | TLTSGSDLDRCTTFDDV |
| 9599 | 58 | LDRCTTFDDVQAPNYTQH |
| 9601 | 59 | QHTSSMRGVYYPDEIFR |
| 9602 | 60 | GVYYPDEIFRSDTLYL |
| 9603 | 61 | EIFRSDTLYLTQDLFLPF |
| 9604 | 62 | YLTQDLFLPFYSNVTGFH |
| 9605 | 63 | PFYSNVTGFHTINHTF |
| 9606 | 64 | TGFHTINHTFGNPVIPFK |
| 9607 | 65 | TFGNPVIPFKDGIYFAA |
| 9608 | 66 | PFKDGIYFAATEKSNVVR |
| 9609 | 67 | AATEKSNVVRGWVFGSTM |
| 9610 | 68 | VRGWVFGSTMNNKSQSVI |
| 9611 | 69 | TMNNKSQSVIIINNSTNV |

TABLE 4-continued SARS Spike (S) Peptides

| Cat # | SEQ ID NO: | Peptide Sequence |
|---|---|---|
| 9612 | 70 | VIIINNSTNVVIRACNF |
| 9614 | 71 | NFELCDNPFFAVSKPM |
| 9615 | 72 | NPFFAVSKPMGTQTHTMI |
| 9616 | 73 | PMGTQTHTMIFDNAF |
| 9619 | 74 | YISDAFSLDVSEKSGNFK |
| 9620 | 75 | DVSEKSGNFKHLREFVFK |
| 9621 | 76 | FKHLREFVFKNKDGFLYV |
| 9622 | 77 | FKNKDGFLYVYKGYQPI |
| 9623 | 78 | LYVYKGYQPIDVVRDL |
| 9624 | 79 | YQPIDVVRDLPSGFNTLK |
| 9625 | 80 | DLPSGFNTLKPIFKLPL |
| 9626 | 81 | TLKPIFKLPLGINITNFR |
| 9627 | 82 | PLGINITNFRAILTAF |
| 9628 | 83 | TNFRAILTAFSPAQDIW |
| 9629 | 84 | TAFSPAQDIWGTSAAAYF |
| 9631 | 85 | AAAYFVGYLKPTTFMLKY |
| 9632 | 86 | LKPTTFMLKYDENGTI |
| 9633 | 87 | MLKYDENGTITDAVDCSQ |
| 9634 | 88 | TITDAVDCSQNPLAELK |
| 9636 | 89 | LKCSVKSFEIDKGIY |
| 9637 | 90 | KSFEIDKGIYQTSNFRVV |
| 9638 | 91 | IYQTSNFRVVPSGDVVRF |
| 9639 | 92 | VVPSGDVVRFPNITNL |
| 9640 | 93 | VVRFPNITNLCPFGEVF |
| 9641 | 94 | TNLCPFGEVFNATKFPSV |
| 9642 | 95 | VFNATKFPSVYAWERKKI |
| 9643 | 96 | SVYAWERKKISNCVADY |
| 9644 | 97 | KKISNCVADYSVLYNSTF |
| 9645 | 98 | DYSVLYNSTFFSTFKCY |
| 9646 | 99 | STFFSTFKCYGVSATKL |
| 9647 | 100 | KCYGVSATKLNDLCFSNV |
| 9648 | 101 | KLNDLCFSNVYADSFVVK |
| 9649 | 102 | NVYADSFVVKGDDVRQIA |
| 9650 | 103 | VKGDDVRQIAPGQTGVIA |
| 9651 | 104 | IAPGQTGVIADYNYKL |
| 9652 | 105 | GVIADYNYKLPDDFMGCV |
| 9653 | 106 | KLPDDFMGCVLAWNTRNI |
| 9655 | 107 | NIDATSTGNYNYKYRYLR |
| 9656 | 108 | NYNYKYRYLRHGKLRPF |
| 9657 | 109 | YLRHGKLRPFERDISNV |
| 9658 | 110 | RPFERDISNVPFSPDGK |
| 9659 | 111 | SNVPFSPDGKPCTPPAL |
| 9660 | 112 | DGKPCTPPALNCYWPL |
| 9661 | 113 | PPALNCYWPLNDYGFY |
| 9663 | 114 | GFYTTTGIGYQPYRVVVL |
| 9665 | 115 | VVLSFELLNAPATVCGPK |
| 9666 | 116 | NAPATVCGPKLSTDLIK |
| 9667 | 117 | GPKLSTDLIKNQCVNFNF |
| 9668 | 118 | IKNQCVNFNFNGLTGTGV |
| 9669 | 119 | NFNGLTGTGVLTPSSKRF |
| 9670 | 120 | GVLTPSSKRFQPFQQFGR |
| 9671 | 121 | RFQPFQQFGRDVSDF |
| 9672 | 122 | QQFGRDVSDFTDSVRDPK |
| 9673 | 123 | DFTDSVRDPKTSEILDI |
| 9674 | 124 | DPKTSEILDISPCSFGGV |
| 9675 | 125 | DISPCSFGGVSVITPGTNA |
| 9676 | 126 | VSVITPGTNASSEVAVLY |
| 9678 | 127 | LYQDVNCTDVSTAIHA |
| 9679 | 128 | CTDVSTAIHADQLTPAWR |
| 9680 | 129 | HADQLTPAWRIYSTGNNV |
| 9681 | 130 | WRIYSTGNNVFQTQAGCL |
| 9682 | 131 | NVFQTQAGCLIGAEHV |
| 9684 | 132 | HVDTSYECDIPIGAGICA |
| 9685 | 133 | DIPIGAGICASYHTVSLL |
| 9686 | 134 | CASYHTVSLLRSTSQKSI |
| 9687 | 135 | LLRSTSQKSIVAYTMSL |
| 9688 | 136 | KSIVAYTMSLGADSSIAY |
| 9689 | 137 | SLGADSSIAYSNNTIAI |
| 9690 | 138 | IAYSNNTIAIPTNFSISI |
| 9691 | 139 | AIPTNFSISITTEVMPV |
| 9692 | 140 | ISITTEVMPVSMAKTSV |
| 9694 | 141 | KTSVDCNMYICGDSTECA |
| 9697 | 142 | LQYGSFCTQLNRALSGIA |
| 9698 | 143 | QLNRALSGIAAEQDRNTR |
| 9699 | 144 | IAAEQDRNTREVFAQVK |
| 9700 | 145 | NTREVFAQVKQMYKTPTL |

TABLE 4-continued

SARS Spike (S) Peptides

| Cat # | SEQ ID NO: | Peptide Sequence |
|---|---|---|
| 9701 | 146 | VKQMYKTPTLKYFGGFNF |
| 9702 | 147 | TLKYFGGFNFSQILPDPL |
| 9703 | 148 | NFSQILPDPLKPTKRSFI |
| 9704 | 149 | PLKPTKRSFIEDLLFNKV |
| 9705 | 150 | FIEDLLFNKVTLADAGFM |
| 9706 | 151 | KVTLADAGFMKQYGECL |
| 9707 | 152 | GFMKQYGECLGDINARDL |
| 9708 | 153 | CLGDINARDLICAQKF |
| 9709 | 154 | ARDLICAQKFNGLTVL |
| 9710 | 155 | AQKFNGLTVLPPLLTDDM |
| 9711 | 156 | VLPPLLTDDMIAAYTAAL |
| 9713 | 157 | AALVSGTATAGWTFGAGA |
| 9715 | 158 | GAALQIPFAMQMAYRF |
| 9716 | 159 | PFAMQMAYRFNGIGV |
| 9718 | 160 | GIGVTQNVLYENQKQIA |
| 9719 | 161 | VLYHNQKQIANQFNKAI |
| 9721 | 162 | KAISQIQESLTTTSTAL |
| 9723 | 163 | TALGKLQDVVNQNAQAL |
| 9725 | 164 | QALNTLVKQLSSNFGAI |
| 9727 | 165 | AISSVLNDILSRLDKVEA |
| 9728 | 166 | ILSRLDKVEAEVQIDRLI |
| 9731 | 167 | SLQTYVTQQLIRAAEIRA |
| 9732 | 168 | QLIRAAEIRASANLAATK |
| 9733 | 169 | RASANLAATKMSECVL |
| 9734 | 170 | AATKMSECVLGQSKRVDF |
| 9735 | 171 | VLGQSKRVDFCGKGYHLM |
| 9736 | 172 | DFCGKGYHLMSFPQAAPH |
| 9737 | 173 | LMSFPQAAPHGVVFLHV |
| 9738 | 174 | APHGVVFLHVTYVPSQER |

TABLE 4-continued

SARS Spike (S) Peptides

| Cat # | SEQ ID NO: | Peptide Sequence |
|---|---|---|
| 9739 | 175 | HVTYVPSQERNFTTAPAI |
| 9740 | 176 | ERNFTTAPAICHEGKAYF |
| 9741 | 177 | AICHEGKAYFPREGVFVF |
| 9742 | 178 | YFPREGVFVFNGTSWFI |
| 9743 | 179 | FVFNGTSWFITQRNFF |
| 9744 | 180 | SWFITQRNFFSPQII |
| 9745 | 181 | QRNFFSPQIITTDNTFV |
| 9748 | 182 | VIGIINNTVYDPLQPEL |
| 9749 | 183 | TVYDPLQPELDSFKEEL |
| 9750 | 184 | PELDSFKEELDKYFKNH |
| 9751 | 185 | EELDKYFKNHTSPDVDL |
| 9752 | 186 | KNHTSPDVDLGDISGINA |
| 9753 | 187 | DLGDISGINASVVNIQK |
| 9754 | 188 | INASVVNIQKEIDRLNEV |
| 9755 | 189 | QKEIDRLNEVAKNLNESL |
| 9756 | 190 | EVAKNLNESLIDLQELGK |
| 9757 | 191 | SLIDLQELGKYEQYIKW |
| 9758 | 192 | LGKYEQYIKWPWYVWLGF |
| 9759 | 193 | KWPWYVWLGFIAGLIAIV |
| 9760 | 194 | GFIAGLIAIVMVTILL |
| 9761 | 195 | IAIVMVTILLCCMTSCCSCL |
| 9762 | 196 | CCMTSCCSCLKGACSCGS |
| 9763 | 197 | CLKGACSCGSCCKFDEDD |
| 9764 | 198 | GSCCKFDEDDSEPVLKGV |
| 9765 | 199 | DDSEPVLKGVKLHYT |

All patents, publications and abstracts cited above are incorporated herein by reference in their entirety. It should be understood, of course, that the foregoing relates only to preferred embodiments of the present invention and that numerous modifications or alterations may be made therein without departing from the spirit and the scope of the invention as set forth in the appended claims.

We claim:

1. A composition comprising a modified, partially delipidated viral particle of a coronavirus, wherein the modified, partially delipidated viral particle of the coronavirus
   is immunogenic,
   is of reduced infectivity as compared to the coronavirus not subjected to delipidation, and
   comprises an envelope with envelope viral and host proteins and a lower lipid content as compared to an envelope in the coronavirus not subjected to delipidation,
   wherein the modified, partially delipidated viral particle is produced by exposing the coronavirus not subjected to delipidation to a partial delipidation process consisting essentially of treating the coronavirus with 0.01% to 3% solvent,
   and wherein the solvent is an ether, a fluoroether, an alcohol, or a combination thereof.

2. A composition comprising a modified, partially delipidated viral particle of a coronavirus, wherein the modified, partially delipidated viral particle of the coronavirus
   is immunogenic,
   is of reduced infectivity as compared to the coronavirus not subjected to delipidation, and
   comprises an envelope with envelope viral and host proteins and a lower lipid content as compared to an envelope in the coronavirus not subjected to delipidation,
   wherein the modified, partially delipidated viral particle is produced by exposing the coronavirus not subjected to delipidation to a partial delipidation process consisting essentially of treating the coronavirus with 0.01% to 3% solvent, wherein the solvent is a combination of a surfactant and the ether, the fluoroether, the alcohol or the combination thereof.

3. The composition of claim 2, wherein the ether is diisopropyl ether and the alcohol is butanol.

4. The composition of claim 2, wherein the fluoroether is sevoflurane.

5. The composition of claim 2, wherein the surfactant is polyethylene glycol p-(1,1,3,3-tetramethylbutyl)-phenyl ether.

6. The composition of claim 2, wherein the ether is diisopropyl ether and the surfactant is polyethylene glycol p-(1,1,3,3-tetramethylbutyl)-phenyl ether.

7. The composition of claim 2, wherein the solvent is a combination of
   a surfactant, an alcohol and an ether,
   a surfactant, an alcohol and a fluoroether,
   an alcohol and a surfactant,
   an ether and a surfactant, or
   an alcohol, an ether and a surfactant.

8. A method of creating a modified, partially delipidated viral particle of a coronavirus comprising the steps of:
   receiving a coronavirus in a fluid,
   exposing the coronavirus to a delipidation process, consisting essentially of treating the coronavirus with 0.01% to 3% solvent,
   wherein the solvent is an ether, a fluoroether, an alcohol, a combination thereof, or a combination of a surfactant and the ether, the fluoroether, the alcohol or the combination thereof, and
   wherein the delipidation process decreases the lipid content of a viral envelope of the coronavirus.

9. The method of claim 8, wherein the ether is diisopropyl ether and the alcohol is butanol.

10. The method of claim 8, wherein the fluoroether is sevoflurane.

11. The method of claim 8, wherein the surfactant is polyethylene glycol p-(1,1,3,3-tetramethylbutyl)-phenyl ether.

12. The method of claim 8, wherein the ether is diisopropyl ether and the surfactant is polyethylene glycol p-(1,1,3,3-tetramethylbutyl)-phenyl ether.

13. The method of claim 8, wherein the combination thereof is an alcohol and an ether, an alcohol and a fluoroether, an alcohol and a surfactant, an ether and a surfactant, or an alcohol, an ether and a surfactant.

14. A method of inducing an immune response to a coronavirus in an animal or a human comprising:
   removing blood containing the coronavirus from the animal or the human;
   obtaining plasma from the blood, the plasma containing the coronavirus;
   delipidating the coronavirus by a process consisting essentially of contacting the plasma containing the coronavirus with a 0.01% to 3% solvent capable of extracting lipid from the coronavirus to produce modified, partially delipidated viral particles of the coronavirus, wherein the solvent is an ether, a fluoroether, an alcohol, a combination thereof, or a combination of a surfactant and the ether, the fluoroether, the alcohol or the combination thereof, wherein the modified, partially delipidated particles are of reduced infectivity and reduced lipid content as compared to the coronavirus not subjected to the delipidation process, and, wherein the modified, partially delipidated particles comprise a modified viral envelope with envelope viral and host proteins, wherein the contacting is for a time and under conditions sufficient to reduce the infectivity and the lipid content of the coronavirus to produce the modified, partially delipidated coronavirus viral particles;

separating the solvent from the modified, partially delipidated viral particles; and administering the modified, partially delipidated viral particles of the coronavirus to the animal or the human in an amount sufficient to produce a cellular immune response or an antibody response to the coronavirus in the animal or the human.

15. The method of claim 14, wherein the combination thereof is an alcohol and an ether, an alcohol and a fluoroether, an alcohol and a surfactant, an ether and a surfactant, or an alcohol, an ether and a surfactant.

* * * * *